United States Patent
Koo et al.

(10) Patent No.: US 12,265,087 B2
(45) Date of Patent: Apr. 1, 2025

(54) OLFACTORY RECEPTOR AS MICROGLIA MARKER AND USE THEREOF

(71) Applicant: DAEGU GYEONGBUK INSTITUTE OF SCIENCE AND TECHNOLOGY, Daegu (KR)

(72) Inventors: Jae Hyung Koo, Daegu (KR); Na Hye Lee, Daegu (KR); Yoon Gyu Jae, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 551 days.

(21) Appl. No.: 17/622,546

(22) PCT Filed: Jun. 26, 2020

(86) PCT No.: PCT/KR2020/008344
§ 371 (c)(1),
(2) Date: Dec. 23, 2021

(87) PCT Pub. No.: WO2020/263011
PCT Pub. Date: Dec. 30, 2020

(65) Prior Publication Data
US 2022/0357342 A1    Nov. 10, 2022

(30) Foreign Application Priority Data
Jun. 27, 2019    (KR) .................. 10-2019-0077256

(51) Int. Cl.
*A61K 31/341*    (2006.01)
*A61P 25/00*    (2006.01)
*G01N 33/569*    (2006.01)
*G01N 33/68*    (2006.01)

(52) U.S. Cl.
CPC ....... *G01N 33/6872* (2013.01); *A61K 31/341* (2013.01); *A61P 25/00* (2018.01); *G01N 33/569* (2013.01)

(58) Field of Classification Search
None
See application file for complete search history.

(56) References Cited

FOREIGN PATENT DOCUMENTS

| | | |
|---|---|---|
| JP | 2019-39711 A | 3/2019 |
| KR | 10-2014-0134170 A | 11/2014 |
| KR | 10-2017-0077102 A | 7/2017 |
| KR | 10-1851603 B | 4/2018 |

OTHER PUBLICATIONS

Gaudel, F. et al., "Expression of the Cerebral Olfactory Receptors Olfr110/111 and Olfr544 Is Altered During Aging and in Alzheimer's Disease-Like Mice", Molecular Neurobiology (2019).
Lee, N. H. et al., "A pathogen-derived metabolite induces microglial activation via odorant Receptors", The FEBS journal, Jan. 30, 2020.
International Search Report PCT/ISA/210 for International Application No. PCT/KR2020/008344 Dated Jun. 26, 2020.

*Primary Examiner* — Jennifer E Graser
(74) *Attorney, Agent, or Firm* — Sughrue Mion, PLLC

(57) ABSTRACT

Provided are an odorant receptor marker of microglia and a use thereof, and according to the odorant receptor marker of microglia and a use thereof according to one aspect, microglia may be detected by measuring an activity or expression level of a protein of an odorant receptor (OR) Olfr110 or Olfr111, and OR ligands of microglia may be selected using them, and an inhibitor or activator against the interaction between the OR and 2-pentylfuran is effectively used in treatment of a neuroinflammatory disease or meningitis.

5 Claims, 55 Drawing Sheets

[FIG.1]
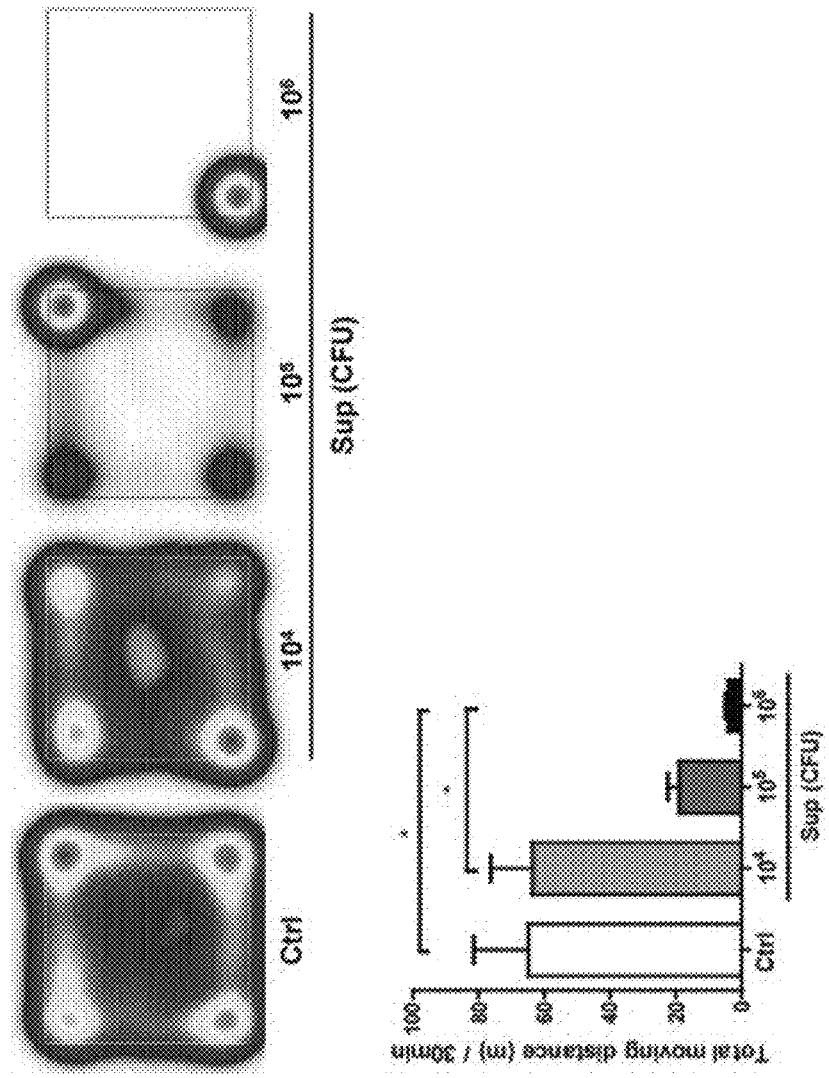

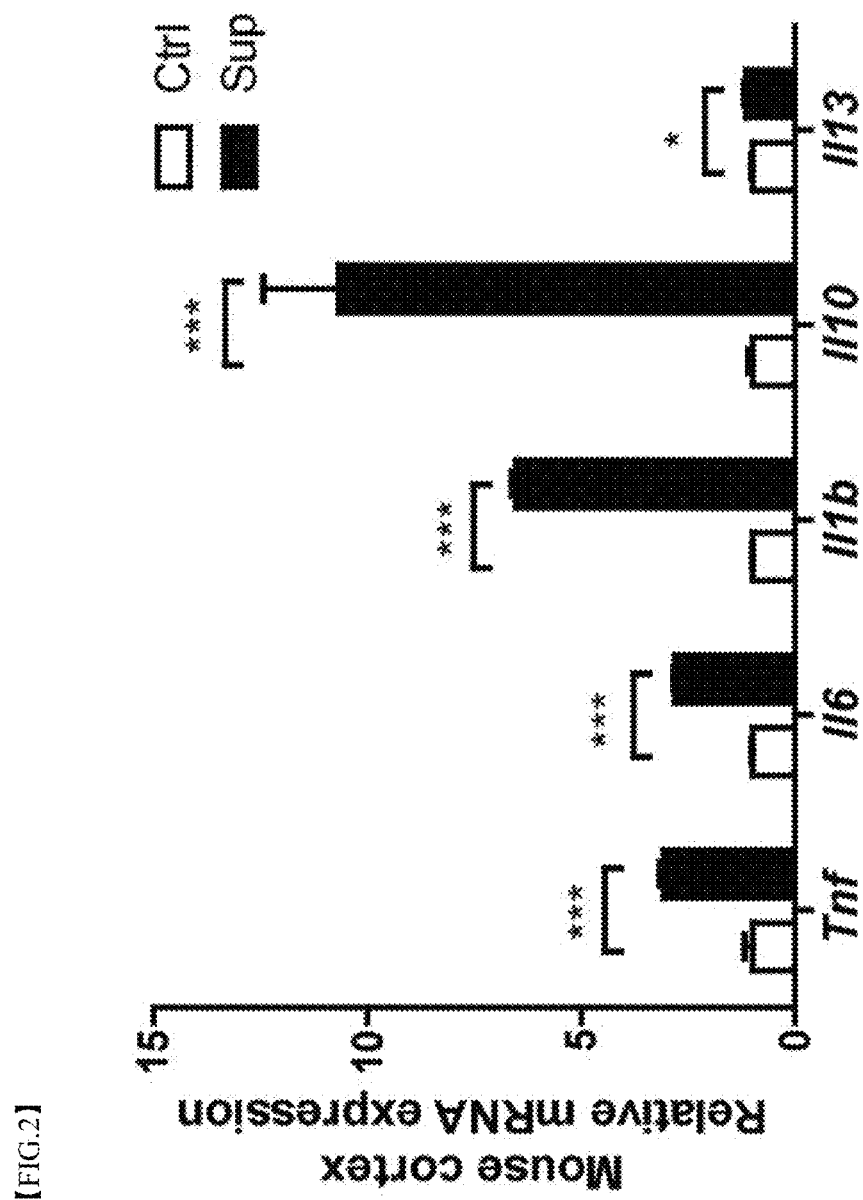
[FIG.2]

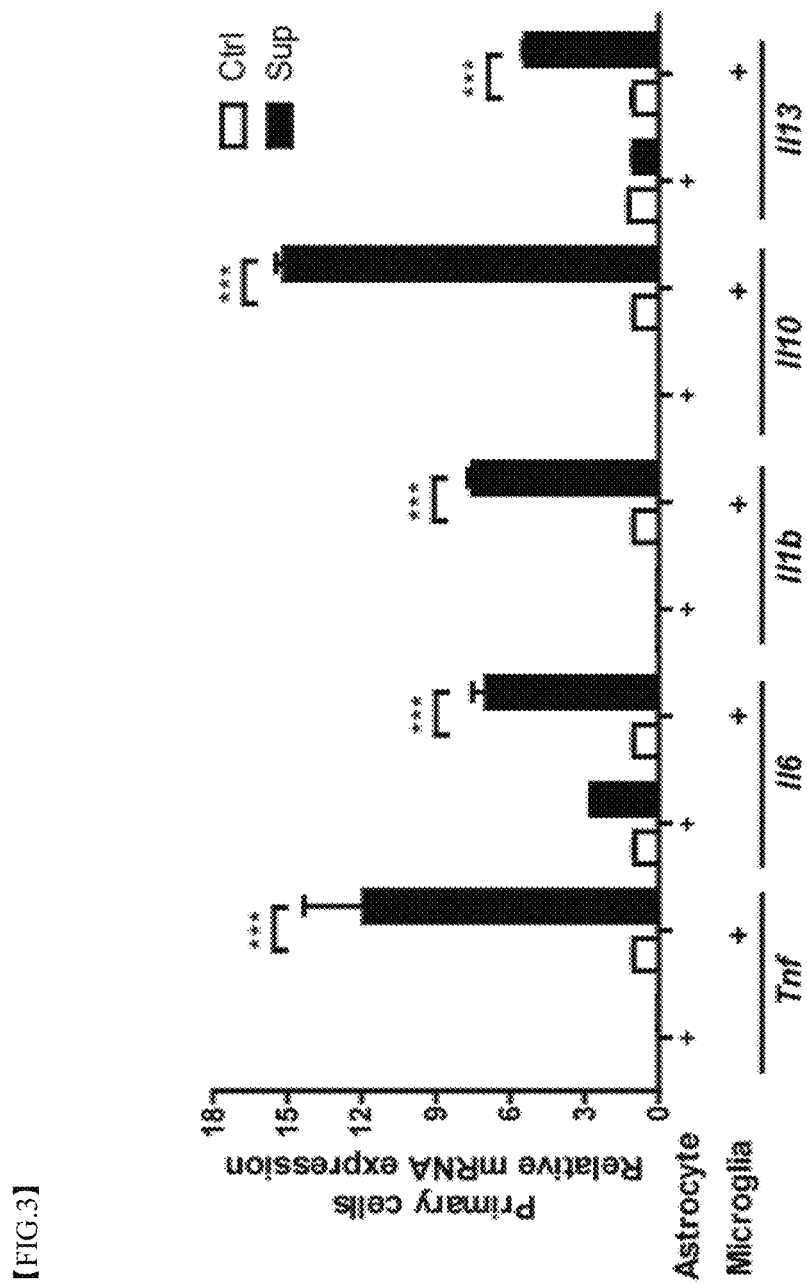
[FIG.3]

[FIG.4]
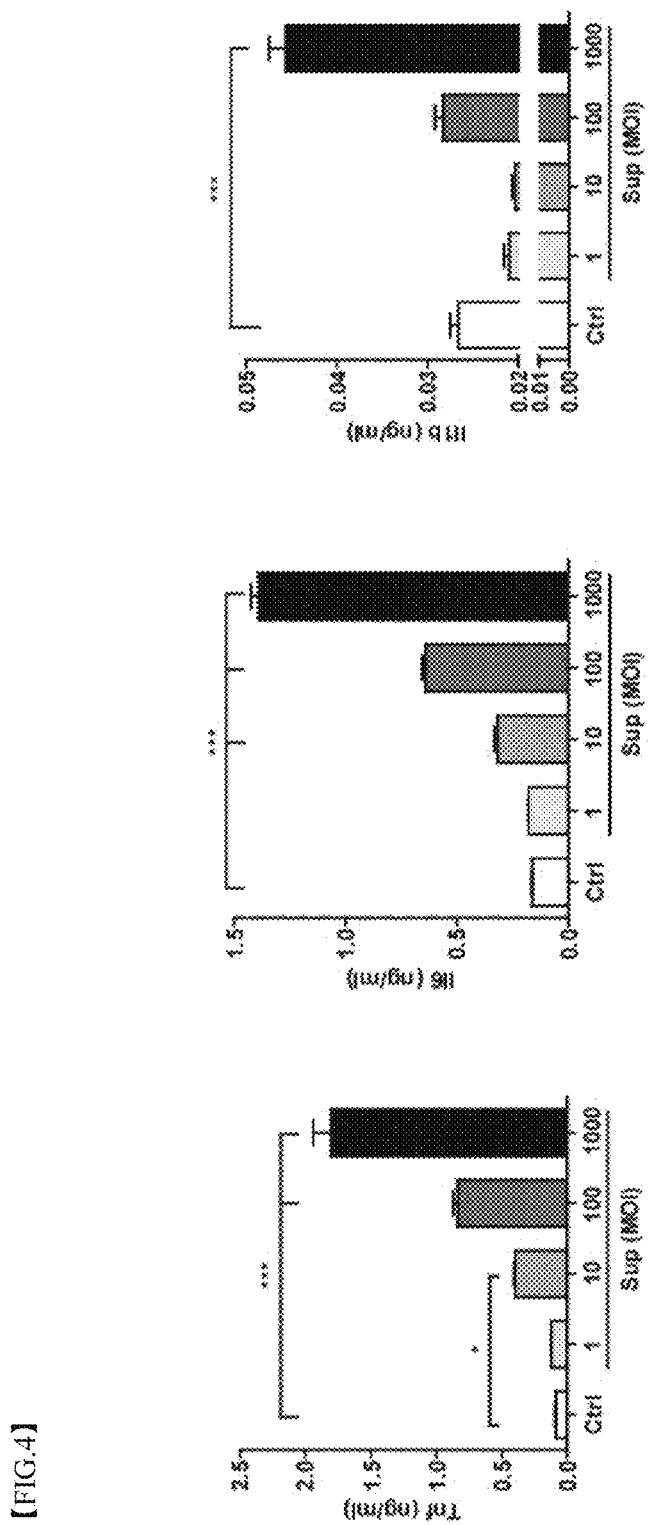

[FIG.5]
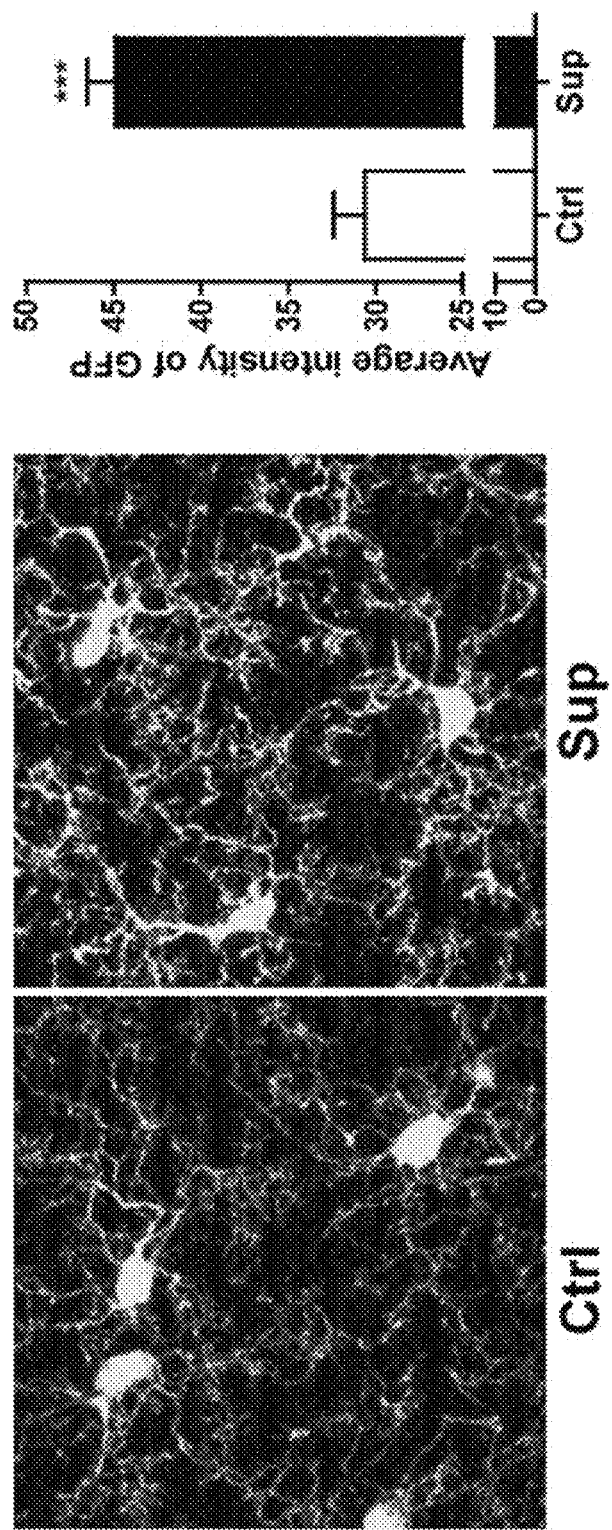

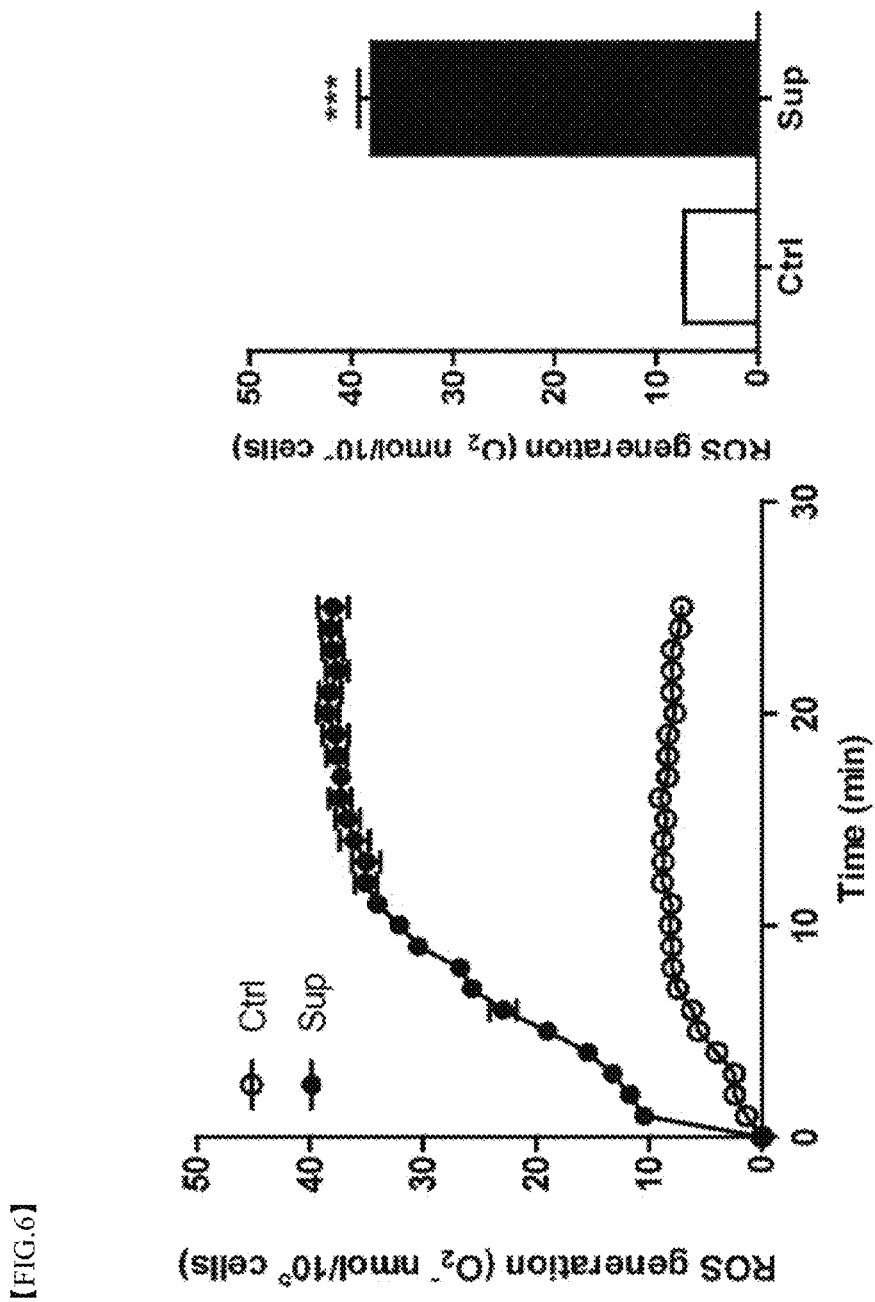
[FIG.6]

[FIG.7]
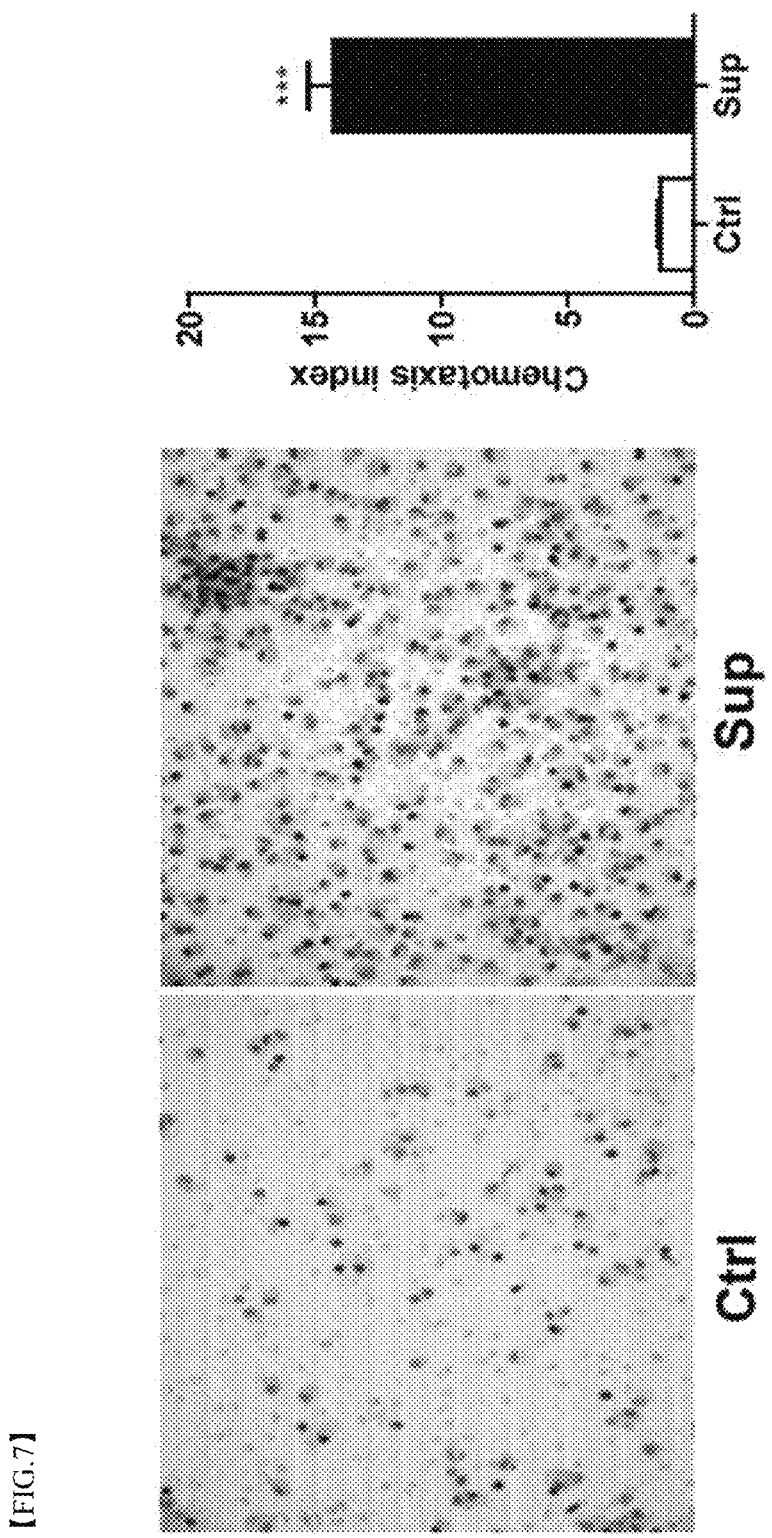

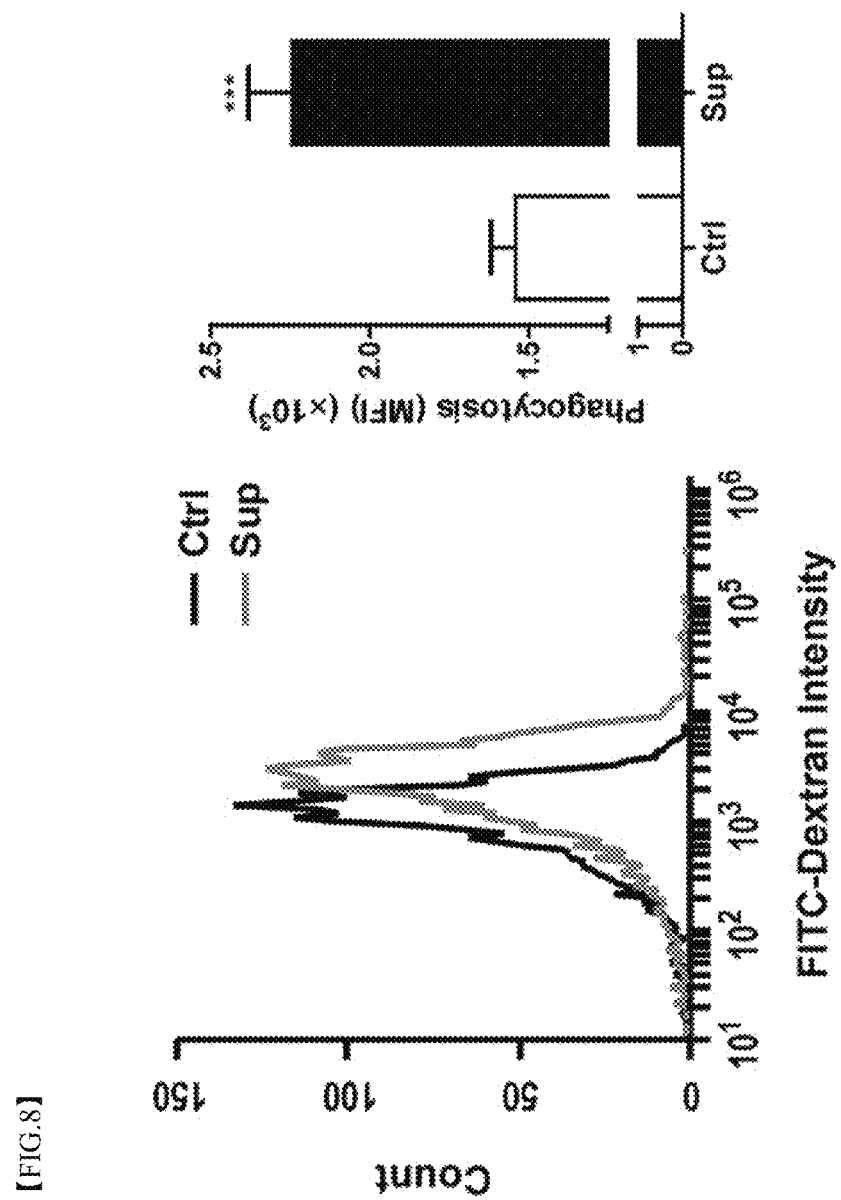
[FIG.8]

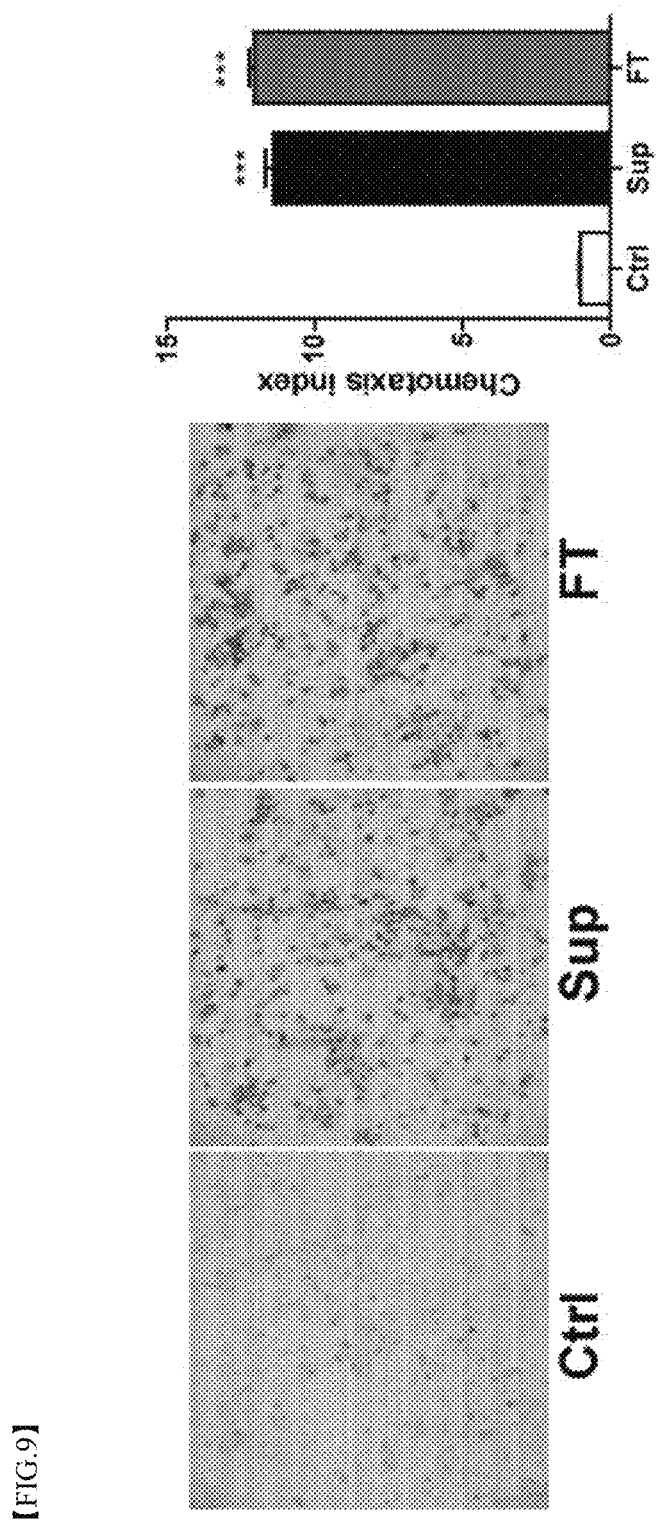
[FIG.9]

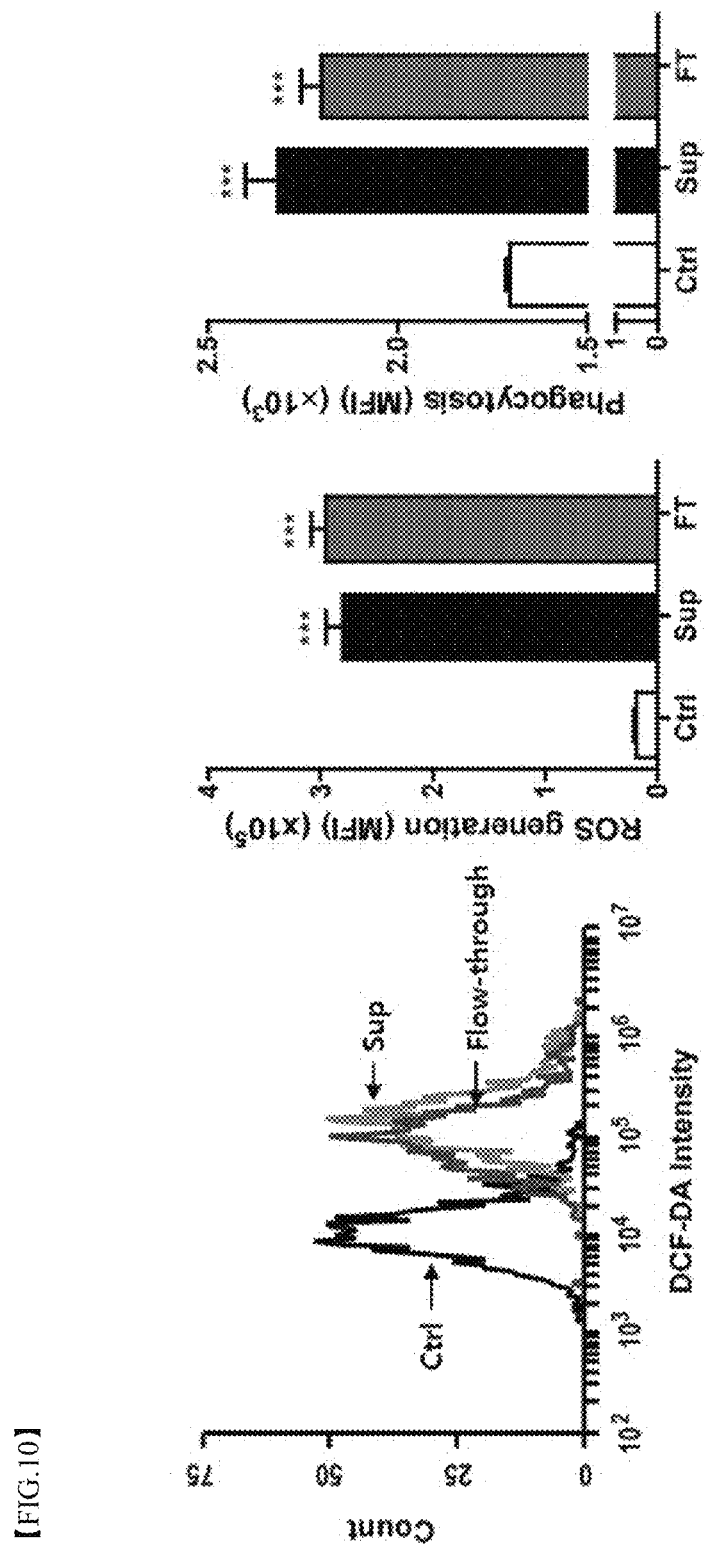
[FIG.10]

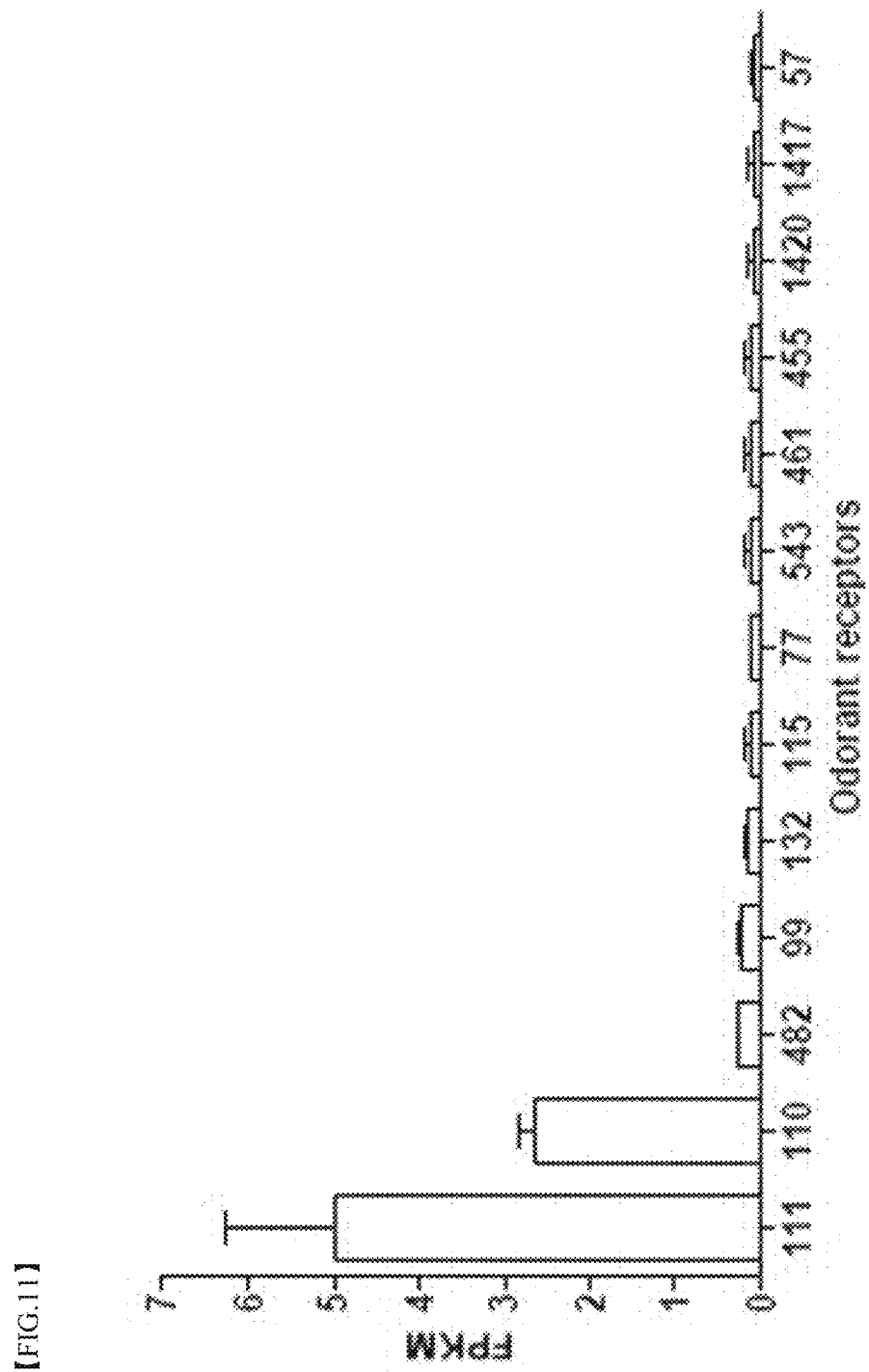
[FIG.11]

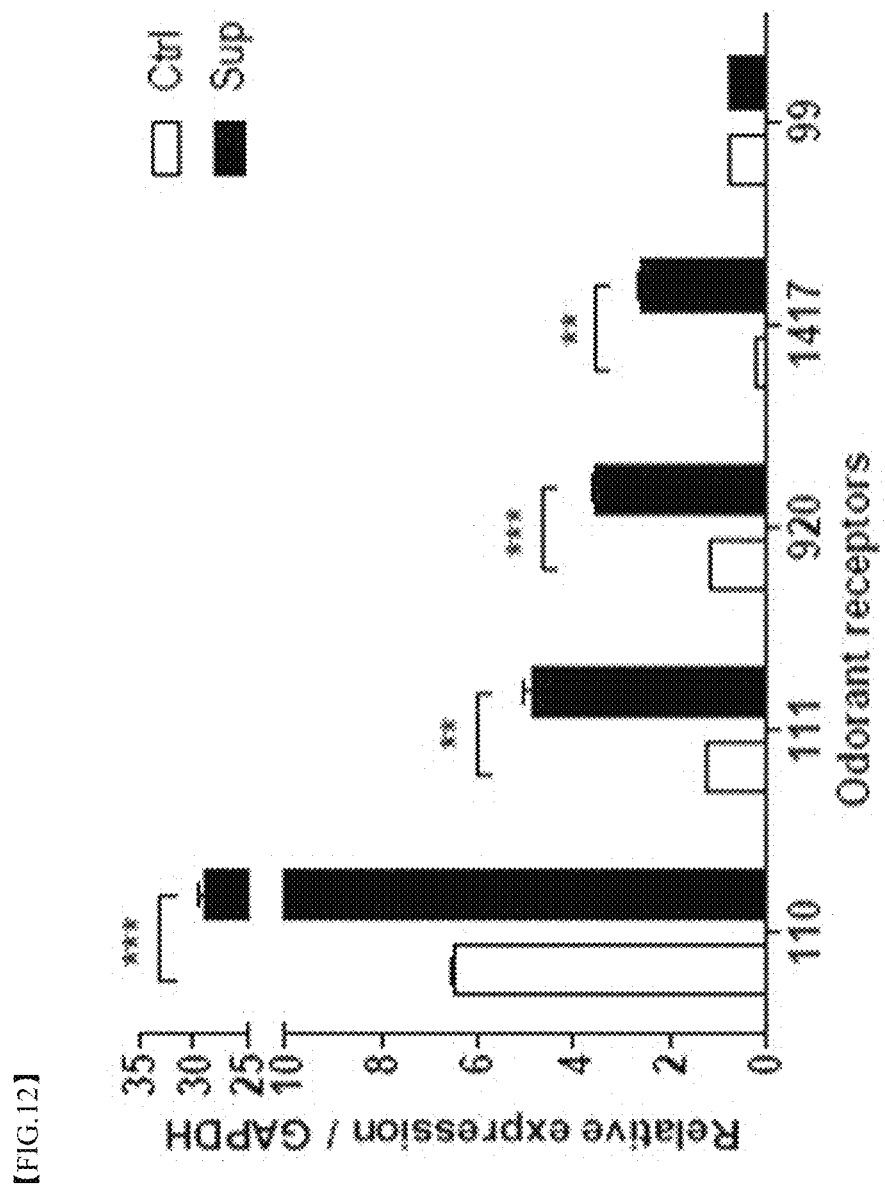
[FIG.12]

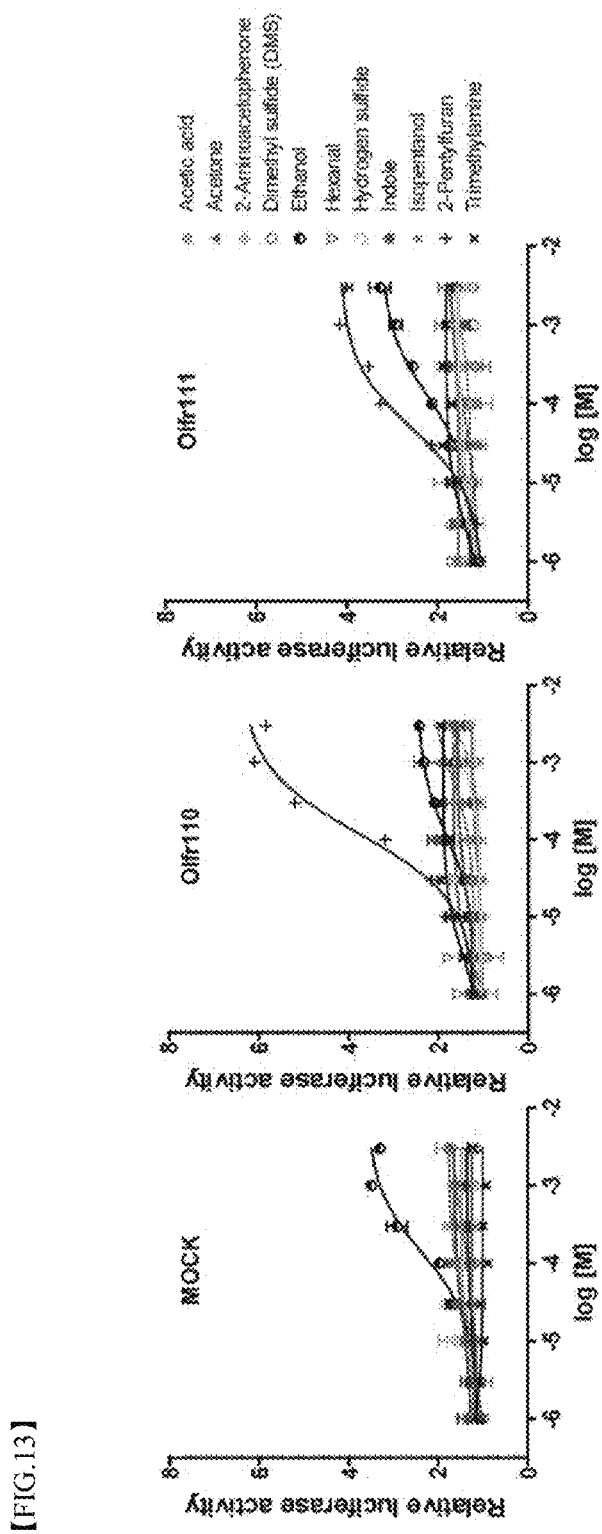
[FIG.13]

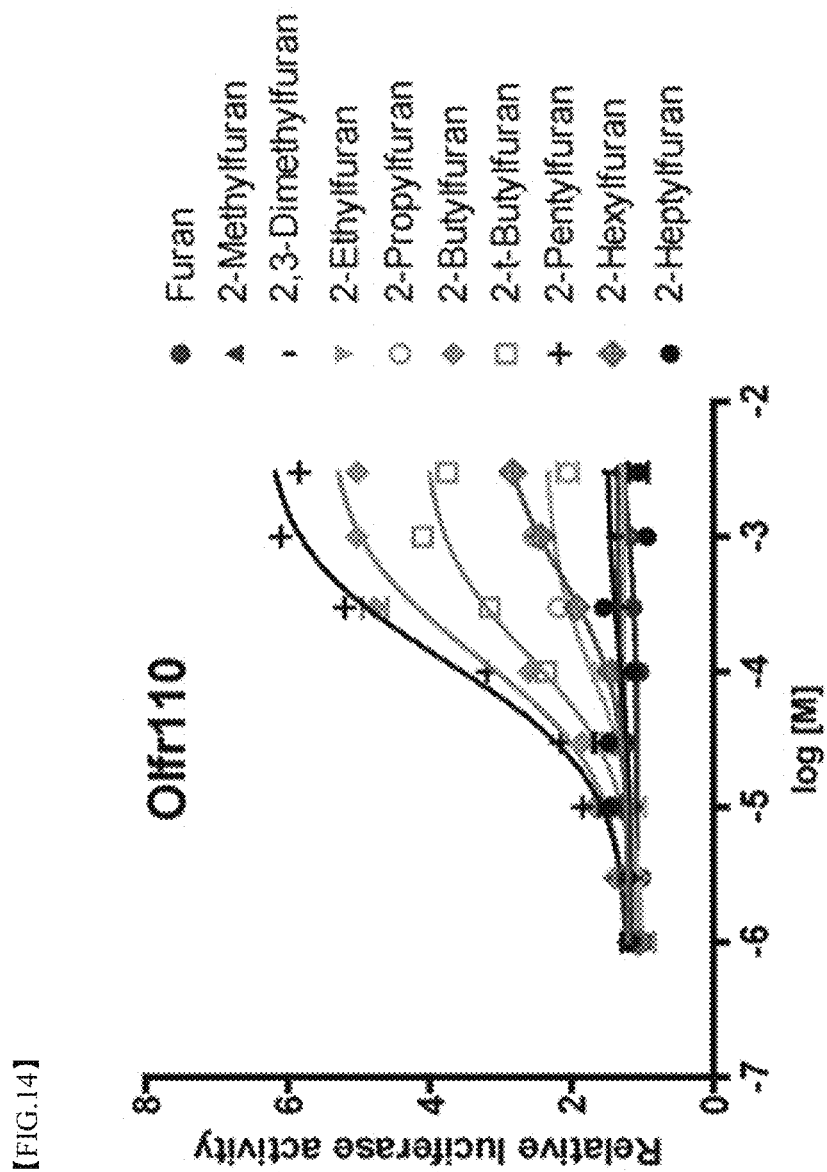
[FIG.14]

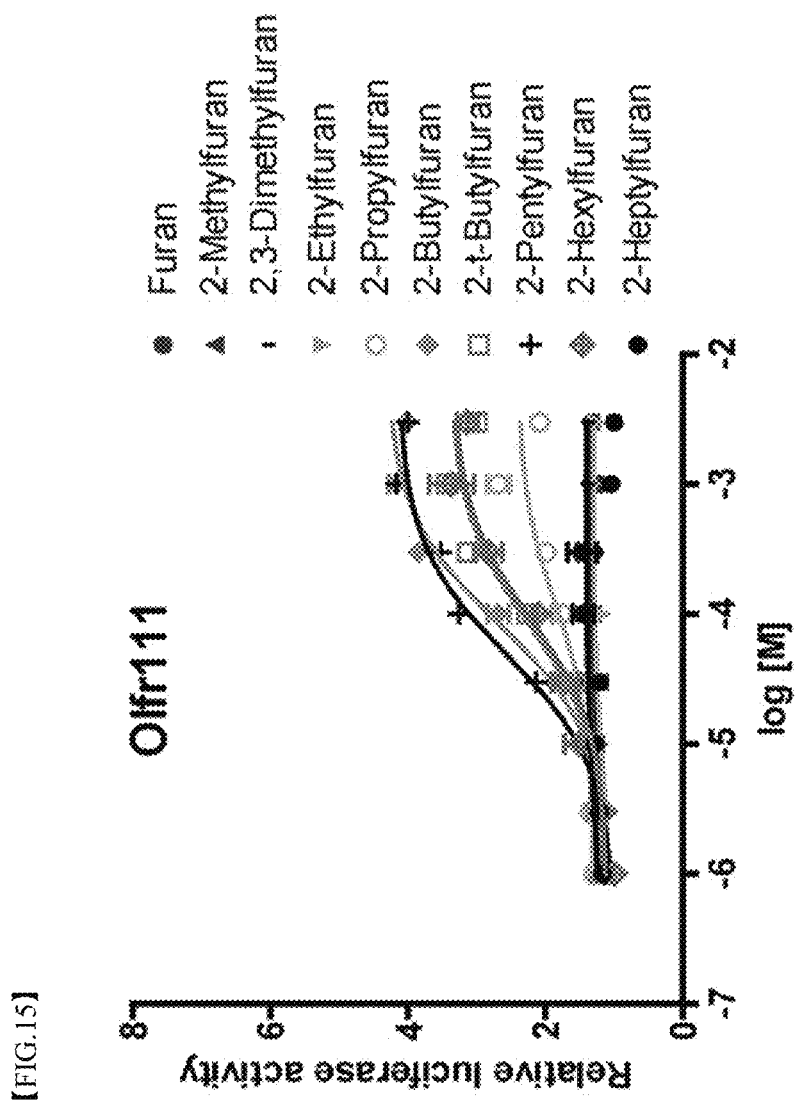
[FIG.15]

[FIG.16]
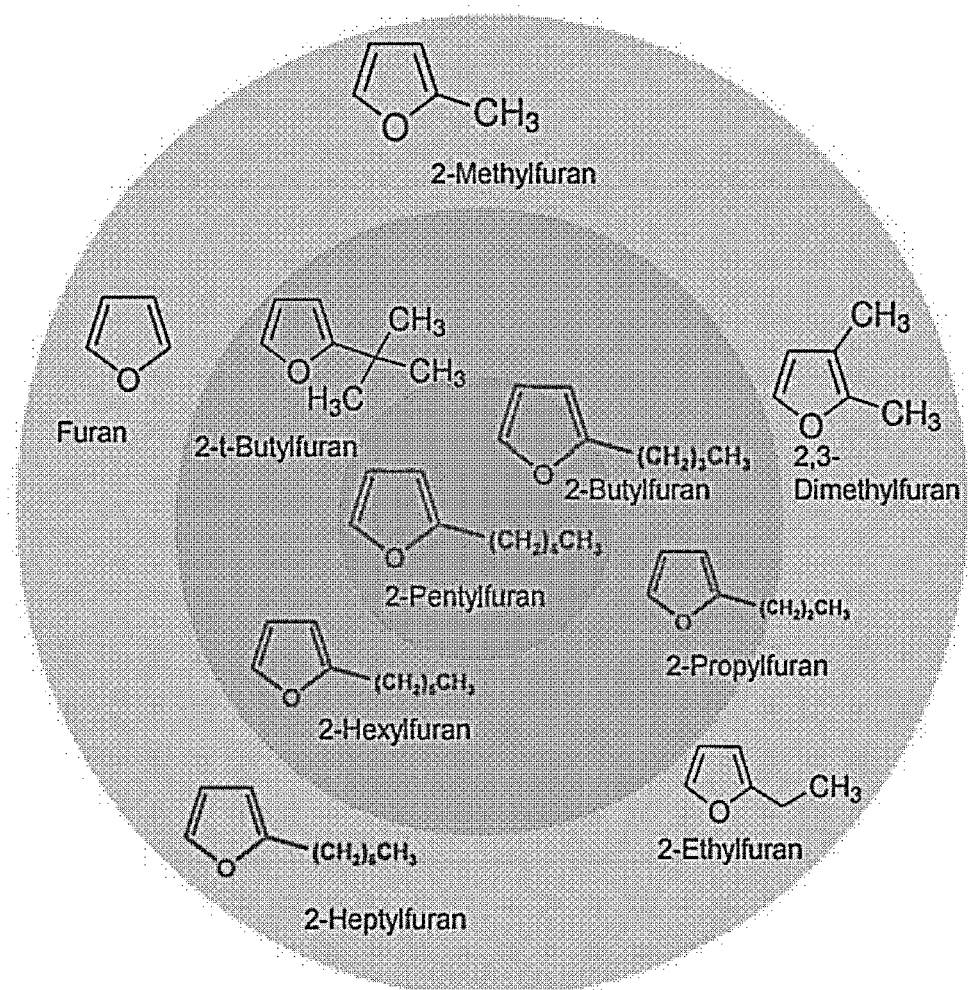

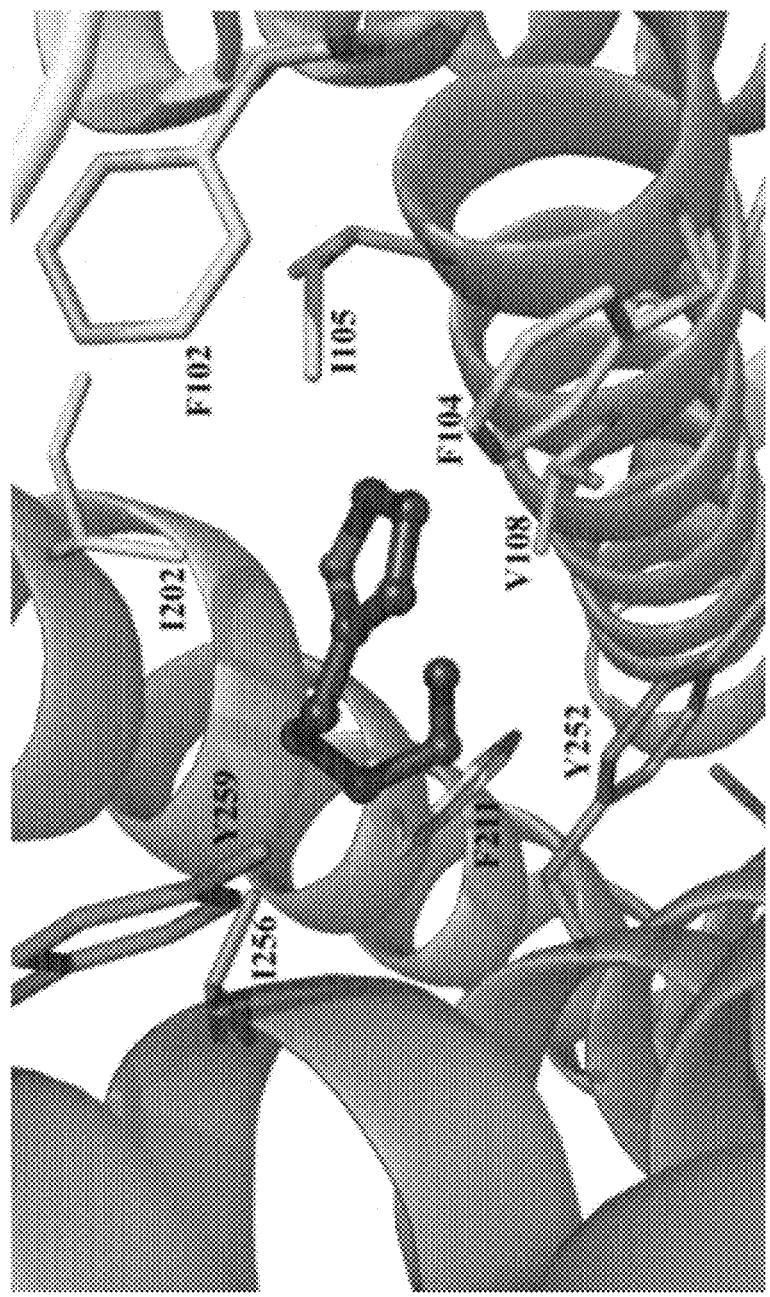
[FIG.17]

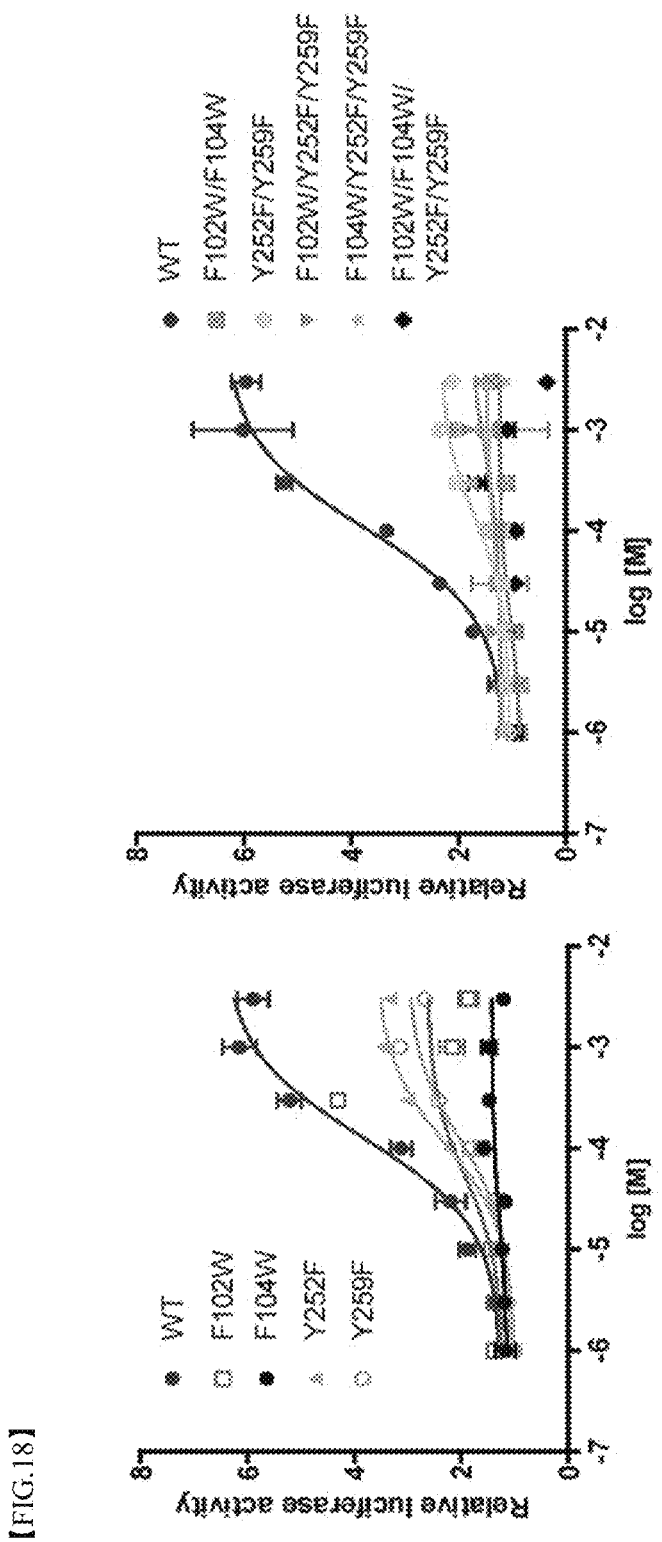
[FIG.18]

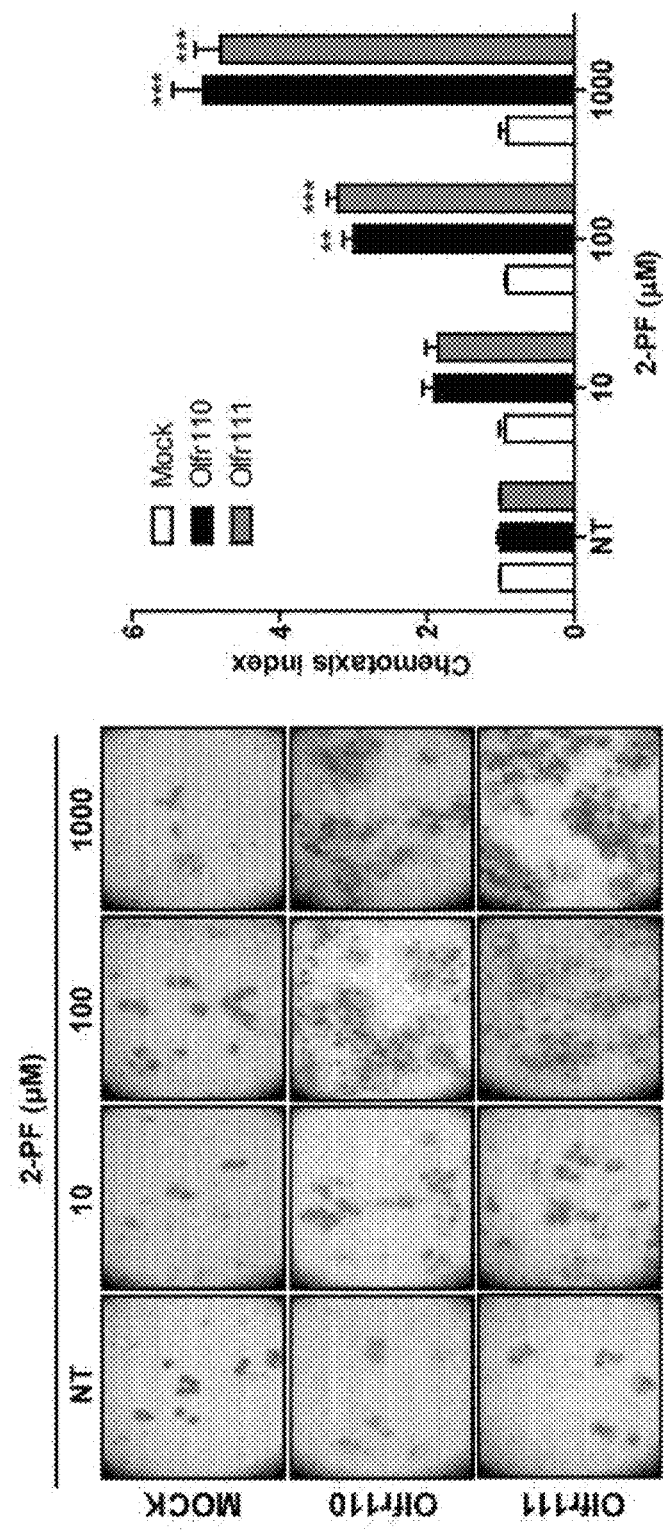
[FIG.19]

【FIG.20】
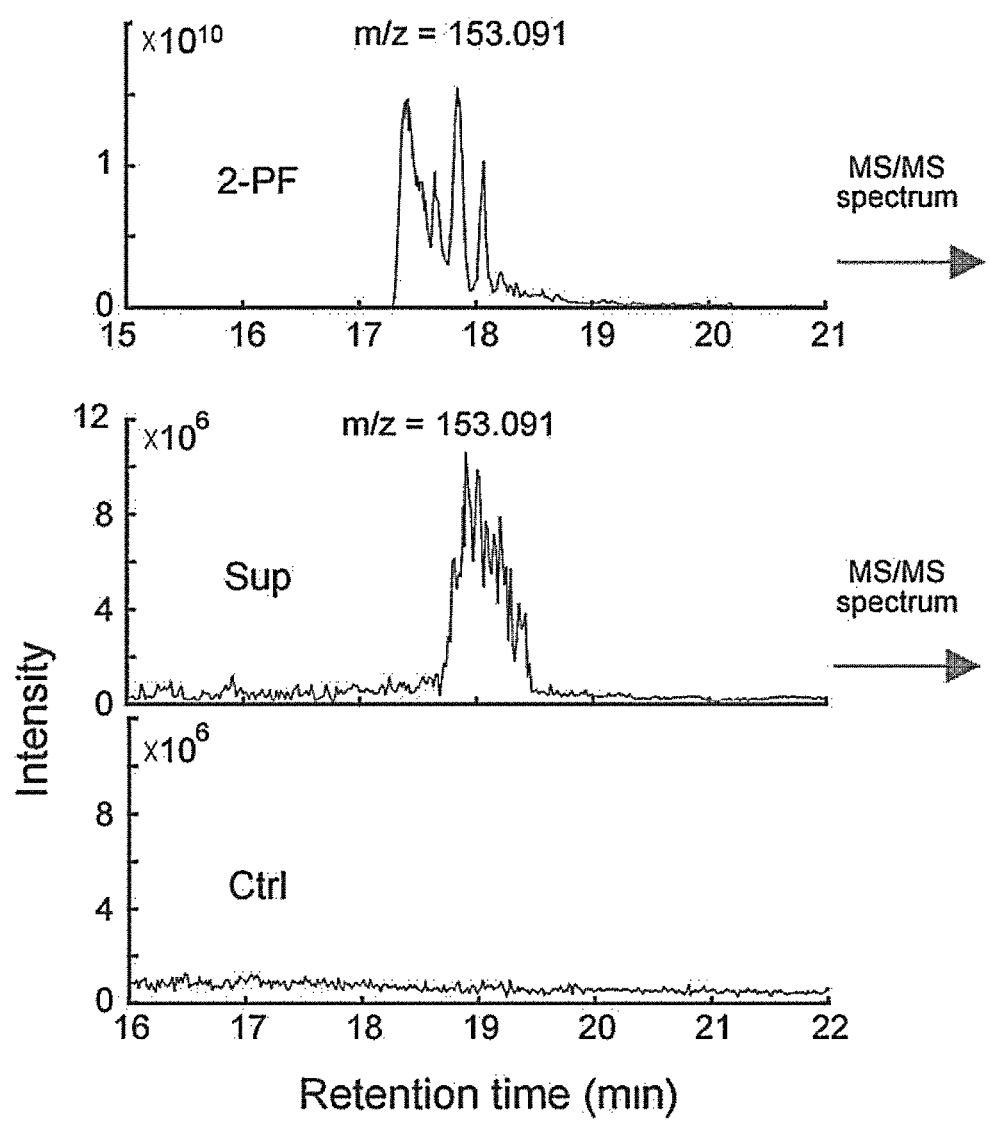

[FIG.21]
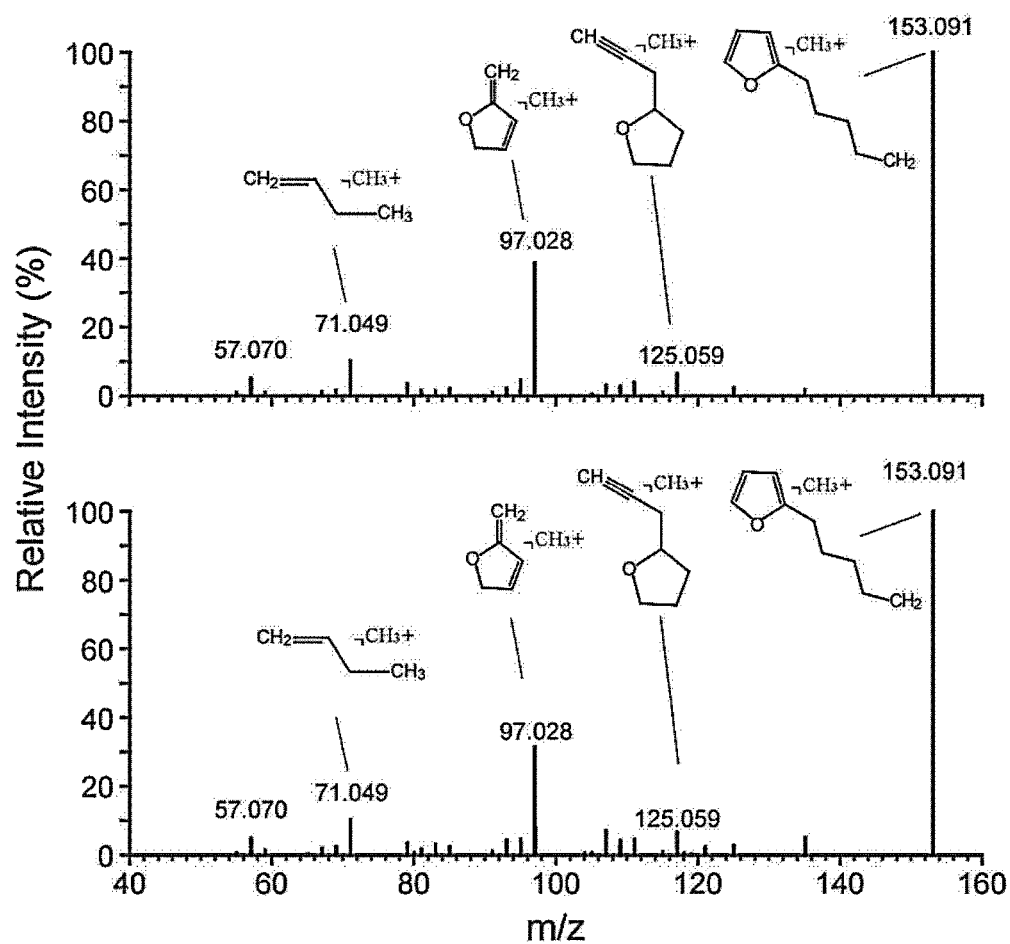

[FIG.22]
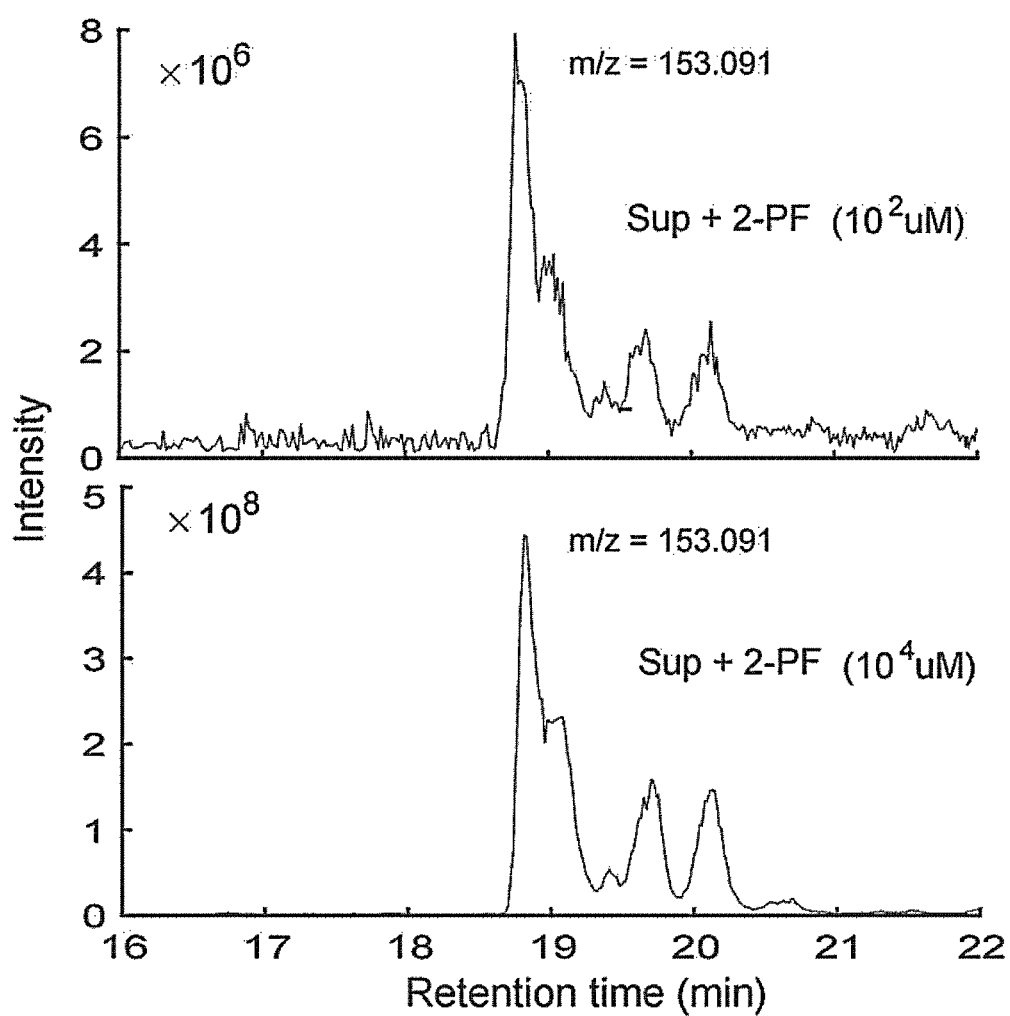

[FIG.23]
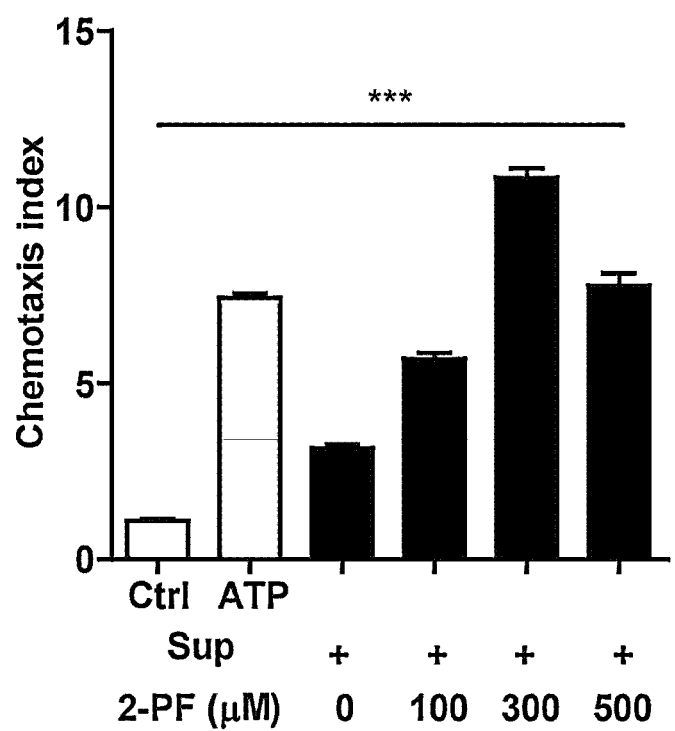

[FIG.24]
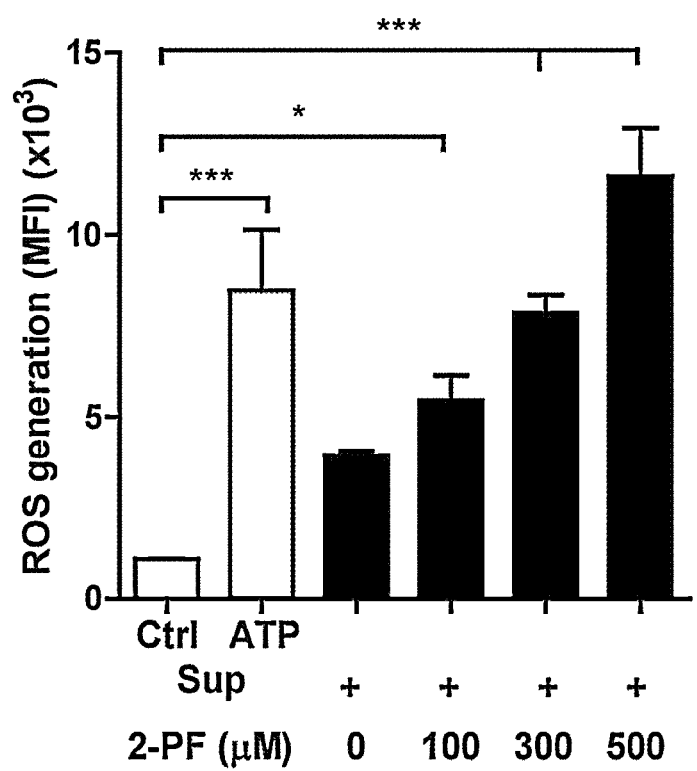

[FIG.25]
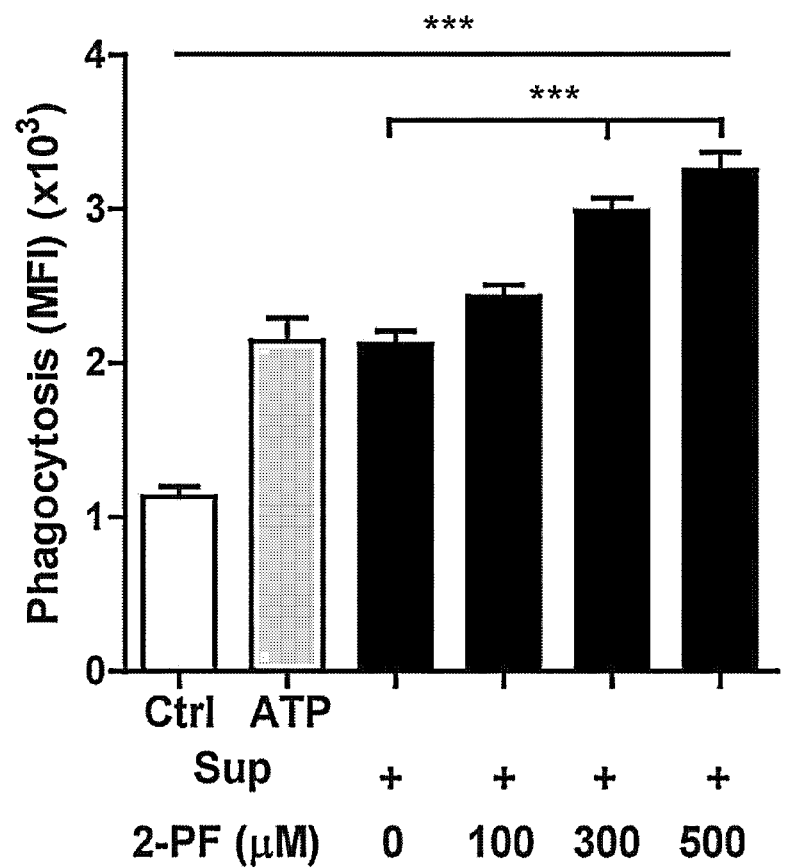

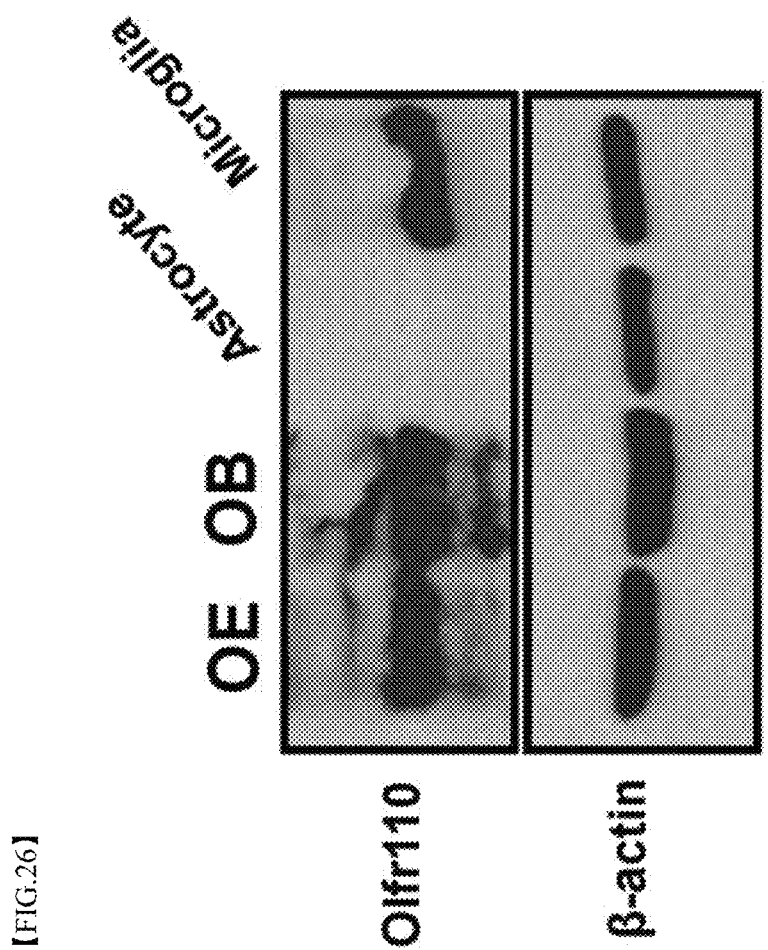
[FIG.26]

[FIG.27]
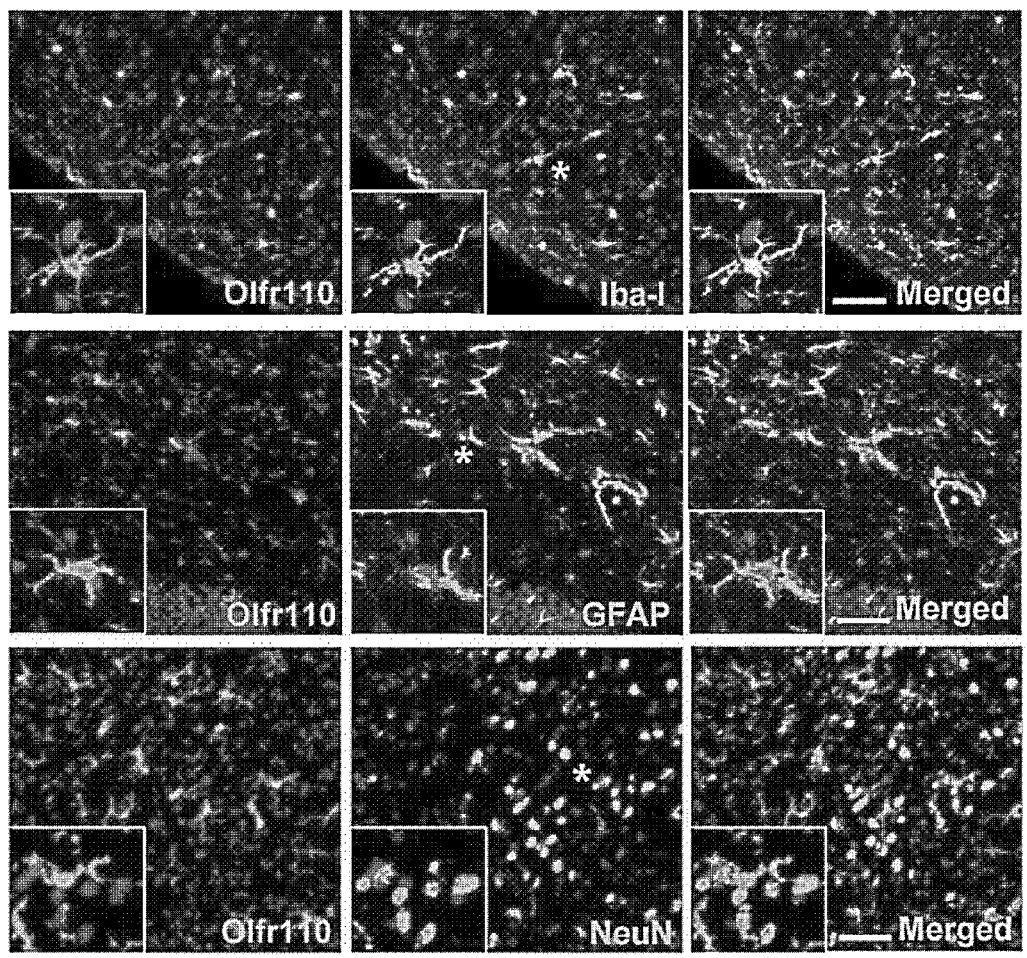

[FIG.28]
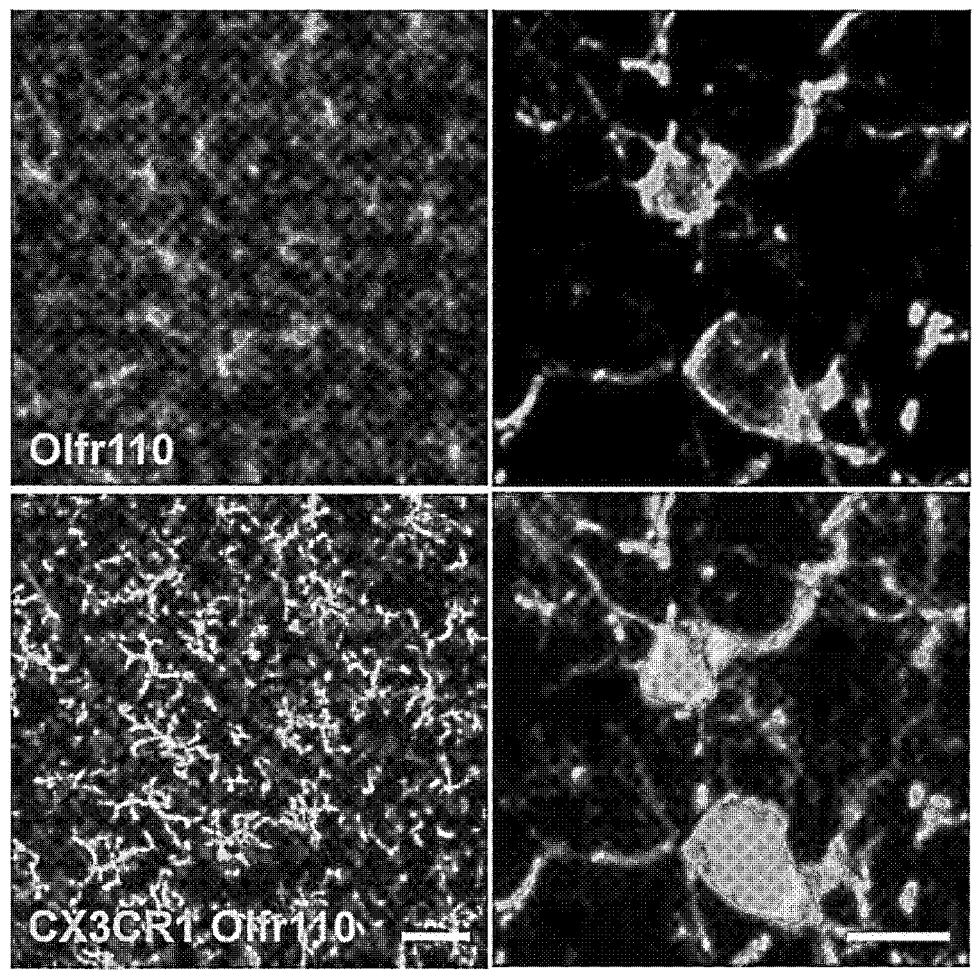

[FIG.29]
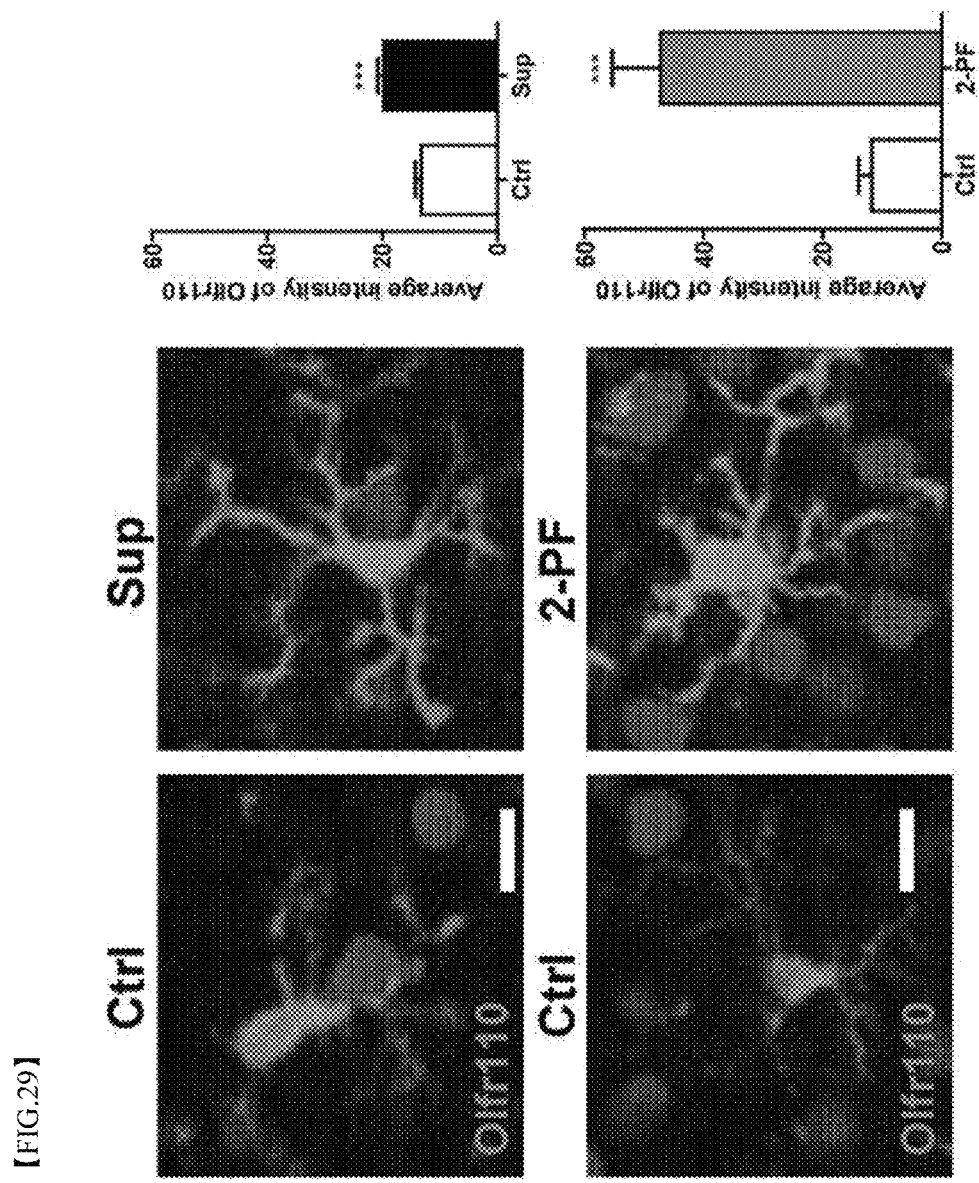

[FIG.30]
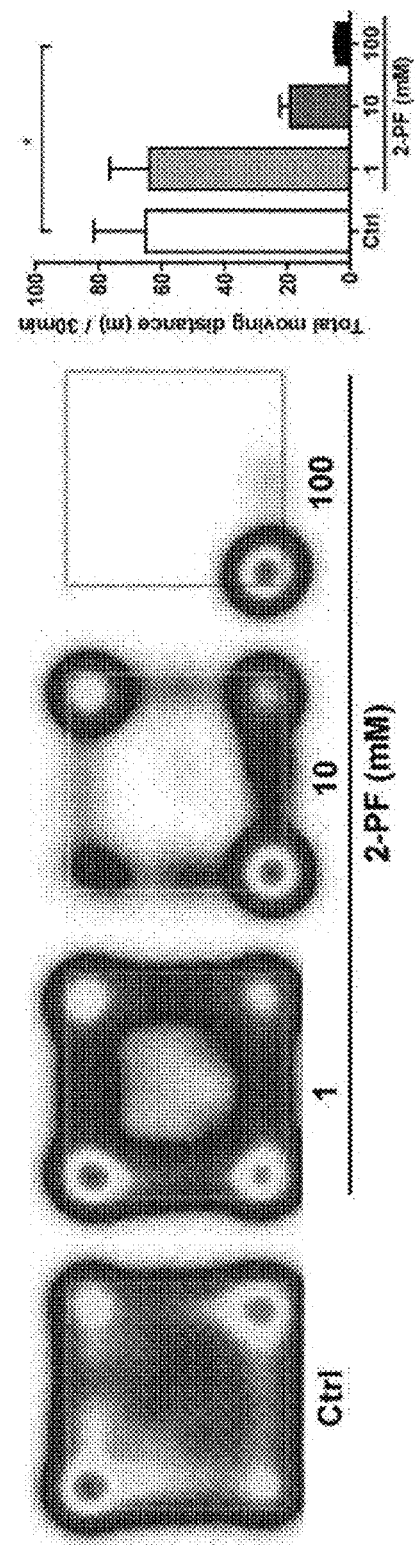

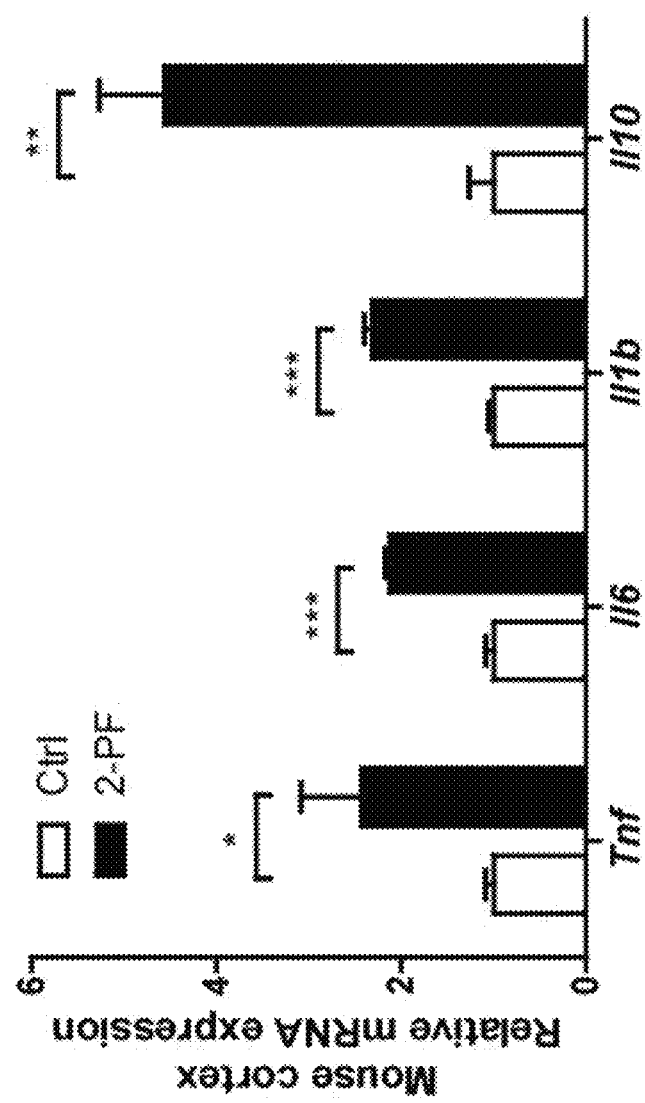
[FIG.31]

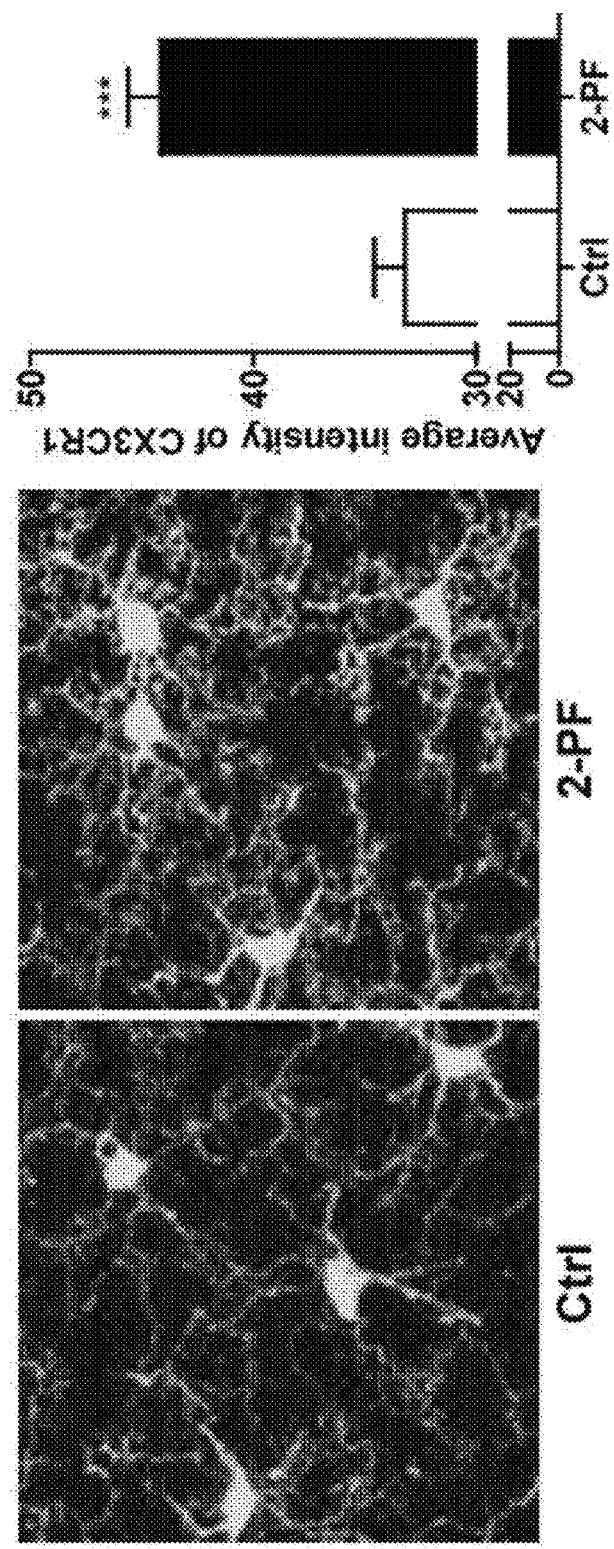
[FIG.32]

[FIG.33]
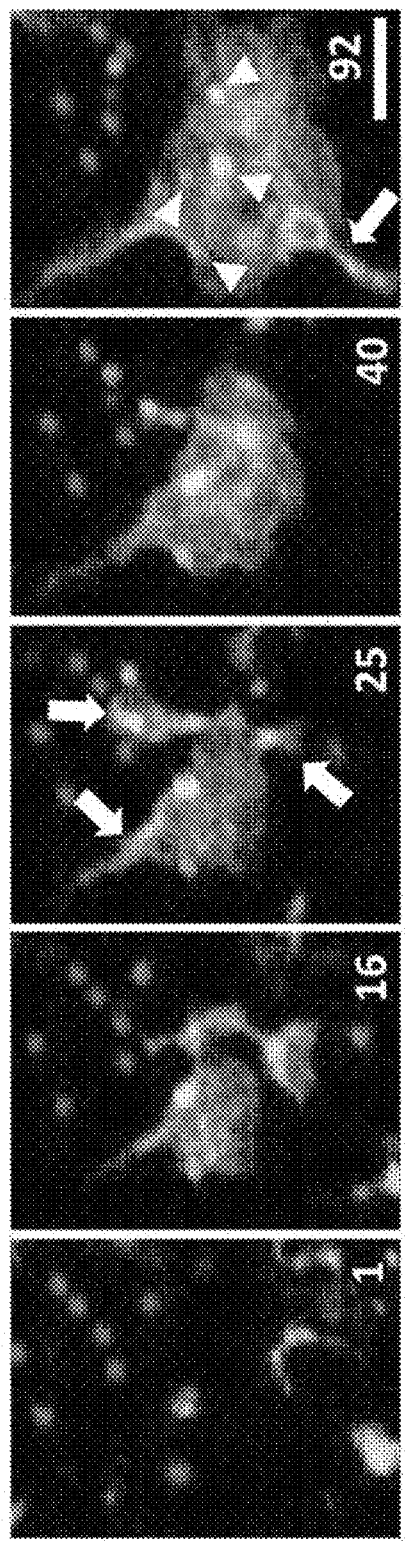
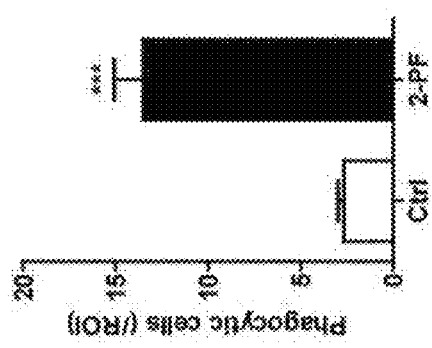

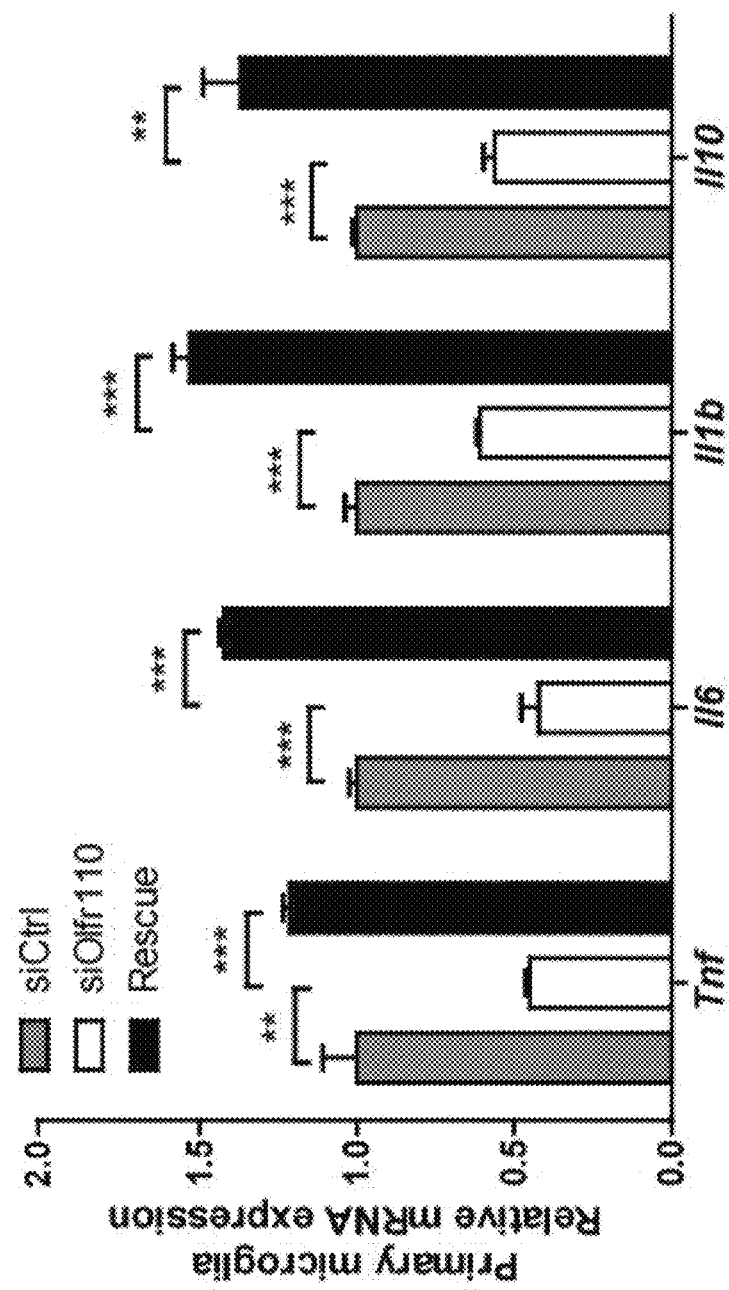
[FIG. 34]

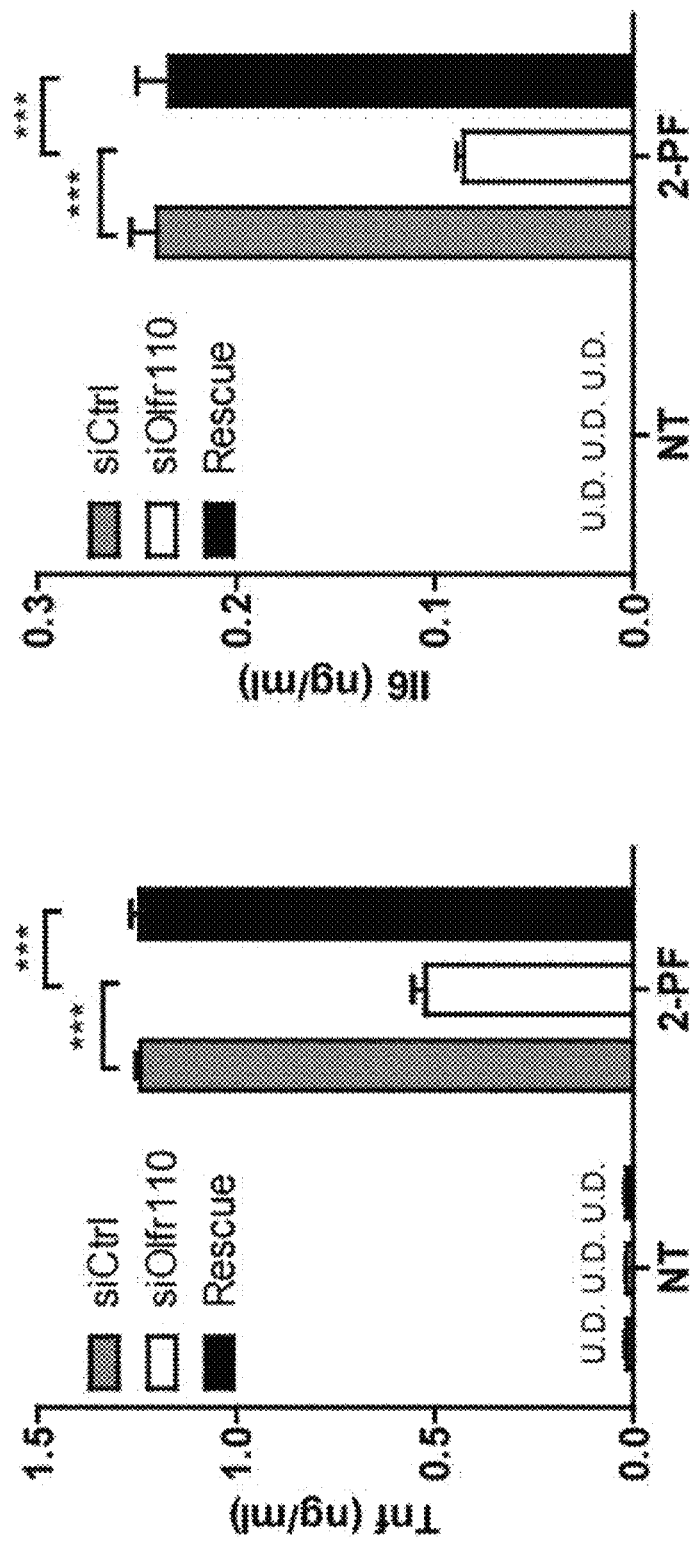
[FIG.35]

[FIG.36]
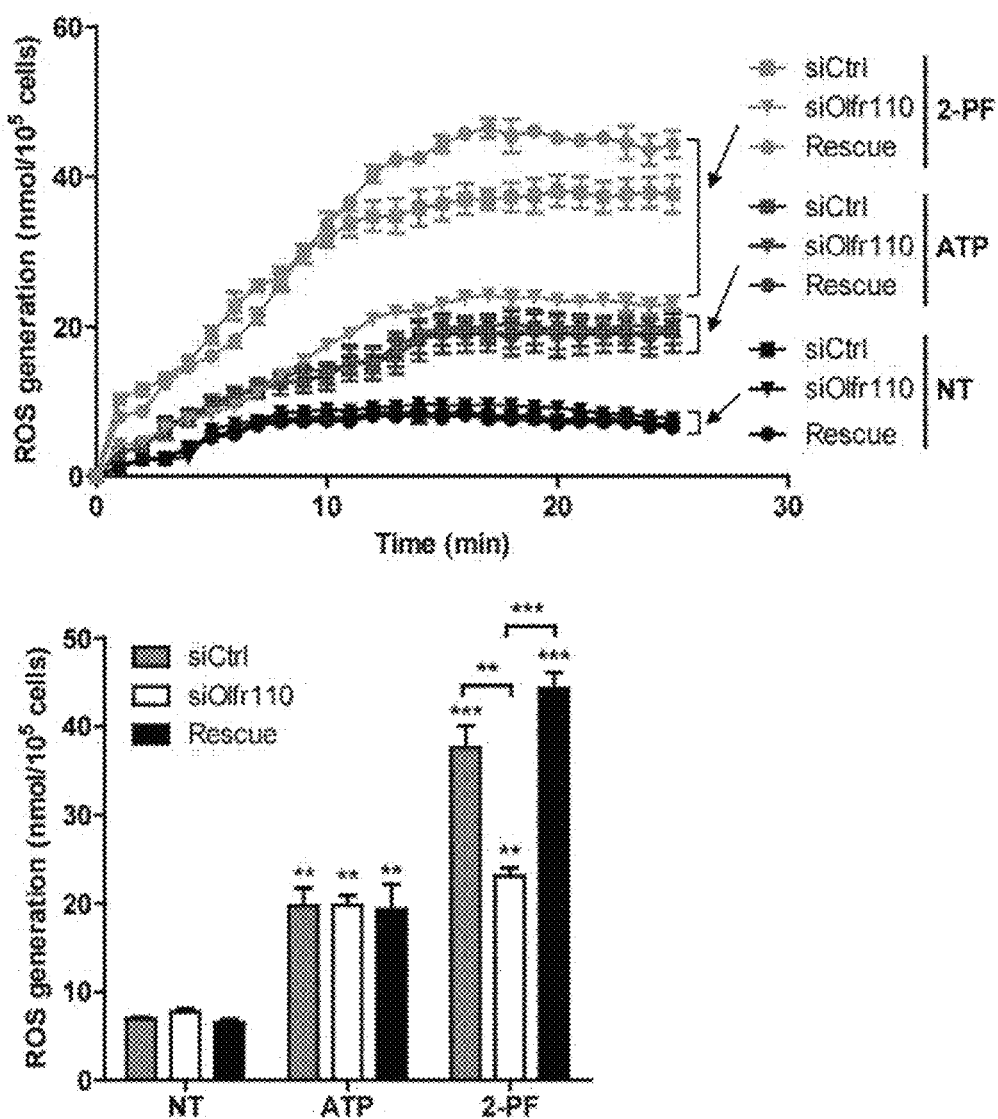

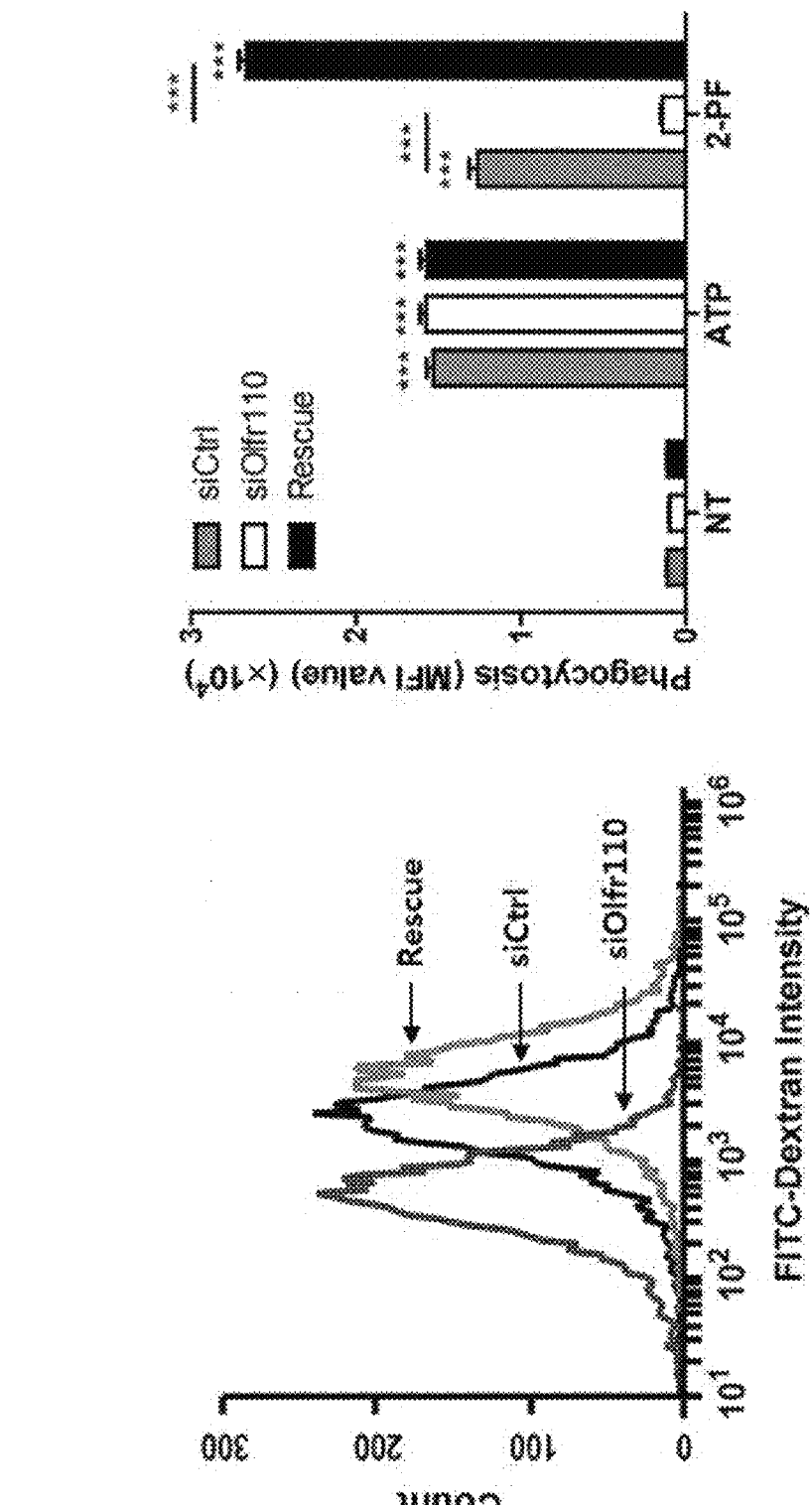
[FIG.37]

[FIG.38]
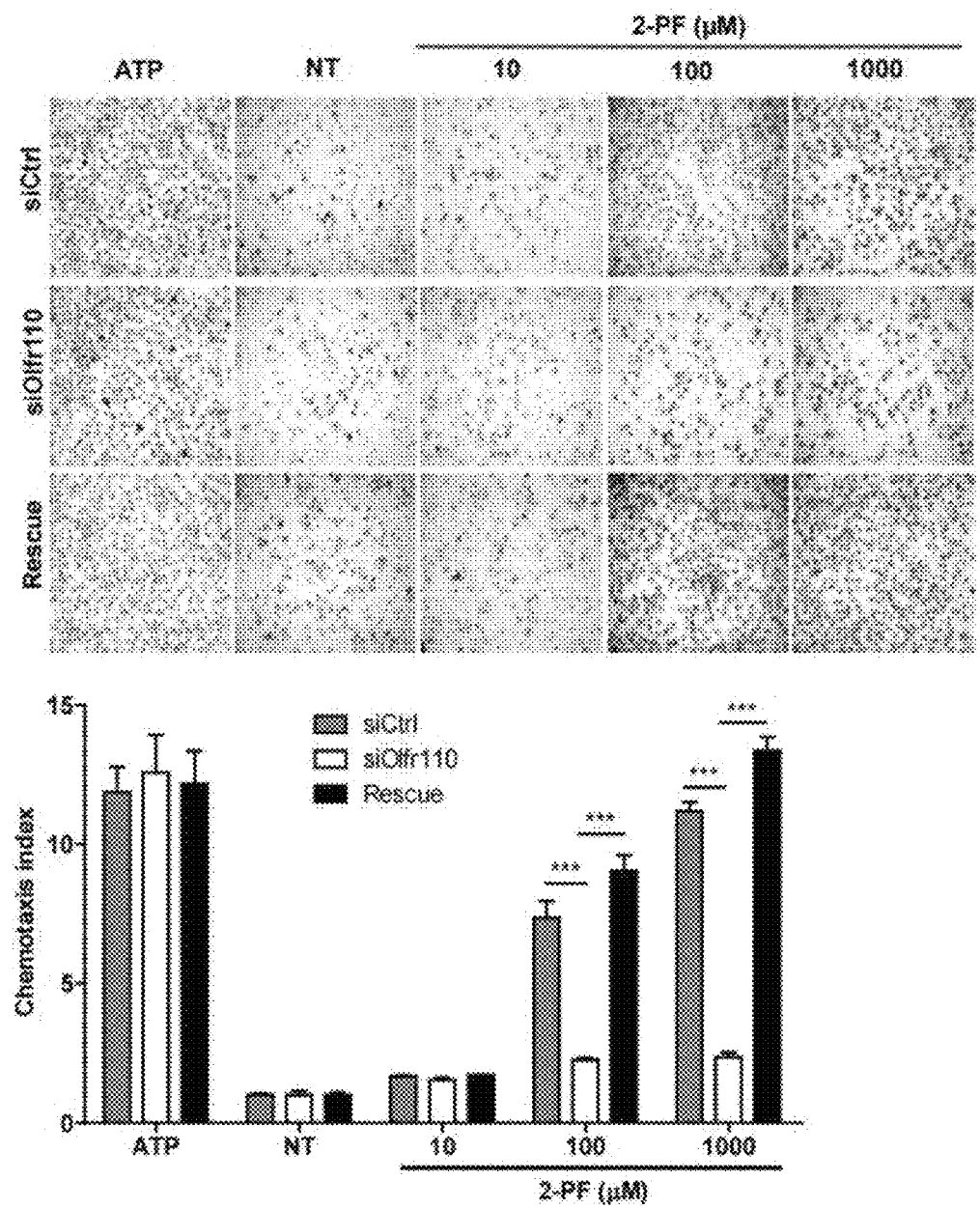

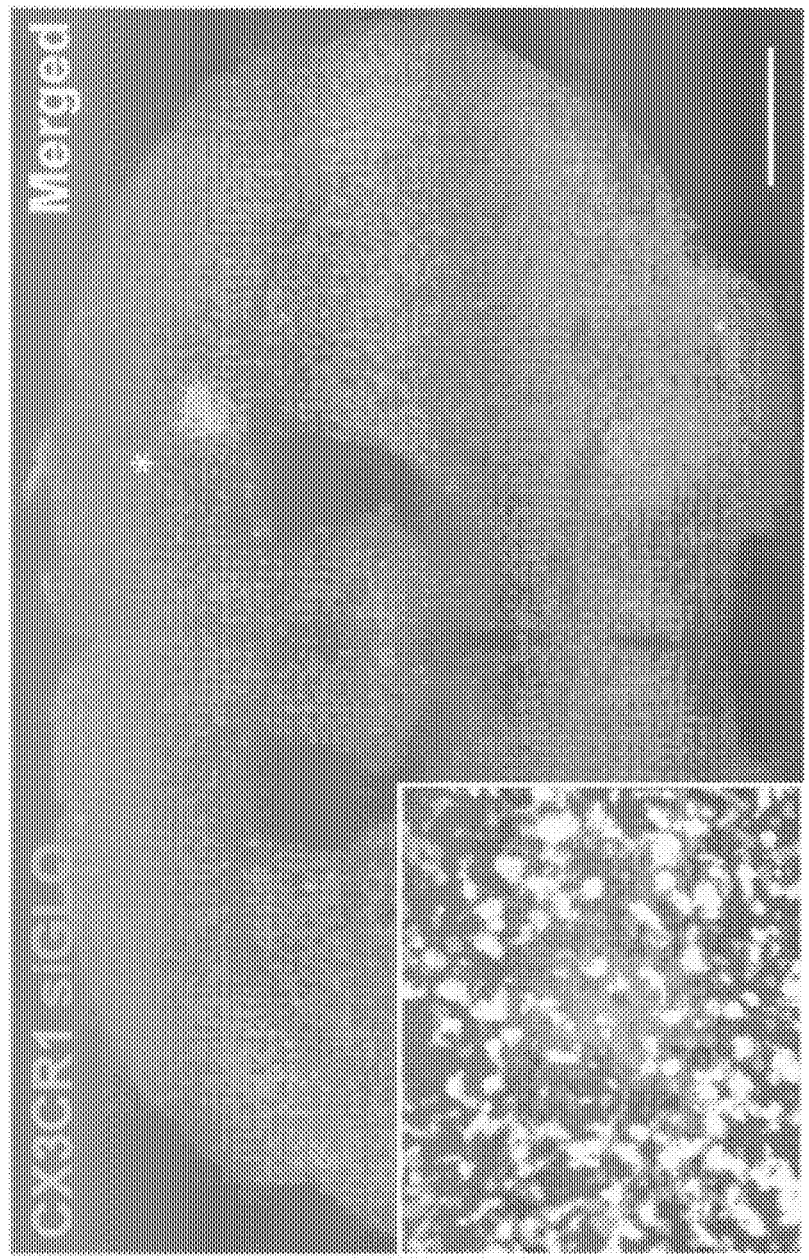
[FIG.39]

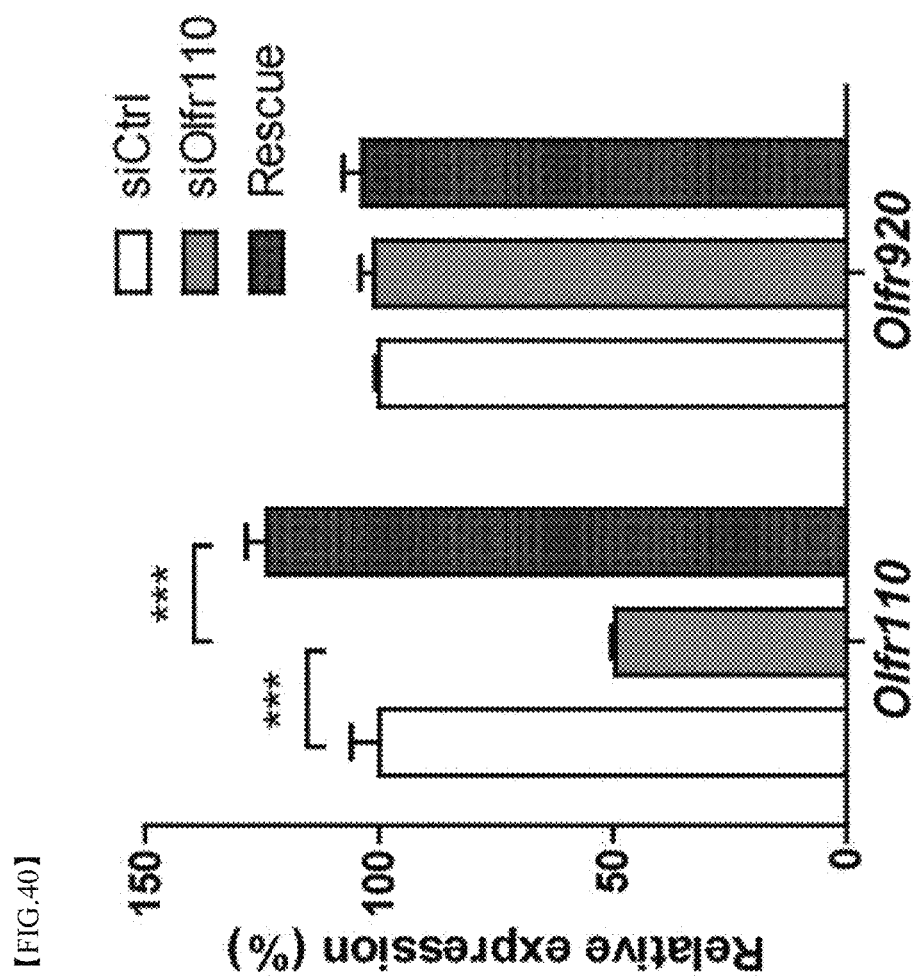
[FIG.40]

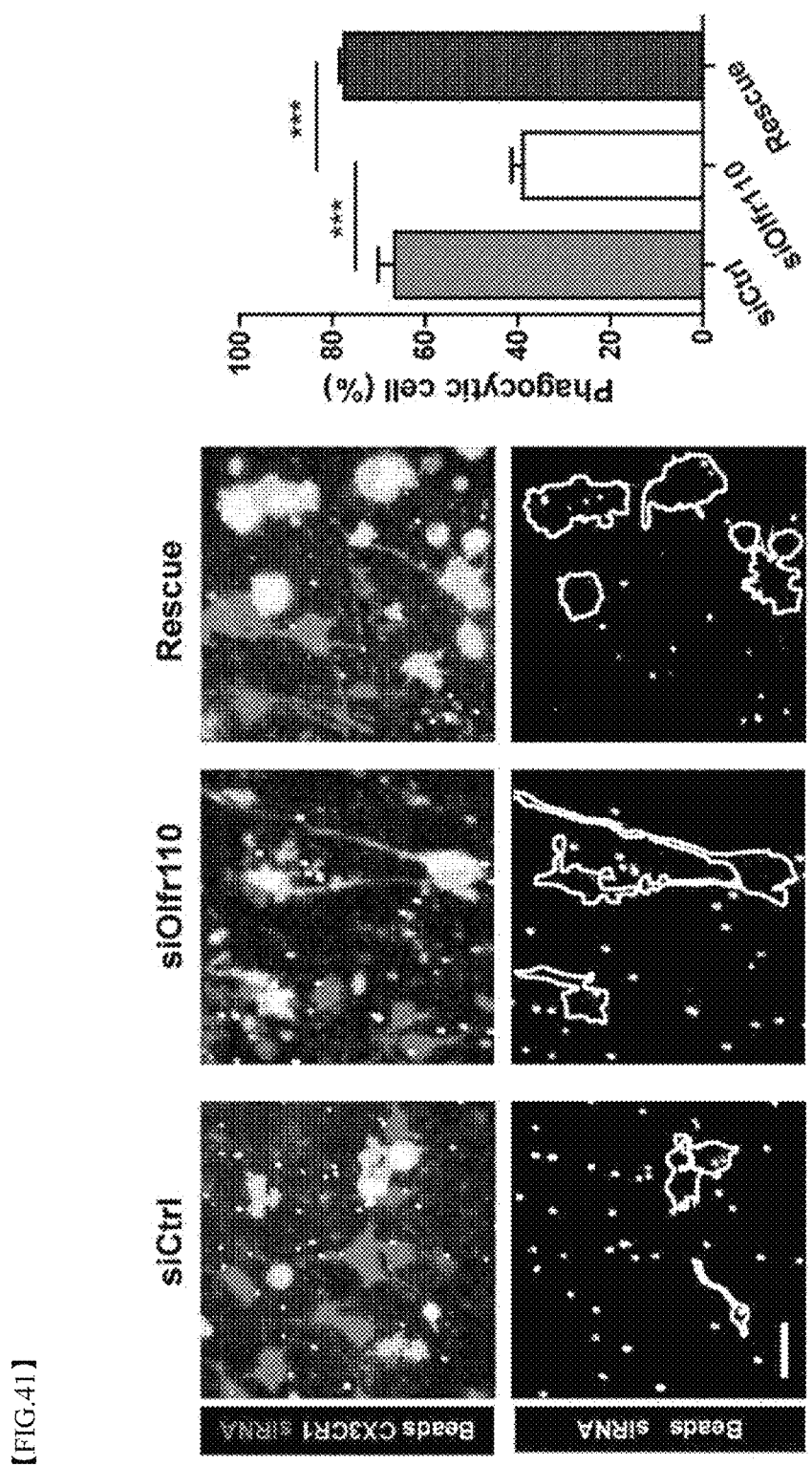
[FIG.41]

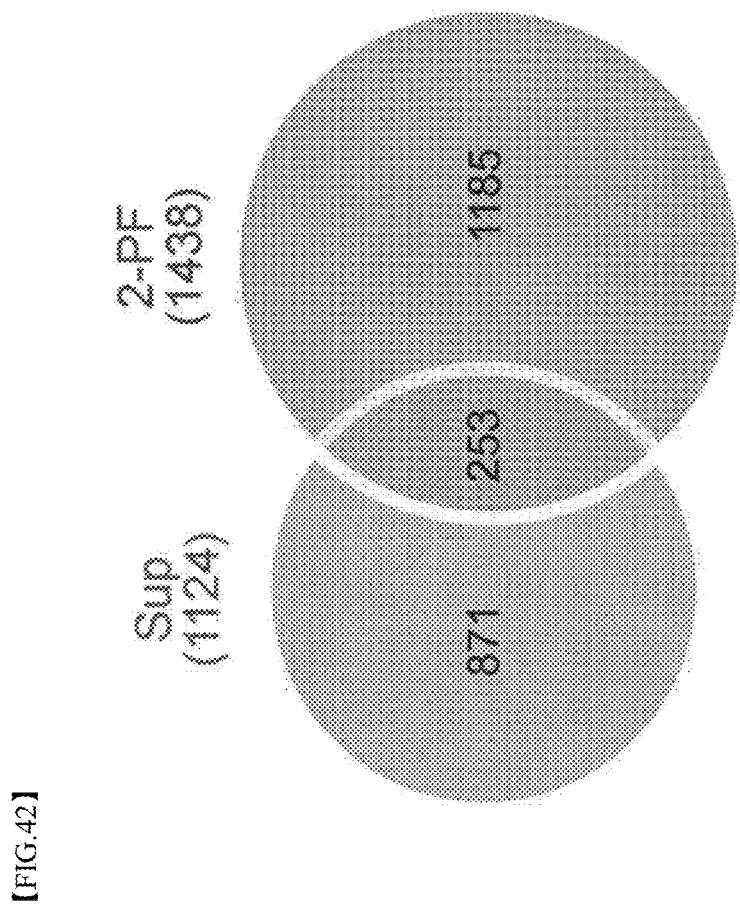
[FIG.42]

[FIG.43]
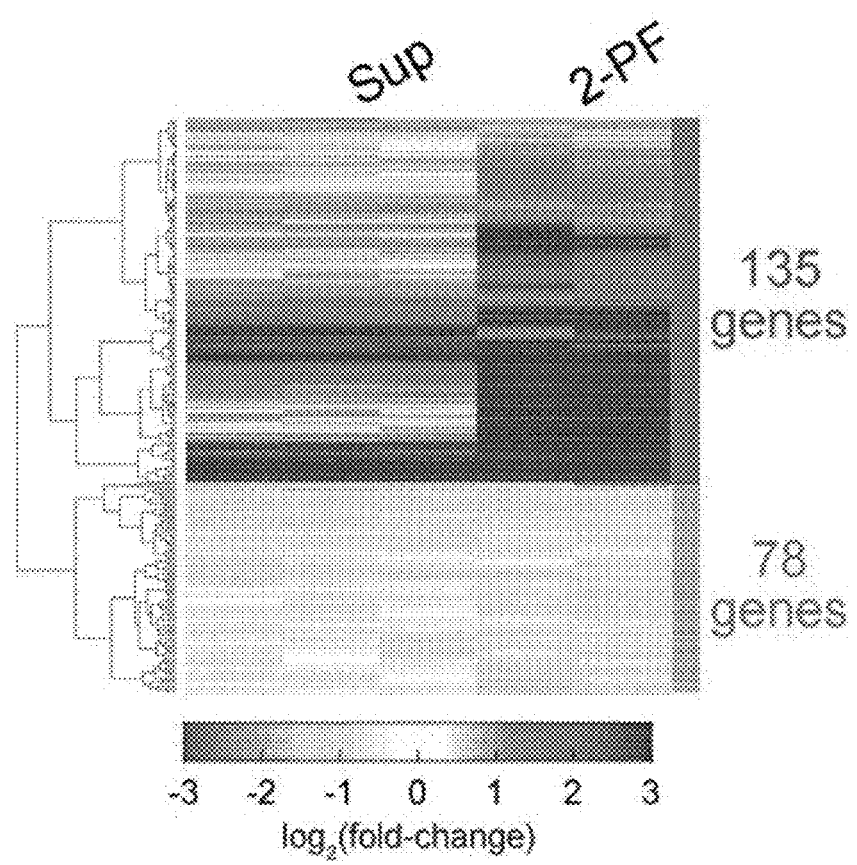

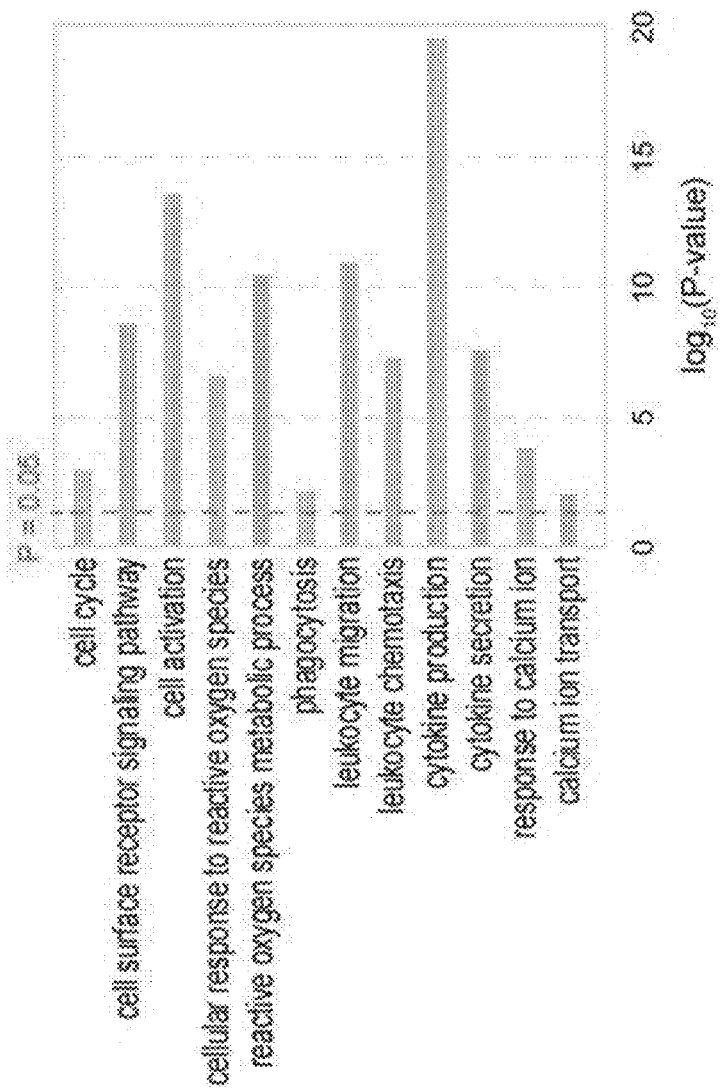
[FIG.44]

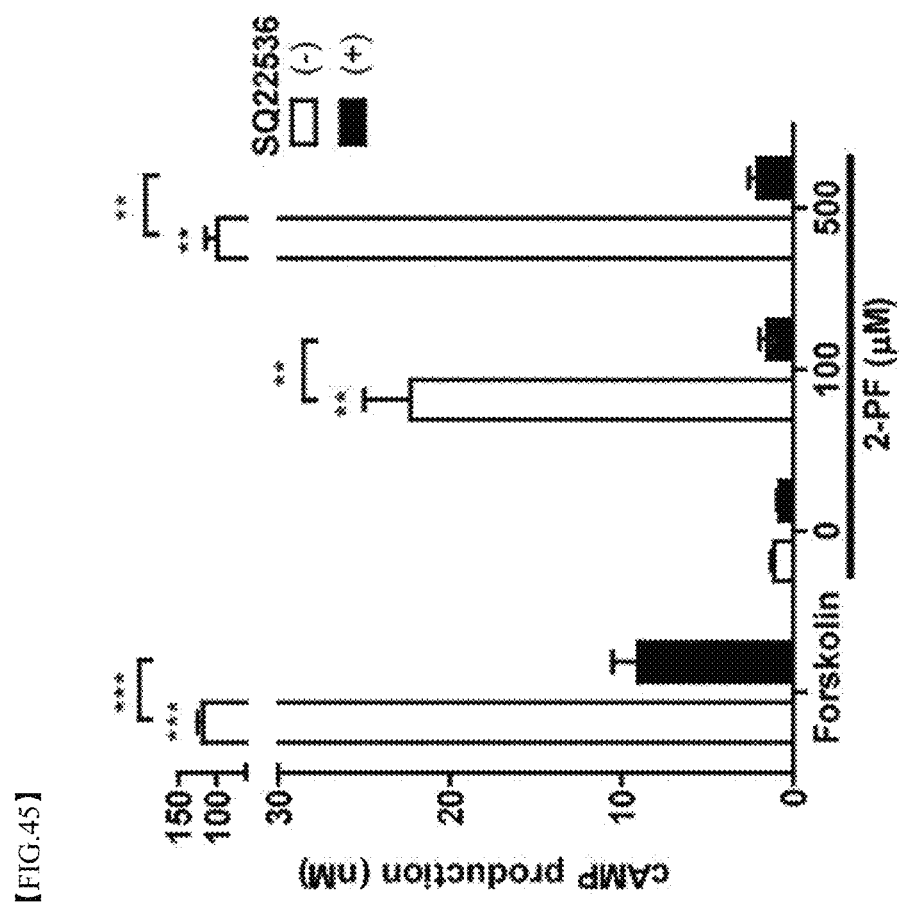
[FIG.45]

[FIG.46]
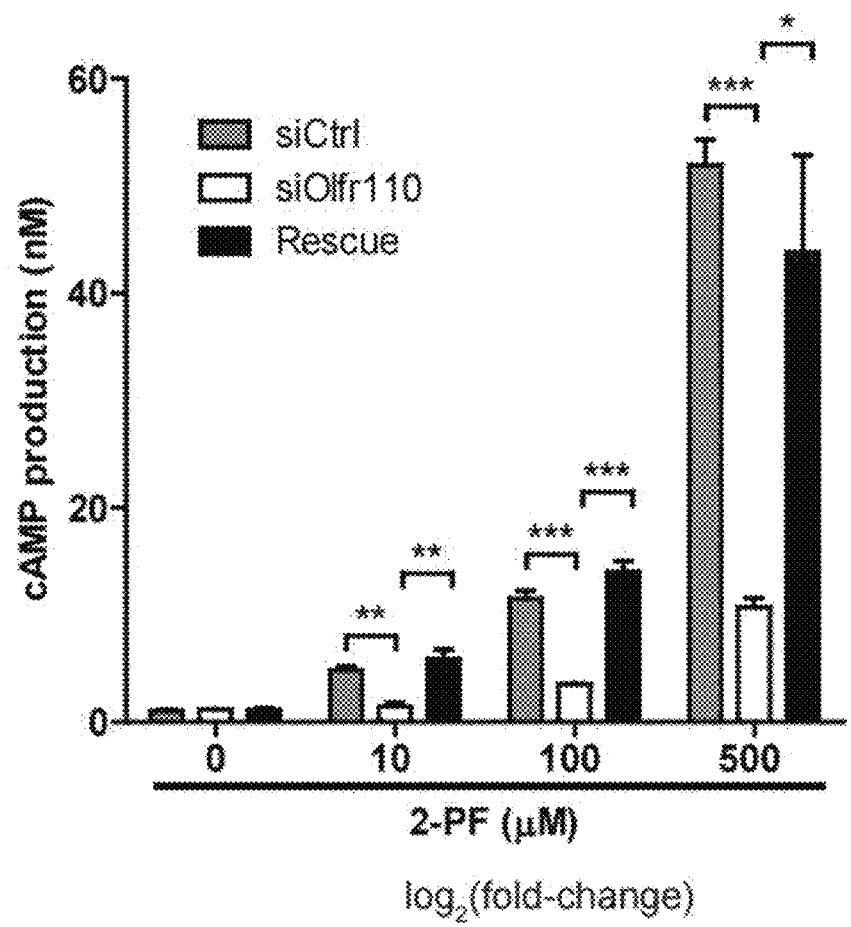

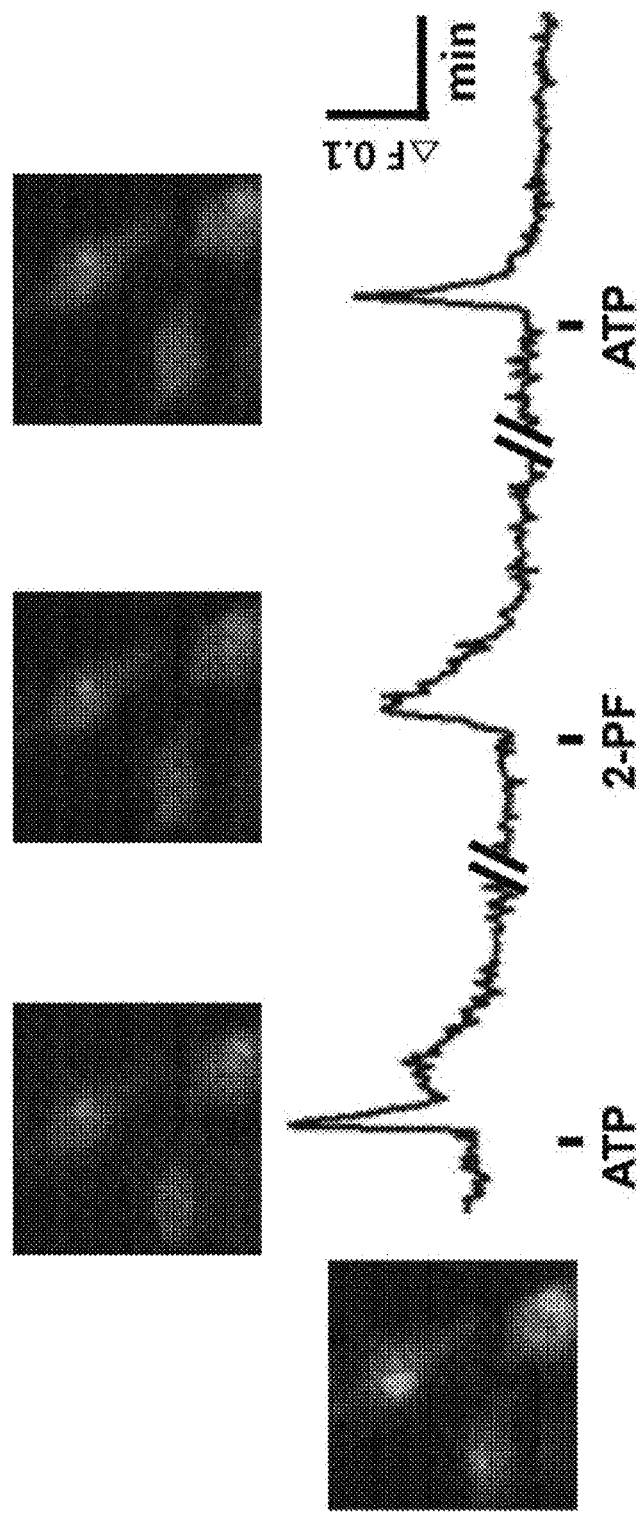
[FIG.47]

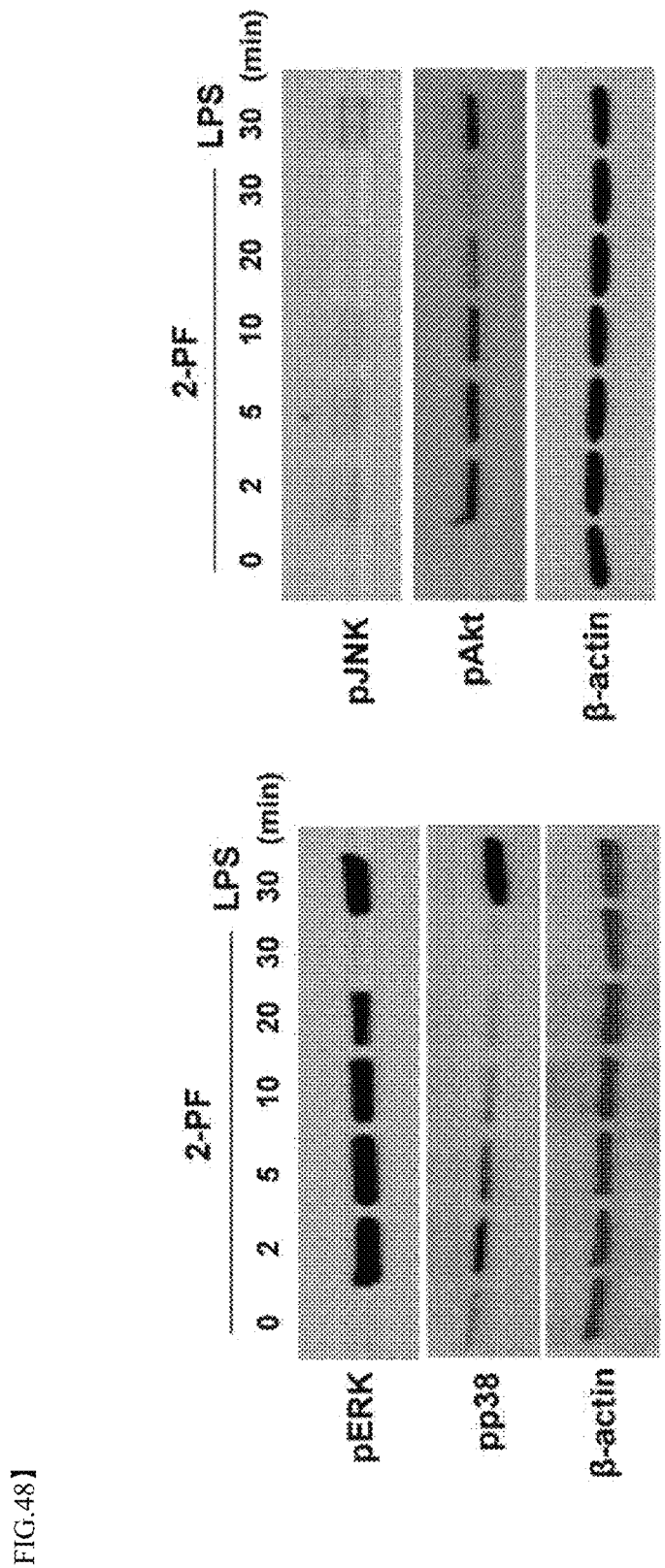
[FIG.48]

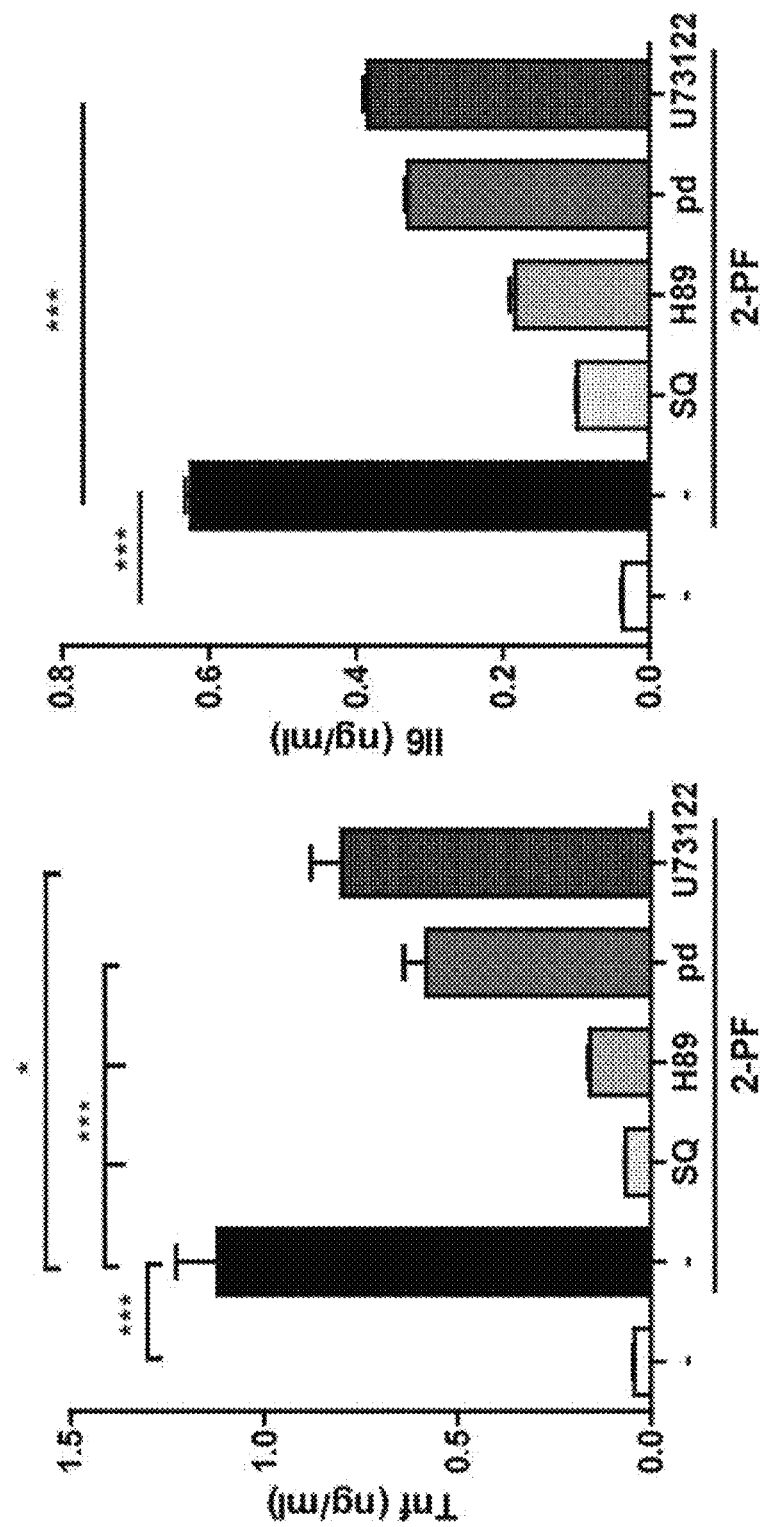
[FIG.49]

[FIG.50]
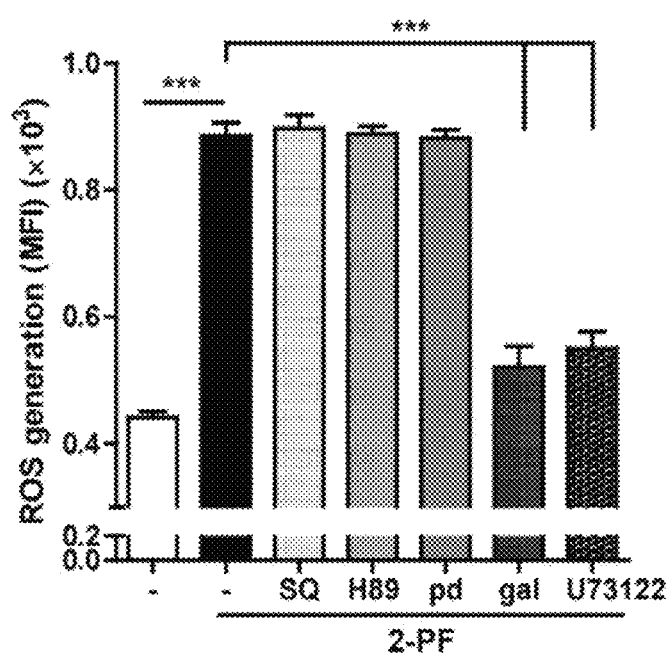

[FIG.51]
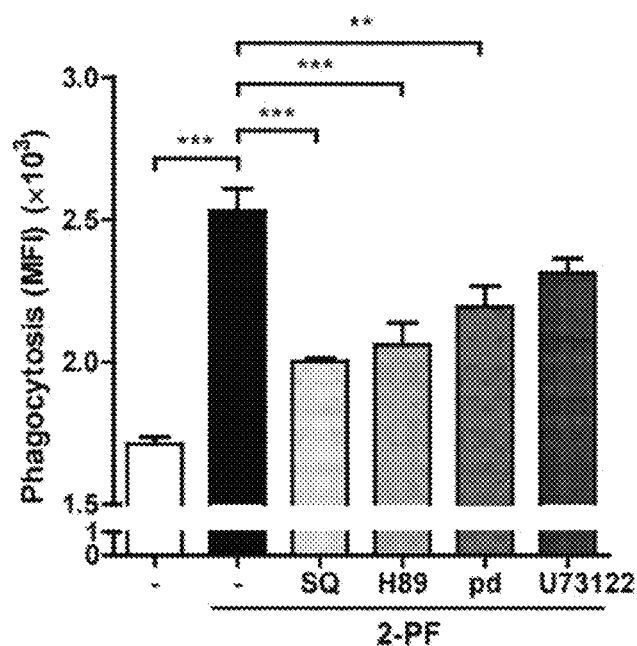

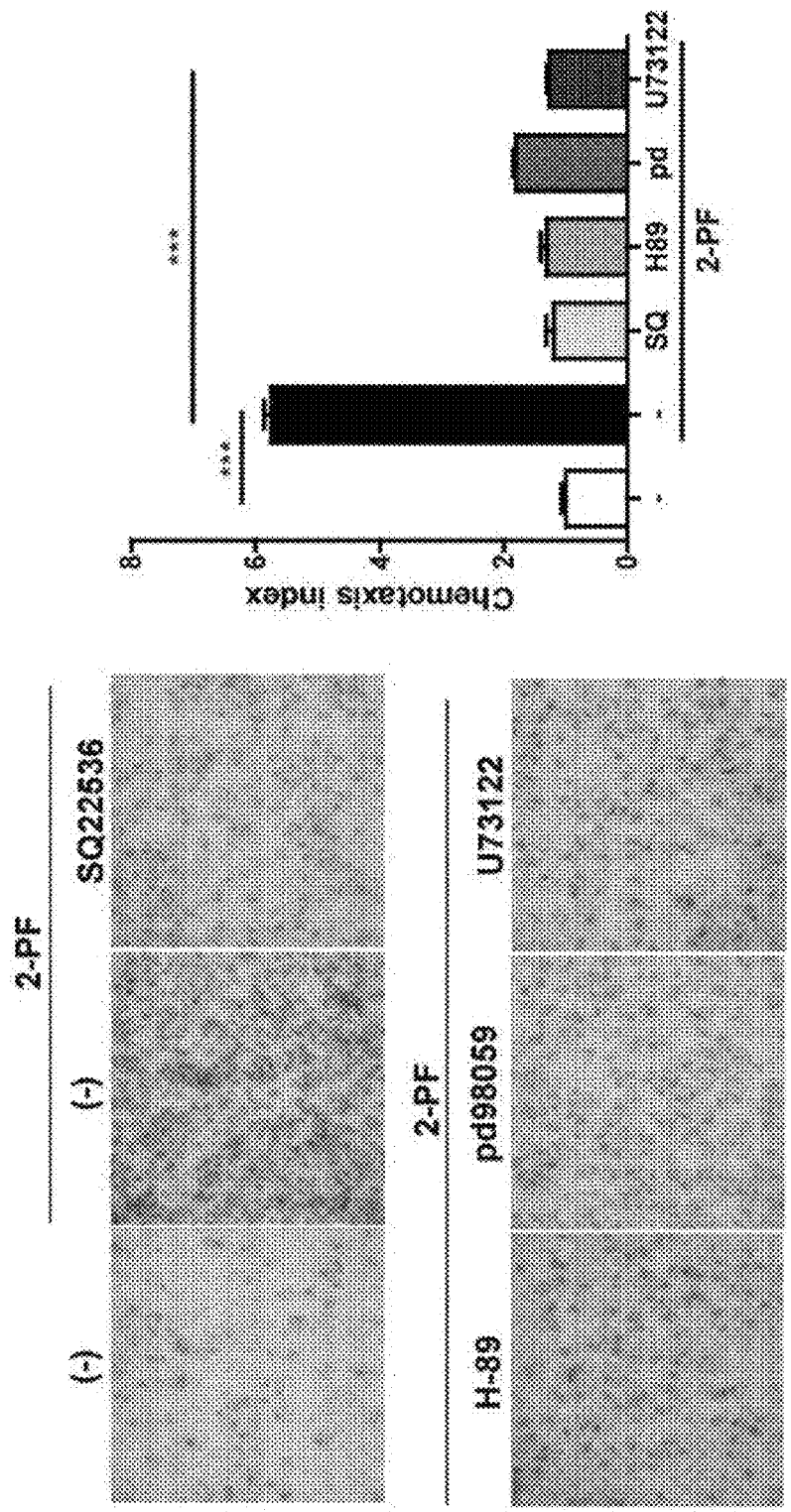
[FIG.52]

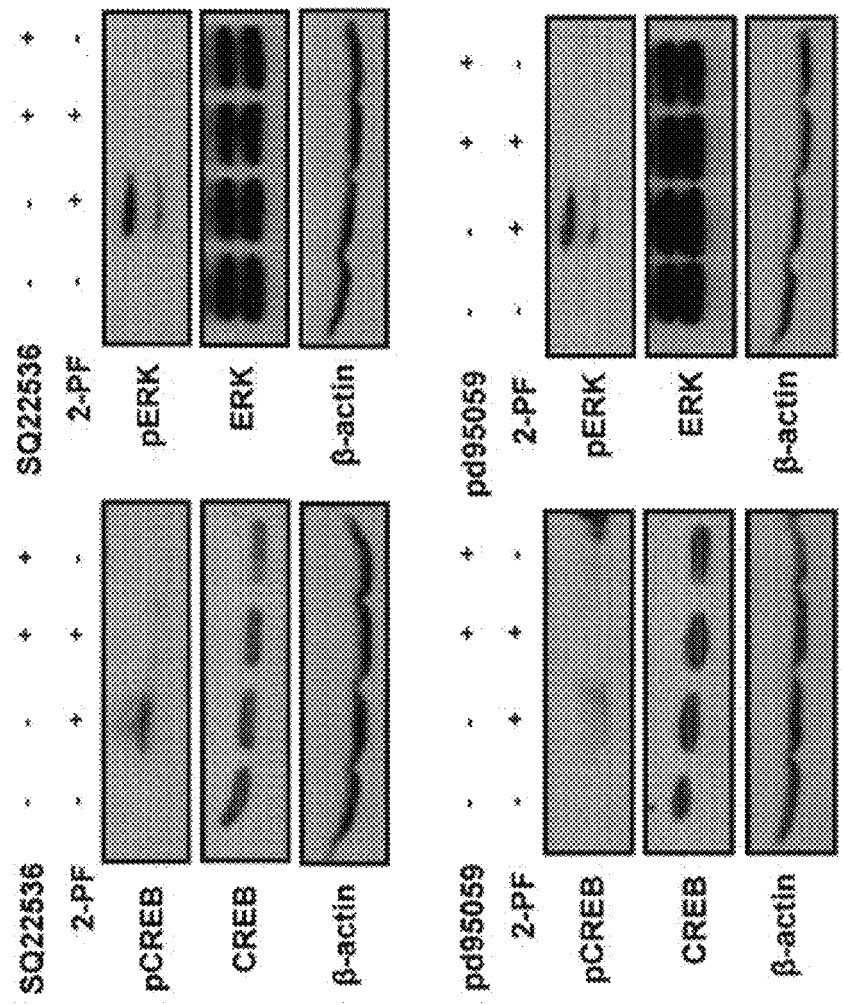
[FIG.53]

[FIG.54]
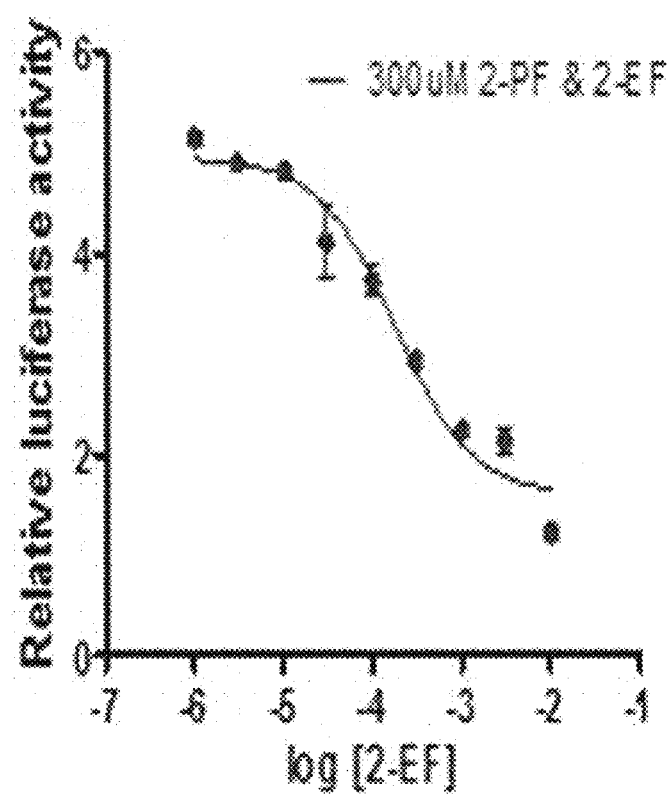

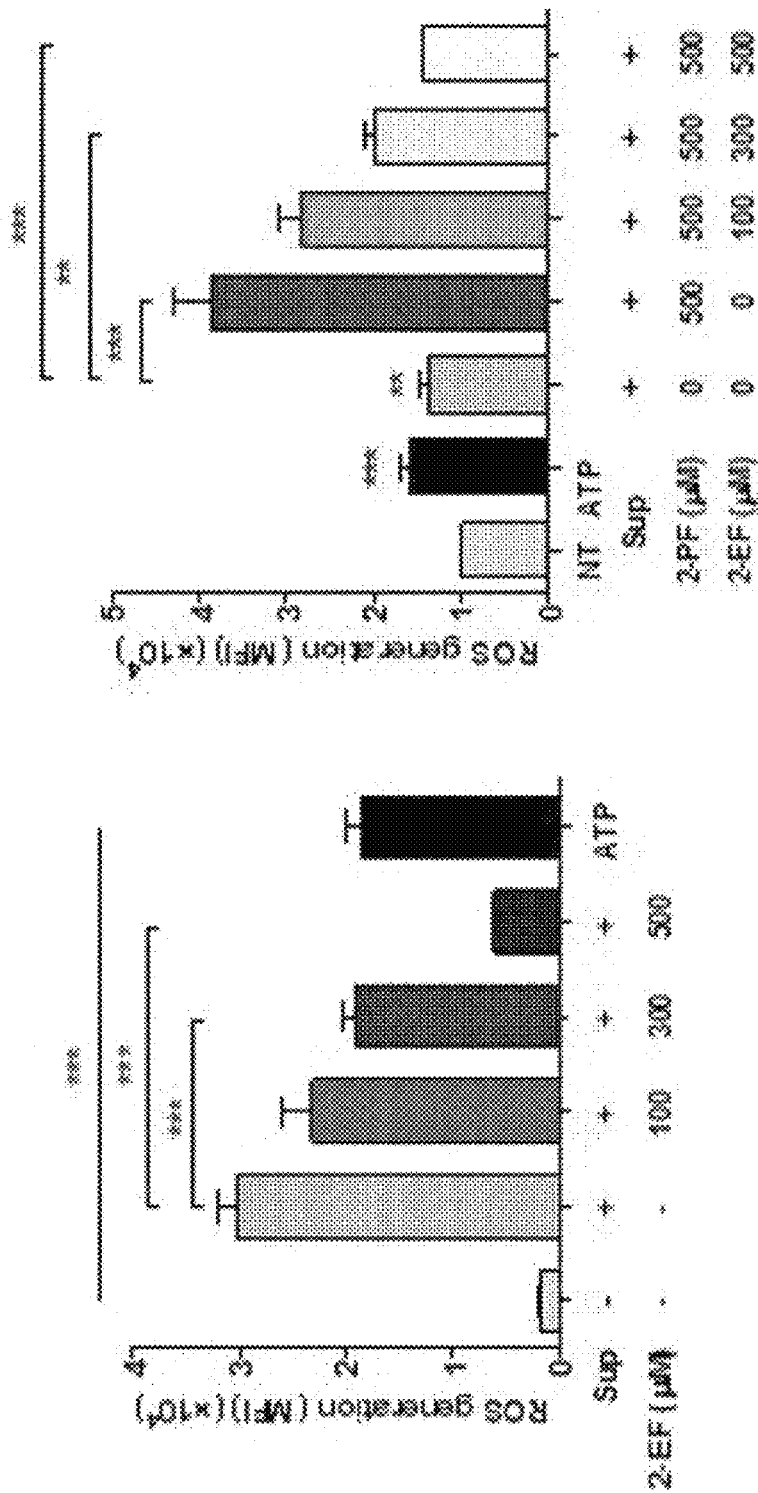
[FIG.55]

OLFACTORY RECEPTOR AS MICROGLIA MARKER AND USE THEREOF

CROSS-REFERENCE TO RELATED APPLICATIONS

This application is a national phase under 35 U.S.C. § 371 of PCT International Application No. PCT/KR2020/008344 which has an International filing date of Jun. 26, 2020, which claims priority to KR Application No. 10-2019-0077256, filed Jun. 27, 2019, the entire contents of each of which are hereby incorporated by reference.

TECHNICAL FIELD

The present invention relates to an odorant receptor as a microglia marker and a use thereof.

BACKGROUND ART

Biologically, small molecules that are secreted by intestinal microbes and are active are called metabolites, and play a role in mediating interactions between a host and microbes (Blacher et al., 2017; Nicholson et al., 2012). More specifically, metabolites, for example, niacin (NA), acetate, propionate, and small chain fatty acids (SCFAs) such as butyrate, secreted in the intestines, are known to regulate an inflammatory response of T cells or inflammatory responses of neutrophils and macrophages and to deeply affect the immune system of a host (Topping and Clifton, 2001). SCFAs derived from these intestinal microbes regulate a signal from the intestinal microbes to the brain called the gut-brain axis (Erny et al., 2015). Moreover, in addition to the symbiotic microorganisms in the intestines, the organs in our body also send signals when a host is infected with a pathogen, and more specifically, infection sources such as intestinal microbes secrete and modify metabolites capable of affecting host immunity, called the pathogen-brain axis (Topping and Clifton, 2001). However, the pathogen-brain axis has been rarely studied.

Microglia are involved in important immune cell activity in the pathogen-brain axis. They play a critical role against infection by pathogens (Hanisch and Kettenmann, 2007; Nimmerjahn et al., 2005). After infection, microglia are activated very rapidly, and induce a morphological change, chemotactic responses, cytokine production, phagocytosis, and reactive oxygen species (ROS) production (Kreutzberg, 1996). Patterns of pathogen-related molecular activity are recognized using homologous pattern recognition receptors (PRRs), and then activated (Block et al., 2007). However, little is known about how pathogen-derived micrometabolites activate microglia. Microglia expresses various G protein-coupled receptors (GPCRs) biologically detecting large or small molecules (Hickman et al., 2013; McHugh, 2012). Moreover, GPCRs include cytokine receptors and PRRs, which detect small metabolites and affect microglial activation. For example, GPR55, GPR18 and CNR2 recognize cannabinoids for stimulating the migration of microglia (Gong et al., 2006; Pietr et al., 2009), and OPRM1 recognizes a morphine analog (morphine sulfate, 758.8 Da) for inhibiting the migration of microglia (Chao et al., 1997). However, how these GPCRs are involved in the pathogen-brain axis remains an open question.

An odorant receptor (OR) is the largest subfamily in the group of GPCRs, accounting for 50% in humans and 60% in rats (Bjarnadottir et al., 2006). They can detect small molecules in various non-olfactory tissues such as renal, dermal and pancreatic tissues (Kang et al., 2015; Kang and Koo, 2012; Massberg and Hatt, 2018). For example, the recognition of a sandalwood scent by OR2AT4 promotes the proliferation of keratinocytes in human skin, and induces wound healing (Busse et al., 2014). Olfr78 helps renin secretion and blood pressure control by recognizing SCFAs in a renal juxtaglomerular apparatus (Pluznick et al., 2013). The recognition of hypoxic lactate by Olfr78 induces calcium enrichment in carotid glomus cells and regulates carotid nerve activity to control respiration (Chang et al., 2015). Consequently, these pieces of data suggest the fact that ORs act as receptors for pathogen-derived metabolites.

Bacterial meningitis is a life-threatening disease caused by direct infection of the central nervous system or hippocampus (Mook-Kanamori et al., 2011). *Streptococcus pneumoniae* (*S. pneumoniae*) is known as the main pathogen causing bacterial meningitis (Mook-Kanamori et al., 2011; van de Beek et al., 2006). The activation of microglia is mainly characterized by the brain's inflammatory response after *S. pneumoniae* infection (Mook-Kanamori et al., 2011; Rock et al., 2004). Some large molecules such as pneumococcal hemolysin (Braun et al., 2002; Kim et al., 2015), pneumococcal hemolysin membrane protein C (Peppoloni et al., 2006) and cell membrane components can induce microglial activation (Hanisch et al., 2001).

Under such a technical background, while studies on the relationship between microglia and ORs are being actively conducted, there is no study on treatment using an OR for microglia as a marker and the interaction between a metabolite caused by a pathogen and the OR for microglia, and thus this study is urgently needed.

DISCLOSURE

Technical Problem

The present invention is directed to providing a composition for detecting microglia, which includes an agent for measuring an activity or expression level of an odorant receptor Olfr110 or Olfr111.

The present invention is also directed to providing a method of screening a material for controlling microglial activity or expression, which includes: preparing microglia expressing Olfr110 or Olfr111; treating the microglia with a candidate; and selecting the candidate as a material for controlling the activity or expression of microglia when the activity or expression of the Olfr110 or Olfr111 is changed in the candidate-treated microglia, compared to a control.

The present invention is also directed to providing a composition for preventing or treating meningitis, which includes an inhibitor or activator for the interaction between 2-pentylfuran (2-PF) and Olfr110 or Olfr111 as an active ingredient.

The present invention is also directed to providing a health functional food for preventing or improving meningitis, which includes an inhibitor or activator for the interaction between 2-pentylfuran and Olfr110 or Olfr111 as an active ingredient.

Other purposes and advantages of the present application will be more apparent by the following detailed description with reference to the accompanying claims and drawings. Contents that are not disclosed herein will not be described since they can be sufficiently recognized and inferred by those of ordinary skill in the art or a similar art.

Technical Solution

One aspect of the present invention provides a composition for detecting microglia, which includes an agent for measuring an activity or expression level of Olfr110 or Olfr111.

The term "microglia" used herein refers to glial cells of the central nervous system derived from the mesoderm, and cells that perform primary immune functions in the central nervous system. Microglia are responsible for supporting tissues, supplying materials necessary for nerve cells, delivering, destroying and removing materials in tissues, and have different characteristics depending on activation.

The term "detection" used herein generally means determination of the presence or absence of any element or ionic compound in a sample by chemical analysis. In the present invention, the microglia detection means analysis of an activity level of microglia in a biological sample. More specifically, when a biological sample is purified and then treated with a composition for detecting microglia, the activation level of microglia may be detected due to the interaction between an OR and the composition for detection.

The activation of microglia may include a morphological change, an increase in phagocytosis, a change in intracellular calcium ions, the evaluation of cell chemotaxis, and an increase in cytokine secretion. More specifically, when microglia, which maintain their original shape of a long and thin cell body, detect toxins entering from the outside or generated inside, the shape may be changed into an activated shape with a thick and short branch and a thick cell body to protect nerve cells from these toxins. The activated microglia actively perform phagocytosis, unlike normal microglia, undergo cell proliferation, and express genes of cytokines such as TNF-$\alpha$, IL-1$\beta$ and IL-6, chemokines, inducible nitric oxide synthase (iNOS), and cyclooxygenase-2 (COX-2), thereby generating inflammatory mediators. The activation of microglia removes damaged cells and protects nerve cells from bacteria or viruses invading from the outside, and also damages the nerve cells when overactivated.

More specifically, the biological sample may be nerve cells, nerve tissue, or nerve-derived cells, but the present invention is not limited thereto.

A material for activating the microglia may be lipopolysaccharide (LPS), which is a bacterial endotoxin, interferon-$\gamma$, beta-amyloid, a ganglioside or 2-PF, and in one embodiment, 2-PF or a furan derivative.

The composition for detecting microglia may include an agent for measuring an expression or activity level of Olfr110 or Olfr111.

The term "odorant receptor (OR) Olfr110 or Olfr111" is a type of OR accounting for the largest group of G protein-binding receptors (GPCRs). The Olfr110 or Olfr111 is included in olfactory cells, and also in non-olfactory cells. A total number of the receptors is known to be about 400 in humans. Among the receptors, Olfr110 or Olfr111 is known to be specifically expressed in microglia. In one experiment of the present invention, Olfr110 or Olfr111 may be present in non-olfactory cells. For example, the non-olfactory cells may be nerve cells, nerve tissue or brain cells, but the present invention is not limited thereto.

The term "measurement of a protein activity or expression level" is a process of confirming the presence or absence and activity level of a protein of the Olfr110 or Olfr111 in a biological sample. More specifically, the measurement is for measuring whether microglia are activated in nerve cells. For example, the measurement may include a morphological change, an increase in phagocytosis, a change in intracellular calcium ions, the evaluation of cell chemotaxis, and an increase in cytokine secretion. In addition, the measurement may include confirming a protein level using an antibody, aptamer, probe or polypeptide, which specifically binds thereto, but the present invention is not limited thereto.

In one embodiment, the agent for measuring an activity or expression level may be an antibody, aptamer or polypeptide capable of binding to the protein, a primer or probe capable of binding to mRNA of the gene.

The term "antibody" used herein refers to a protein molecule specific for an antigenic site. For the purpose of the present invention, the antibody means an antibody specifically binding to the protein, that is, Olfr110 or Olfr111, and includes all of a monoclonal antibody, a polyclonal antibody and a recombinant antibody. The monoclonal antibody may be prepared using a hybridoma method (Kohler and Milstein (1976) European journal of Immunology 6:511-519), or a phage antibody library technique (Clarkson et al, Nature, 352:624-628, 1991; Marks et al, J. Mol. Biol., 222:58, 1-597, 1991), which are well known in the art. The polyclonal antibody may be produced by a method well known in the art for obtaining a serum containing antibodies by injecting the protein antigen into an animal and collecting blood from the animal. The polyclonal antibody can be prepared from a host of any animal species, such as a goat, a rabbit, sheep, a monkey, a horse, a pig, a cow or a dog. In addition, the antibody of the present invention includes a special antibody such as a chimeric antibody, a humanized antibody, and a human antibody.

In the specification, further, the antibody used herein includes a functional fragment of an antibody molecule as well as a complete form with two full-length light chains and two full-length heavy chains. The functional fragment of the antibody molecule may mean a fragment having at least an antigen-binding function, and may include Fab, F(ab'), F(ab')2 and Fv.

As a method for measuring the activity or expression of an OR, Olfr110 or Olfr111 protein, in a biological sample using this antibody, any method for confirming the degree of production an antigen-antibody complex by treating the biological sample with the antibody may be used without limitation. The "antigen-antibody complex" refers to a binding product of the Olfr110 or Olfr111 protein and an antibody specific therefor, and the amount of formation of the antigen-antibody complex can be quantitatively measured through the magnitude of a signal of the detection label. For example, the method may be western blotting, enzyme-linked immunosorbent assay (ELISA), an immunoprecipitation assay, a complement fixation assay, a fluorescence activated cell sorter (FACS) or a protein chip, but the present invention is not limited thereto.

In addition, the "aptamer" used herein refers to single-stranded DNA (ssDNA) or RNA, which has high specificity and affinity to a specific material. The aptamer has very high affinity for a specific material, is stable, can be synthesized by a comparatively simple method, can be modified in various ways to increase a binding strength, and has very higher specificity and stability than an antibody which has been previously developed because a cell, a protein and a small organic material can also be a target material.

The aptamer of the specification is not limited as long as it can specifically bind to the Olfr110 or Olfr111 receptor, and unless particularly defined otherwise, a base used for the aptamer may be selected from the group consisting of deoxy type bases of A, G, C and U.

In addition, for increasing stability, the aptamer may be modified by linking one or more selected from the group consisting of polyethylene glycol (PEG), inverted deoxythymidine (idT), a locked nucleic acid (LNA), 2'-methoxy nucleoside, 2'-amino nucleoside, 2'F-nucleoside, an amine linker, a thiol linker and cholesterol to the 5' end, a middle part, the 3' end, or both ends. The inverted deoxythymidine (idT) is one of molecules generally used to prevent nuclease-mediated degradation of an aptamer with weak resistance against nucleases. While nucleic acid units form a chain by linkage of the 3'-OH of the preceding unit with the 5'-OH of the following unit, idT is a molecule having an effect of inhibiting degradation by 3' exonuclease, which is one type of nuclease, by giving an artificial change to expose 5'-OH, not 3'-OH, by linkage of the 3'-OH of the preceding unit with the 3'-OH of the following unit.

In another embodiment, a method of screening a material for regulating the expression or activity of microglia, which includes selecting the candidate as a material for regulating the activity or expression of microglia when the activity or expression of the Olfr110 or Olfr111 is changed in the candidate-treated microglia, compared to a control, after microglia including the Olfr110 or Olfr111 are prepared, and then treated with a candidate, is provided.

According to one embodiment of the present invention, the preparation of microglia may be performed by extracting microglia from the embryonic cortex of an E18.5 mouse and culturing the extracted microglia, and performing centrifugation.

The term "candidate" used herein refers to a material which is regulated by increasing or decreasing microglia activation, and more specifically, a material that increases activation may be an activator or agonist, and a material that decreases activation may be a competitive inhibitor or antagonist. In addition, the candidate may include compounds, natural materials, and biopharmaceuticals (antibodies, aptamers, polypeptides, etc.).

According to one embodiment of the present invention, the candidate may be a ligand of Olfr110 or Olfr111.

In addition, the candidate may include one or more selected from the group consisting of 2-pentylfuran, 2-methylfuran, 2,3-dimethylfuran, 2-ethylfuran, 2-propylfuran, 2-butylfuran, 2-t-butylfuran, 2-pentylfuran, 2-hexylfuran, 2-heptylfuran and a derivative compound thereof. According to one embodiment of the present invention, the action of the candidate is regulation to increase or decrease microglial activation, and more specifically, when Olfr110 and 2-PF interact, an activation gene may be up-regulated.

The term "selection" used herein is for screening a necessary material from several materials. More specifically, when the prepared microglia are treated with a candidate, when the microglial activation is increased or decreased compared to a normal control, the candidate is selected as an activation regulatory material, and when there is no change in microglial activation compared to a normal control, selection may not be performed.

More specifically, the screening method may further include treating 2-PF which interacts with Olfr110 or Olfr111. When the microglia are treated with a candidate, the screening method is a method of selecting the candidate as a material for regulating the expression or activity of microglia by treating the microglia with a candidate along with 2-PF or a furan derivative, which interacts with Olfr110 or Olfr111. According to the method, the increase or decrease in the interaction between Olfr110 or Olfr111 and 2-PF may be confirmed, and when the interaction is increased or decreased compared to a control, the candidate is selected as a material for activating or regulating microglia.

Still another aspect provides a pharmaceutical composition for preventing or treating a neuroinflammatory disease or meningitis, which includes an inhibitor or activator against the interaction between 2-PF and Olfr110 or Olfr111 as an active ingredient.

Yet another aspect provides a health functional food for preventing or improving a neuroinflammatory disease or meningitis, which includes an inhibitor or activator against the interaction between 2-PF and Olfr110 or Olfr111 as an active ingredient.

The term "prevention" used herein may refer to all actions of delaying or inhibiting the occurrence of a neuroinflammatory disease or meningitis by the administration of a pharmaceutical composition.

The term "treatment" used herein means all actions involved in improving or beneficially changing symptoms by administration of a pharmaceutical composition, and refers to or includes alleviation, inhibition of progression, or prevention of a disease, disorder or condition, or one or more symptoms thereof.

The term "improvement" used herein may mean all actions of alleviating symptoms of a neuroinflammatory disease by administration of a pharmaceutical composition.

In one embodiment of the present invention, meningitis may be bacterial meningitis.

The "meningitis" used herein includes various diseases with inflammation in the subarachnoid space between the arachnoid mater and a soft membrane, and refers to meningitis occurring by virus or bacterial invasion into the subarachnoid space. The meningitis also includes inflammation by a specific chemical and dissemination of cancer cells into the subarachnoid space.

In one embodiment, the meningitis may be bacterial meningitis. More specifically, the bacterial meningitis may be caused by *Streptococcus pneumoniae, Hemophilus influenzae, Neisseria meningitides* or *Listeria monocytogenes*. Preferably, the bacterial meningitis may be caused by *Streptococcus pneumoniae*. The term "interaction inhibitor" used herein includes all materials that can inhibit the interaction between the Olfr110 or Olfr111 and 2-PF. More specifically, the interaction inhibitor may be an antagonist or a competitive inhibitor.

The term "interaction activator" used herein includes all materials that can promote the interaction between the Olfr110 or Olfr111 and 2-PF. More specifically, the interaction activator may be an agonist.

According to one embodiment of the present invention, the interaction may be hydrophobic interaction. For example, the compounds may competitively inhibit the interaction between the 2-PF and the Olfr110 or Olfr111. The compound may serve as a competitive inhibitor to inhibit the hydrophobic interaction between an amino acid residue Y253, F102 or F104 of the OR and 2-PF. The "antagonist" may be a material that antagonistically influences binding to each receptor of any biological material (agonist), but does not exhibit a physiological action by each receptor. Preferably, the compound may mean a drug serving to attenuate a part or all of the action by the combined use of one drug and another drug. The "agonist" is a material that generally serves to stimulate a receptor positively, and may be called an agonist.

More specifically, the interaction inhibitor may be a vector, antisense nucleotide, short hairpin RNA, or small interfering RNA, which complementarily binds to mRNA of Olfr110 or Olfr111.

In addition, the interaction inhibitor or activator may be a peptide, peptide mimetics, substrate analog, aptamer or antibody, which complementarily binds to the OR, that is, the Olfr110 or Olfr111 protein.

The term "siRNA" used herein refers to a nucleic acid molecule that can mediate RNA interference or gene silencing (see WO00/44895, WO 01/36646, WO 99/32619, WO 01/29058, WO 99/07409 and WO 00/44914). Since siRNA can inhibit the expression of a target gene, it is provided as an effective gene knock-down method or a gene therapy method.

The antibody or aptamer is described as above.

According to one embodiment of the present invention, the interaction inhibitor or activator may include one or more selected from the group consisting of 2-pentylfuran, 2-methylfuran, 2,3-dimethylfuran, 2-ethylfuran, 2-propylfuran, 2-butylfuran, 2-t-butylfuran, 2-pentylfuran, 2-hexylfuran, 2-heptylfuran and a derivative compound thereof, and more preferably, 2-ethylfuran. In addition, the interaction inhibitor or activator may include compounds, natural substances, and biopharmaceuticals (antibodies, aptamers, polypeptides, etc.). According to one embodiment of the present invention, when an experimental group co-treated with 2-ethylfuran and 2-PF was injected, the production of active oxygen was reduced compared to when only 2-pentylphenyl was injected, and was concentration-dependent.

More specifically, in the prevention or treatment by the therapeutic composition, an activation signal of microglia may not be up- or down-regulated by inhibiting or activating the interaction when the composition including an inhibitor or activator against the interaction between 2-PF and the Olfr110 or Olfr111 as an active ingredient is administered into a subject in need thereof. As a result, the activation of microglia may be regulated, resulting in cytokine secretion, a decrease in pathogenic behavior, and a decrease in phagocytosis. Therefore, the occurrence of a neuroinflammatory disease or meningitis may be prevented, improved or treated.

In addition, the pharmaceutical composition may include a pharmaceutically acceptable carrier in addition to the active ingredient. Here, the pharmaceutically acceptable carrier is conventionally used in formulation, and includes, but is not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. As well as the above components, the pharmaceutical composition according to the present invention may further include a lubricant, a wetting agent, a sweetening agent, a flavoring agent, an emulsifier, a suspending agent, or a preservative.

The pharmaceutical composition of the present invention may be administered orally or parenterally (e.g., intravenously, subcutaneously, intraperitoneally or locally) depending on a desired method, and for example, may be administered subcutaneously (that is, a skin preparation for external use) or orally (that is, an oral preparation), but the present invention is not limited thereto.

As a buffer added to various dosage forms, it is preferable that it is isotonic and non-irritating, and has a pH of 4 to 9 or 5 to 9. A dosage may be suitably selected by one of ordinary skill in the art according to a patient's condition and body weight, the severity of a disease, a drug type, an administration route and time.

The pharmaceutical composition may be administered at a pharmaceutically effective amount. The term "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

The effective amount of the pharmaceutical composition may be changed according to a patient's age, gender, condition and weight, the absorption of an active ingredient into the body, an inactivation rate, an excretion rate, a disease type, and a co-used drug, and generally 0.1 to 500 mg per kg of body weight may be administered daily or every other day, or one to five times a day. However, the effective amount may be increased or decreased depending on the route of administration, the severity of obesity, gender, a body weight or age, and thus it does not limit the scope of the present invention in any way.

In the health functional food, the active ingredient may be directly added to food or used together with other food or food ingredients, and may be suitably used according to a conventional method. The mixing amount of the active ingredient may be suitably determined according to the purpose (for prevention or improvement) of use thereof. Generally, in the production of food or beverages, the composition of the present invention is added at 60 wt % or less, and preferably 40 wt % or less with respect to the raw materials. However, in long-term consumption for health and hygiene or health control, the amount of the composition may be the same as or lower than the above-mentioned range.

The food composition of the present invention has no limitation to components, other than containing the active ingredient as an essential component at an indicated proportion, and may contain various flavoring agents or natural carbohydrates like a conventional beverage. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, *stevia* extract (e.g., rebaudioside A, glycyrrhizin, etc.)] and synthetic sweeteners (saccharin, aspartame, etc.) may be advantageously used. The proportion of the natural carbohydrate may be suitably determined by the choice of those of ordinary skill in the art.

The food composition of the present invention may contain various nutrients, vitamins, minerals (electrolytes), flavoring agents including synthetic and natural flavoring agents, coloring agents, fillers (cheese, chocolate, etc.), pectic acid and a salt thereof, alginic acid and a salt thereof, organic acids, protective colloidal thickening agents, pH adjusters, stabilizers, preservatives, glycerin, alcohols, or carbonizing agents used in carbonated beverages, and such components may be used independently or in combination. A proportion of such an additive may also be suitably selected by those of ordinary skill in the art.

Each description and embodiment disclosed in the present application may also be applied to each other description and embodiment. That is, all combinations of the various elements disclosed in the present application are included in the scope of the present application. In addition, it cannot be considered that the scope of the present application is limited by the specific description described below.

Advantageous Effects

According to the olfactory receptor marker of microglia and uses thereof according to an aspect, the activity or expression level of the olfactory receptor Olfr110 or Olfr111 protein can be measured to detect microglia, and using this, the olfactory receptor of microglia. In addition to being able to select a ligand, there is an effect that the olfactory receptor and the 2-PF interaction inhibitor or activator can be used for the treatment of neuroinflammatory diseases or meningitis.

DESCRIPTION OF DRAWINGS

The above and other objects, features and advantages of the present invention will become more apparent to those of ordinary skill in the art by describing in detail exemplary embodiments thereof with reference to the accompanying drawings, in which:

FIG. 1 are color heat maps showing residence frequencies after each of control media (Ctrl) and culture supernatants (Sup) into which three different amounts ($10^4$, $10^5$, and $10^6$ colony forming units, CFU) of *S. pneumoniae* are introduced, are intraperitoneally (IP) injected into each mouse. A total distance was quantified under the same conditions (10/condition at n=5) ($P<0.05$; , $P<0.01$; and *, $P<1.0\times10^{-3}$);

FIG. 2 is the result of measuring mRNA expression levels of pro- (Tnf, Il6, Il1b) and anti-inflammatory cytokines (Il10, Il13) in microglia in the cerebral cortex which has been subjected to Sup treatment and IP injection;

FIG. 3 is the result of measuring mRNA expression levels of pro- (Tnf, Il6, Il1b) and anti-inflammatory cytokines (Il10, Il13) in astrocytes in the cerebral cortex which has been subjected to Sup treatment and IP injection;

FIG. 4 shows protein amounts of cytokines measured in primary microglia treated with Sup, prepared with four different doses (1, 10, 100, and 1000 multiplicity of infection, MOI; n=5/condition) of *S. pneumoniae* (Tnf, IL6, IL1b) ($P<0.05$; , $P<0.01$; and *, $P<1.0\times10^{-3}$);

FIG. 5 is a set of representative fluorescent images showing that a GFP intensity reflects the morphology of Ctrl- and Sup-treated microglia. The images show microglia in the cerebral cortex after IP injection of Ctrl or Sup into CX3CR1$^{GFP/+}$ mice. Scale bar: 20 um. The GFP intensity was quantified under two conditions as follows (n=3 to 5 mice/condition);

FIG. 6 is a set of images showing the amount of accumulated $O_2^-$ which has been produced after Ctrl and Sup treatment, measured every minute for 25 minutes. Data is expressed as mean±SEM at each point of time;

FIG. 7 is a set of images showing primary microglia migrated by Ctrl or Sup. The images are made using a Boyden chamber assay. A chemotaxis index indicates the quantified number of the migrated microglia (n=5/condition);

FIG. 8 shows the distribution of primary microglia of fluorescein isothiocyanate (FITC)-dextran measured by fluorescence activated cell sorting (FACS) analysis after Ctrl or Sup treatment. A phagocytosis index represents the mean fluorescence intensities (MFIs) (n=5/condition);

FIG. 9 is a set of images showing chemotaxis analysis and ROS production ($P<0.05$; , $P<0.01$; and *, $P<1.0\times10^{-3}$);

FIG. 10 shows chemotaxis analysis, and phagocytosis after Ctrl, Sup and flow-through (FT) treatment ($P<0.05$; , $P<0.01$; and *, $P<1.0\times10^{-3}$);

FIG. 11 shows that ORs are expressed in primary microglia according to mRNA-seq data;

FIG. 12 shows a relative expression level of ORs induced by Sup treatment;

FIG. 13 shows that the relative luciferase activity (y axis) of Olfr110 and Olfr111 is measured with increasing concentrations of 11 furan analogues;

FIG. 14 shows the relative luciferase activity of candidate metabolites, compared to Olfr110 and Olfr111;

FIG. 15 shows the relative luciferase activity of Olfr111;

FIG. 16 is a circular map explaining molecular receptive ranges of Olfr110 and Olfr111 for 11 furan analogues. Analogues located in the center are analogues with the highest reactivity, and analogues located at the edge have the weakest reactivity;

FIG. 17 shows a structural model of a 2-PF-Olfr110 polymer complex showing four critical residues (F102, F104, Y252, and Y259) for the interaction between 2-PF and Olrf110;

FIG. 18 shows the relative luciferase activities (y axis) of wild-type Olfr110 and nine Olfr110 mutants (indicated in the legend), measured with an increasing concentration (x axis) of 2-PF;

FIG. 19 is a set of images showing migrated Hana3A cells expressing MOCK, Olfr110, or Olfr111 to 2-PF. The images are made using a Boyden chamber assay. A chemotaxis index representing the number of migrated microglia was measured after treatment with a control solvent (NT) or 2-PF at concentrations of 10, 100 and 1000 μm(n=5/condition);

FIG. 20 shows ion chromatograms (EICs) extracted for the precursor ion of 2-PF (m/z=153.091) obtained from LC-MS/MS datasets for synthetic 2-PF, Sup, and control media (Ctrl);

FIG. 21 shows MS/MS spectra of 2-PF precursor ions in synthetic 2-PF and Sup. fragmented ions of 2-PF precursor ions, shown with their corresponding structures, as predicted by HMDB (Wishart et al., 2007);

FIG. 22 shows EICs for 2-PF precursor ions in Sup after addition of $10^2$ and $10^4$ μM 2-PF;

FIG. 23 shows an assay for cytotoxicity;

FIG. 24 shows an assay for ROS;

FIG. 25 shows an assay for phagocytosis. It was measured after treating Sup with control media (Ctrl) and ATP, or with an increasing concentration of 2-PF (0, 100, 300, or 500 μM) (refer to the detailed description);

FIG. 26 is an image showing the olfactory epithelium (OE) and the olfactory bulb (OB) used as positive controls, as well as western blots of primary microglia and astrocytes Olfr110. β-actin was used as a loading control;

FIG. 27 is a set of images of co-immunostaining analysis showing expression of Olfr110 (red) and Iba-1 (green) in the cerebral cortex (left panels): a microglia marker; expression of Olfr110 and GFAP (green), a microglia marker in the hippocampus (middle panels); expression of Olfr110 and NeuN (green), a neuronal marker, in the cerebral cortex (right panels). DAPI is shown in blue (Scale bar: 50 μm);

FIG. 28 is an image of immunostaining analysis showing expression of Olfr110 (red) in GFP(+)microglia (green) in the CX3CR1$^{GFP/+}$ cerebral cortex. Left and right panels show low- and high-power images. Scale bar: 50 μm (left) and Scale bar: 20 μm (right);

FIG. 29 is a set of images of immunostaining analysis showing expression of Olfr110 measured after treatment with PBS (Ctrl) and 2-PF (lower panels) as well as control media (Ctrl) and Sup (upper panels). The Olfr110 expression level was quantified according to the intensity of red light;

FIG. 30 is a set of heat maps showing residence frequency of mice after IP injection of a PBS solvent and 2-PF at three concentrations. A total migration distance was quantified under the same conditions and displayed on a bar graph;

FIG. 31 is a graph showing mRNA expression levels of inflammatory cytokines in the cerebral cortex after IP injection of 2-PF;

FIG. 32 is a set of fluorescence images showing the intensity of GFP of microglia after a control or 2-PF is injected into a CX3CR1$^{GFP/+}$ mouse, generated by microglia in the cerebral cortex;

FIG. 33 is a set of time-lapse confocal microscopy images formed by measuring cerebral cortex slices at different time points (1, 16, 25, 40 and 92 min) after treatment with control or 2-PF. The volume of microglia is shown in green, and protrusions under phagocytosis are represented with arrows;

FIG. 34 is a graph showing the degree of mRNA expression of inflammatory cytokines of primary microglia transfected with non-targeting siRNA+Mock (siCtrl), siRNA against Olfr110+Mock (siOlfr110), and siRNA against Olfr110+rescue vector (Rescue) after 2-PF pretreatment (*, P<0.05; , P<0.01; and *, P<0.001);

FIG. 35 is a set of graphs showing protein levels of Tnf and 116 in culture supernatants after 2-PF treatment;

FIG. 36 is a set of graphs showing accumulated amounts of oxygen generated in primary microglia after siRNA transfection followed by 2-PF treatment. The graphs show measurement values at 1-minute intervals for 25 minutes;

FIG. 37 is a set of graphs showing distribution of primary microglia with FITC dextrin intensities measured by FACS analysis after siRNA transfection. Measurements are as described in FIG. 36. A phagocytosis index shows quantified average fluorescence intensity;

FIG. 38 is a set of images showing primary microglia at three different concentrations (10, 100, and 1000 μM) of 2-PF;

FIG. 39 is a representative brain image (yellow) showing transfected microglia. Non-microglia are shown in red, and the non-transfected microglia are shown in green. The region represented by an asterisk is the cerebral cortex of a CX3CR1$^{GFP/+}$ mouse after stereotactic injection FIG. 40 is a graph obtained by measuring mRNA expression levels of Olfr110 and Olfr111, measured after injection of non-targeting siRNA+Mock+siGLO (Ctrl); Olfr110 siRNA+Mock+siGLO (siOlfr110); or Olfr110 siRNA+rescue vector+siGLO (Rescue) (*, P<0.05; , P<0.01; and *, P<0.001);

FIG. 41 is a set of images showing distribution of beads in three types of cells in the brain of a CX3CR1$^{GFP/+}$ mouse. Beads are represented by white dots, and microglia are represented by yellow dots. The beads and the microglia were counted in six different locations in three independent mice under three different conditions, and the counted beads were displayed in a bar graph (*, P<0.05; , P<0.01; and *, P<0.001);

FIG. 42 shows the relationship between DEGs in microglia of a control and an experimental group. Each number means a DEG number;

FIG. 43 is a heat map showing log$_2$-fold-changes of up-regulated (red) and down-regulated (green) genes;

FIG. 44 is a graph showing that GOBPs are enriched by an up-regulated gene in 2-PF-treated microglia;

FIG. 45 is a graph showing cAMP production of microglia (n=5/condition) treated at different concentrations (0, 100, and 500 μM) in groups treated with SQ22536 (adenylyl cyclase inhibitor) or not;

FIG. 46 is a graph showing cAMP produced in primary microglia after treatment with the same concentration of 2-PF (n=5/condition);

FIG. 47 is a set of images obtained by measuring increased calcium concentrations in microglia by fura-2AM calcium imaging. A high concentration is shown in red, and a low concentration is shown in green;

FIG. 48 shows western blots of phosphorylated ERK (pERK), p38 (pp38), JNK (pJNK) and Akt (pAkt) measured in primary microglia using western blotting analysis at 0, 2, 5, 10, 20 and 30 min after treatment with 2-PF and LPS. β-actin was loaded;

FIG. 49 shows levels of Tnf and 116 secreted from primary glial cells after pretreatment with 2-PF. The experiment was conducted with groups pre-treated with adenylyl cyclase (SQ: SQ22536) or not;

FIG. 50 is a graph showing an amount of ROS generation under the same experimental conditions as used in FIG. 49;

FIG. 51 is a graph showing phagocytosis levels under the same experimental conditions as used in FIG. 49;

FIG. 52 is a set of images of migrated microglia and a graph showing cytotoxicity under the same experimental conditions as used in FIG. 49 (n=5);

FIG. 53 shows amounts of ERK, phosphor-ERK (pERK), CREB, and phosphor-CREB (pCREB), measured in primary microglia by western blots after pre-cultivation with SQ22536 or pd98059 and 2-PF treatment (*, P<0.05; , P<0.01; and *, P<0.001);

FIG. 54 is a graph showing an increased concentration of 2-EF co-treated with 300 μM 2-PF (x axis), and relative luciferase activity of Olfr110 (y axis) (*, P<0.05; , P<0.01; and *, P<1.0); and FIG. 55 shows a graph (left) of ROS generation in primary microglia treated with 2-EF-treated Sup and untreated Sup, representatively, and a graph (right) of ROS generation in primary microglia treated with each of 500 μM 2-PF-cotreated 2-EF Sup and untreated 2-EF-treated Sup (*, P<0.05; , P<0.01; and *, P<1.0). The graphs are plotted by ANOVA and a Tukey post-hoc correction method.

MODES OF THE INVENTION

Hereinafter, the present invention will be described in detail with reference to examples. However, these examples are merely provided to exemplify the present invention, and the scope of the present invention is not limited to the following examples.

REFERENCE. EXPERIMENTAL MATERIALS AND EXPERIMENT PREPARATION

1. Culture of Microglia and Astrocytes

In this example, microglia or astrocytes were primarily extracted from the cerebral cortex of E18.5 mouse embryos (Tamashiro et al., 2012), and cultured as described in Example 1. More specifically, the mouse embryonic cortex was collected, stored in a cold supernatant (#14170-112; Thermo Fisher Scientific), and pretreated in a 0.25% trypsin solution (#15090-046; Thermo Fisher Scientific) at 37° C. for 20 minutes. Afterward, cells were plated in a minimum nutrient medium supplemented with 10% FBS (#SH30919.03; Hyclone), 2 mM L-glutamine (#25030-081; Thermo Fisher Scientific), 0.04% glucose (#G7021; Sigma Aldrich), and 1% penicillin/streptomycin (#15140-122; Thermo Fisher Scientific), and filtered through a 40 pin strainer (#352340; Thermo Fisher Scientific). The microglia were plated at a density of $1.2 \times 10^7$ cells in a T75 flask coated with poly-D-lysine (#P7280; Sigma Aldrich). After 2 hours, the mixture was transferred to a Dulbecco's modified eagle medium (DMEM; #SH30243.01; Hyclone), and the medium was replaced with a medium every 3 days for 2 weeks. To isolate microglia from this mixed solution, first, the cells were shaken at 37° C. and 150 rpm for 2 hours, the mixed solution containing microglia was extracted from the top and then transferred, followed by isolating the microglia through centrifugation at room temperature and 1300 rpm for 5 minutes. The isolated microglia were transferred to a culture medium. After the microglia were transferred, the remaining mixed solution was incubated with shaking at 160 rpm for 1 day to completely remove the microglia. Subsequently, the resulting product was treated with 0.25% trypsin to isolate astrocytes, and the cells were incubated again in a T75 flask for 4 days and then collected. Purities of the collected microglia and astrocytes were evaluated by qRT-PCR assay and immunocytochemistry using a marker gene and proteins such as Iba-1 and Gfap.

2. Selection of 2-PF from S. pneumoniae Culture

Two types of encapsulated serotype strains (D39 S. pneumonia, Kim et al., 2015) were cultured with 30 g of sterilized Todd Hewitt Broth (#249240; BD Biosciences) and a 0.5% yeast extract (#288620; BD Biosciences). Subsequently, the grown bacteria were transferred into THY broth, and incubated at 37° C. for 24 to 48 hours to a concentration of $10^8$ CFU/ml. The culture was maintained at 4° C. and 4,000×g, and centrifuged for 10 minutes to isolate culture supernatants (Sup), and then the supernatants were used for intraperitoneal injection (IP). To isolate a fraction containing a metabolite, the supernatants were further filtered through an Ultracel YM-3 membrane (3 kDa pore, Millipore Corporation, Bedford, Mass.). In addition, for this experiment, a synthetic 2-PF solution with a 98% purity was prepared, and then the same amount of methanol was added to the synthetic solution, thereby preparing a mixed solution. A concentration of $10^2$ or $10^4$ CFU/ml, 2-PF (St. Louis, MO, purchased from USA) was added to Sup, and the resulting product was treated with 0.1% TFA.

3. Preparation of Animal Models

All mice were maintained and cared according to the protocols approved by the Institutional Animal Care and Use Committee of the Daegu Gyeongbuk Institute of Science and Technology (DGIST) under standard temperature control and laboratory conditions or conditions enabling free access to colored tunnels, mazes, climbing materials and running wheels. In both in vivo and ex vivo experiments, 8 to 10-week-old BL6J or heterozygous $CX3CR1^{+/GFP}$ mice were used. The mice were prepared by crossing C57/BL6J and $CX3CR1^{GFP/GFP}$ (Jung et al. 2000). All mice were provided with sterile food and water ad libitum at 12-hour intervals at room temperature.

4. Method for Conducting qRT-PCR

To measure mRNA, RNA was isolated from red blood cells, microglia, astrocytes, Hana3A cells or cerebral cortex cells using a MagNa lyser (Roche Molecular Diagnostics) with TRIzol reagent (Invitrogen, Carlsbad, Calif.) according to the manufacturer's protocols. Afterward, cDNA was synthesized through reverse transcription using isolated mRNA (using PrimeScript™ 1st str and cDNA Synthesis kit-#6110; Takara Bio Inc.). This process was quantitatively measured in real time through quantitative real-time-PCR (using a LightCycler® 480 SYBR Green I Master). The measurement values were calculated using a 2-ΔΔCt method.

5. Method for Conducting Cytokine ELISA Assay

The levels of expression of cytokines Tnf, il6 and I11b secreted from microglia were measured according to the manufacturer's protocols. More specifically, the levels were measured by ELISA 24 hours after treatment with 2-PF or a cell supernatant. The ELISA kit was purchased from BD Biosciences (#DY410 for Tnf; #DY406 for Il6; #DY401 for I11b).

6. Method for Quantitative Morphological Analysis

To analyze a morphological change in microglia activation, 9-week-old $CX3CR1^{GFP/+}$ mice were used. Two hours after an IP containing or not containing 2-PF was injected into two mice, brain sections were collected by cryosection. A 40-μm-thick brain tissue fragment was prepared by homogenization into smaller sizes of 1 μm, and a GFP signal of microglia was measured using a 40× magnification confocal microscope. A GFP-pixel signal of microglia was analyzed using Zeiss ZEN Software (Zeiss).

7. Method for Measuring Superoxide ($O_2^-$) Concentration

Superoxide concentrations were calculated by measuring the degree of cytochrome c reduction using a VersaMax microplate reader (Babior et al., 1973). Microglia were cultured in a 96 well plate at a concentration of $1.0 \times 10^5$ cells/well, and the microglia were activated by a 10 μM ATP solution containing 2-PF and cytochrome c, or a solution in which Sup is mixed with cytochalasin B (5 μM; #C66762; Sigma Aldrich). The concentration of ROS was measured through a change in light absorption every minute for 25 minutes at 550 nm.

8. Method for Measuring Chemotaxis

Chemotaxis was measured using a multi-well Boyden chamber. More specifically, a polycarbonate filter (8 μm pore; #101-8; Neuroprobe) was coated with 10 mg/ml fibronectin (Sigma-Aldrich) in PBS for 2 hours, and the coated filter was installed in a Boyden chamber. In addition, the bottom side of a plate was filled with serum-free DMEM containing 2-PF or a culture supernatant. Subsequently, microglia or Hana3A cells were transfected with an OR construct, and then suspended in serum-free DMEM. The microglia were kept at 37° C. for 4 hours, and the Hana3A cells for 8 hours. Cells that migrated to the bottom surface were fixed with 4% PFA, and stained with hematoxylin for 10 minutes. The migrated cells were counted under a light microscope in five randomly selected fixed magnetic fields (200×) using a scored eyepiece. A chemotaxis index was defined as the migrated cell number normalized against the untreated group.

9. Method for Measuring Phagocytosis

Primary microglia were seeded in 24-well plates ($5 \times 10^5$ cells/well) and incubated for 24 hours. Cells were preincubated with 2-PF or Sup for 30 minutes, incubated with FITC-dextran (1 mg/ml, 20 mg/ml in PBS; #FD70S; Sigma Aldrich) in serum-free DMEM at 37° C. for 30 days, and washed with PBS at 4° C. The cells were detached with 0.25% trypsin (#15090-046; Thermo Fisher Scientific) in PBS, and the detached cells were analyzed with FACS Accuri™ C6 (BD Biosciences). Mean fluorescence intensity (MFI) was calculated by integrating fluorescence histograms under each condition using the software. A phagocytosis index was defined as MFI, normalized against an untreated group.

10. Method for Measuring ROS Concentration

ROS levels were measured using 2',7'-dichlorodihydrofluorescein diacetate (DCF-DA, #D6883; Sigma Aldrich) by a previously described method with minor modifications (Bae et al., 2001). More specifically, primary microglia were seeded in 24-well plates ($5.0 \times 10^5$ cells/well) for 24 hours, and then treated with 10 μM DCF-DA at 37° C. for 30 minutes. One plate was treated with 2-PF, and the other one was not. The cells in each well were measured using a flow cytometer (FACS Accuri™ C6; BD Biosciences). MFI was measured as described above.

11. Odorant Receptor Cloning and Measurement of Cell Surface Expression

Full-length odorant receptor genes from mouse and human genomic DNAs were amplified using appropriate primers. The resulting cDNAs were digested with restriction enzymes, and as described above, the resulting product was ligated to produce an odorant receptor construct having a restriction site in a pME18S expression vector containing N-terminal Lucy, Flag, and Rho tags. All odorant receptor constructs were confirmed by sequencing (Shepard et al., 2013). Subsequently, the constructs were transfected into Hana3A cells with RTP 1S, and their localization and presence in the plasma membrane were confirmed as previously described (Behrens et al., 2009; Zhuang and Matsunami, 2008). Such transfection was performed with Lipofectamine2000 (#11668-019; Thermo Fisher Scientific) according to the manufacturer's instructions. More specifically, the transfected cells were grown on a coverslip (#0101050; Marienfeld) coated with poly D lysine (10 μg/ml; #P7280; Sigma Aldrich). The cells were then washed with a warm PBS solution, and cooled on ice for 30 minutes to block endocytosis. After washing with cold PBS, the cells were fixed with ice-cold methanol and acetone for 2 minutes (v/v=1:1) (Methanol: #106009; MERCK, Acetone: #179124; Sigma Aldrich). The cells were then incubated with normal horse serum (#008-000-121; Jackson ImmunoResearch) at room temperature for 1 hour. The resulting cells were incubated with mouse anti-rhodopsin (anti-Rho; 1: 1,000; #MABN15; Millipore) or rabbit anti-Olfr110 (#ab177327; Abcam) overnight at 4° C. After washing with PBS, a Cy3-conjugated donkey anti-mouse antibody (1: 1,000; #715-165-150; Jackson ImmunoResearch), an Alexa488-conjugated donkey anti-mouse antibody (1: 1,000; #715-545-150; Jackson ImmunoResearch), or a Cy3-conjugated donkey anti-rabbit antibody (1: 1,000; #711-165-152; Jackson ImmunoResearch) was treated at room temperature for 1 hour. The cells were mounted with a Vectashield fluorescent mounting medium containing DAPI (#H-1200; Vector Laboratories). The expression of a heterologous odorant receptor was analyzed with a confocal laser scanning microscope, LSM700, and the ZEN software (Zeiss).

12. Method for Measuring Luciferase Assay

A Dual-Glo luciferase assay system (#E2940; Promega) was used for OR ligand screening. More specifically, Hana3A cells were seeded in white polystyrene 96-well plates (#353296; BD Biosciences) one day before transfection. pCRELuc (1 μg; #219076; Agilent Technologies), pRL-SV40 (1 μg; #E2231; Promega), RTP1S (1 μg), and OR (6 μg; or Mock) vectors were transfected for 24 hours in each plate. Analysis was performed using Lipofectamine 2000 (#11668-019; Thermo Fisher Scientific) according to the manufacturer's protocols. Transfected cells were stimulated at 37° C. for 4 hours with various concentrations of diluted odorants in a CD293 medium (#11913-019; Thermo Fisher Scientific). The activity of luciferase was normalized to that of *Renilla* luciferase. Luminescence was measured using a SpectraMax L microplate reader (Molecular Devices).

13. Homology Modeling Method

The homology modeling of mouse Olfr111 and Olfr110 includes a template search, alignment of a gene sequence, model determination, and model quality evaluation. In addition, the homology modeling was performed using a Web-based homology modeling tool, SWISS-MODEL. The amino acid sequence of Olfr111 and Olfr110 was first obtained from NCBI Protein BLAST using the UniprotKB/Swiss-Prot database. Template searches for Olfr111 and Olfr110 were performed with BLAST and HHblits of the SWISS-MODEL Template Library (SMTL). As a result, 179 and 186 templates were found. To construct a homology model of Olfr111 and Olfr110, the X-ray crystal structure of a human adenosine A2A receptor (resolution: 2.7 Å, PDB ID: 3VG9) was selected as a temperature structure, based on both sequence identity and similarity. The 3D homology model structure was formed using Promod. The overall evaluation of the model was performed using the QMEAN scoring function. The final 3D model structure of Olfr111 and Olfr110 was downloaded from the SWISS-MODEL website.

14. Receptor-Ligand Molecular Modeling Docking Method

The 2D structure of a ligand was generated by ChemBioDraw (ver. 11.0.1), and transferred to Chem3D Pro (ver. 11.0.1), thereby generating a 3D structure. Processes used in ligand preparation and optimization were performed by the "Sanitize" protocol (default) in SYBYL-X 2.1.1 (Tripos Inc., St. Louis). A homology model of Olfr111 and Olfr110 (template structure PDB ID: 3VG9) was generated using a SWISS-MODEL homology modeling tool. The structure preparation tool in SYBYL-X 2.1.1 was used for protein preparation. The deletion of amino acid residues was fixed, and hydrogen atoms were added to a protein using the TRIPOS force field. Protein minimization was then performed by the POWELL method (Abagyan et al., 1994) after the initial optimization setting was changed to "None" from the default setting. In addition, the rate of Intermediation change was set to 0.5 kcal/(mol*Å), and the maximum repetition was set to 1000 times. Next, the entire docking process was performed using the protein and ligand prepared as above using the Surflex-Dock GeomX module (SYBYL-X 2.1.1). A docking site was induced by the Surflex-Dock protomol, which may, as a phenotype of an ideal ligand, represent all interactions with an existing binding site. The protocol was defined by jointly selecting the most highly expressed receptors on a multi-channel surface in SYBYL-X 2.1.1. Two protocol generation factors, Bloat and Threshold, were set to 0.5 (Å) and 0, respectively. The maximum number of generated poses was set to 20, and the minimum RMSD between the generated poses was set to 20. The minimum RMSD value between poses was set to 0.05. Other docking parameters of Surflex-dock GeomX were set to the default values.

15. Method for Generating Site-Specific Mutagenesis

Specific mutant vectors of the Olfr110 structure were generated using PfuUltra High-Fidelity DNA polymerase (#600380; Agilent Technologies). All mutant vectors (F102W; F104W; Y252F; Y259F; F102W/F104W; Y252F/Y259F; F102W/Y252F/Y259F; F104W/Y252F/Y259F; F102W/F104W/Y252F/Y259F) were sequenced in forward and reverse directions (Macrogen).

16. Sample Preparation

A synthetic 2-PF solution (purity of 98% or more) was purchased from Sigma Aldrich (St. Louis, Mo., USA). The same amount of absolute (99.9%) methanol was added to the original 2-PF solution. The original 2-PF solution and the methanol-added solution (2-PF+$CH_3OH$) were analyzed by direct infusion mass spectrometry. For liquid-chromatography-tandem-mass-spectrometry (LC-MS/MS) of synthetic 2-PF, a 2-PF+$CH_3OH$ solution was used. For LC-MS/MS of Sup and control media (Ctrl), Sup or Ctrl (1 ml) was filtered through an Ultracel YM-3 membrane with a pore size of 3 kD (Millipore Corporation, Bedford, MA) to remove proteins. 500 µl of a flow-through was mixed with the same volume of methanol. The resulting sample was sonicated for 10 minutes and centrifuged at 14,000 g and 4° C. for 20 minutes (Lau et al., 2015). The supernatant was analyzed by LC-MS/MS (FIG. 3A, B). In addition, each of $10^2$ and $10^4$ µM 2-PF was added to the Sup. The resulting sample was acidified with 0.1% trifluoroacetic acid (TFA), and analyzed by LC-MS/MS.

17. Direct Infusion with HESI Source

2-PF and 2-PF+$CH_3OH$ samples were injected into a HESI source at 20 µl/min using a 500-µl gas-tight syringe. They were observed for 8 minutes by a single-ion monitoring method of a Q-Exactive Hybrid Quadrupole-Orbitrap mass spectrometer. In addition, the capillary voltage was set to 3.5 kV (positive mode), and the temperature of a desolvation capillary was set to 250° C. Subsequently, the full mass spectrum was monitored in a mass range between for 50 to 750 Thomsons (Th) at a resolution of 70,000 (m/z 200). The maximum ion injection time was 100 ms, and the automatic gain control value was $1 \times 10^6$. The isolation window was set to m/z 1.0 (Looße et al., 2015).

18. LC-MS/MS Analysis

A Thermo EASY-nLC 1000 (Thermo Scientific, Odense, Denmark) equipped with an analytical column (Thermo Scientific, Easy-Column, 75 µm×50 cm) and a trap column (75 µm×2 cm) was used for LC separation. Parameters used herein are as follows: Injection volume=10 µl; operation temperature of the analytical columns=50° C.; flow rate=300 nL/min; mobile phase A=0.1% formic acid, mobile phase B=0.1% formic acid, and 2% water in acetonitrile. For LC separation, the following concentration gradients were used for 50 minutes: 2% to 40% solvent B over 36 min, 40% to 80% solvent B over 6 min, and 80% to 2% solvent B over 6 min. The eluted samples by LC were analyzed using a Q-Exactive™ hybrid quadrupole-Orbitrap mass spectrometer (Thermo Scientific) equipped with a nanoelectrospray source. A capillary voltage was set to 3.5 kV (positive mode), and a capillary temperature was set to 250° C. In addition, the Q-Exactive was set to a data-dependent mode, and scanning was performed in a mass range between 50 to 750 Th at a resolution of 70,000 (at m/z 200). As a result of the experiment, the most abundant, top 10 ions were isolated with 1.0 m/z. In addition, it was confirmed that the ions were fragmented by high energy collision. MS scans were detected at a resolution of 17,500 (Saigusa et al., 2016). The maximum ion injection times for full MS and MS/MS scans were 100 ms and 50 ms, respectively. The automated gain control target values for full MS and MS/MS scans were set to $1.0 \times 10^6$ and $1.0 \times 10^5$, respectively.

19. Methods of Obtaining Extracted Ion Chromatogram (EIC) and MS/MS Spectra

2-PF precursor ions were extracted from unprocessed data acquired using full MS scans including full MS and MS/MS scans (m/z=153.091 Da). The precursor ion was extracted by setting the chromatographic peaks to 17 and 22 or 16 and 22 within a tolerance of 2 ppm. In each spectrum, peaks corresponding to that of m/zf—the mass of $CH_3$ were assigned, resulting in obtaining a candidate structure with fragmented peak ions (HMDB) (Wishart et al., 2007).

20. Western Blotting

Cells and tissue were prepared using the T-PER® reagent (#78510; Thermo Fisher Scientific) containing protease inhibitors (#04-693-116-001; Roche Molecular Diagnostics) and DMSF (Sigma-Aldrich), and then lysed using a MagNA lyser (Roche Molecular Diagnostics). A total protein extract was quantified by the Bradford assay. The samples were dissolved in 7.5% SDS-PAGE or 4-20% gradient mini-PROTEIN TGX Precast Gels (#456-1064; Bio-Rad Laboratories), and then blotted on nitrocellulose membranes (#10600002; GE Healthcare). Afterward, the membranes were blocked for 1 hour in 5% non-fat dry milk and TBST, 0.1% TWEEN® 20 (#P9416; Sigma-Aldrich), and Tris-buffered saline, and then incubated with primary antibodies at 4° C. overnight. The antibodies were as follows: Olfr110 (36 kDa; 1:1,000; #ab177327; Abcam), anti-rhodopsin (39 kDa; 1:1,000; #MABN15; Millipore), CREB (43 kDa; 1:1,000; #9197; Cell Signaling Technology), phospho-CREB (43 kDa; 1:1,000; #9198; Cell Signaling Technology), ERK (44 kDa; 1:1,000; #sc094; Santa Cruz), phospho-ERK (42, 44 kDa; 1:1,000; #sc-7383; Santa Cruz), phospho-Akt (60 kDa; 1:500; sc-293125; Santa Cruz), phospho-JNK (46, 54 kDa; 1:500; sc-6254; Santa Cruz), phosphor-p38 (38 kDa; 1:1,000; sc-7973; Santa Cruz), and beta-Actin (45 kDa; 1:10,000; #4967; Cell Signaling Technology). In addition, as isotype-matched horseradish peroxidase-conjugated secondary antibodies, anti-rabbit IgG (#711-035-152; Jackson ImmunoResearch) diluted 1:100,000, and anti-mouse IgG (#715-035-150; Jackson ImmunoResearch) diluted 1:40,000 in TBST were used at room temperature for 2 hours. Immunoreactive protein bands were obtained using Super-Signal™ West Pico Chemiluminescent Substrate (#34080; Thermo Fisher Scientific).

21. Immunostaining

For immunofluorescence staining, microglia were cultured on a 22-mmm coverslip (#0101050; Marienfeld) which had been coated with poly-D-lysine (10 µg/ml; #P7280; Sigma Aldrich) under standard conditions for 48 hours. Subsequently, cells were washed in PBS, and fixed with 4% paraformaldehyde (#6148; Sigma Aldrich) for 5 minutes. The cells were then incubated in PBS containing 4% normal horse serum (#008-000-121; Jackson ImmunoResearch) and 0.1% TWEEN® 20 (#P9416; Sigma-Aldrich) at room temperature for 1 hour. Afterward, the cells were blocked at 4° C. overnight with primary antibodies listed below. The antibodies are as follows: Olfr110 (rabbit-anti-Olfr110; 1:10,000; #ab177327; Abcam), Iba-1 (goat-anti-Iba-1; 1:1,000; #ab5076; Abcam), and GFAP (mouse-anti-GFAP; 1:1,000; #556330; BD Biosciences). Samples were incubated in a PBS solution containing 0.1% TWEEN® 20 (#P9416; Sigma-Aldrich) with secondary antibodies at room temperature for 1 hour. The secondary antibodies are as follows: Cy3-conjugated donkey anti-rabbit IgG (1:1,000; #711-165-152; Jackson ImmunoResearch), Alexa488-conjugated donkey anti-goat IgG (1:1, 000; #705-545-147; Jackson ImmunoResearch), and Alexa488-conjugated donkey anti-mouse IgG (1:1,000; #715-545-150; Jackson ImmunoResearch). Afterward, the cells were mounted with a Vectashield fluorescent material containing DAPI (#H-1200; Vector Laboratories), and images were obtained using a confocal laser scanning microscope, LSM 700, and the ZEN software (Zeiss).

22. Immunohistochemistry

Mice were anesthetized with 400 mg ketamine/kg of body weight, and epidurally perfused, followed by fixation with 4% paraformaldehyde (PFA; #6148; Sigma Aldrich) in PBS. Mouse brains were transferred into 4% PFA at 4° C. for 4 hours, and then stored in a 30% sucrose solution for 1 day. Subsequently, the resulting brains were washed with an O.C.T compound (#4583; Scigen), and sliced at a thickness of 40 μm using a cryotome (#HM 550; Thermo Fisher Scientific) to form samples. The brain samples were stored on slides, and immersed in 2% donkey serum in 0.3% PBST (1×PBS/0.3% Triton X-100) for 30 minutes, followed by incubating with primary antibodies in a blocking buffer at 4° C. overnight. The primary antibodies are as follows: rabbit anti-Olfr110; 1:10,000; #ab177327; Abcam, goat anti-Iba-1; 1:1,000; #ab5076; Abcam, mouse anti-GFAP; 1:1,000; #556330; BD Biosciences)

23. Methods for Knockdown and Rescue Experiments

Mouse primary microglia were placed in a 6-well plate one day before transfection. Subsequently, to differentiate the primary microglia, Lipofectamine RNAiMAX (#13778150, Themo Fisher Scientific) in Opti-MEM (#11058021; Thermo Fisher Scientific) was used according to the manufacturer's protocols. In addition, 100 nM Olfr110 siRNA (#LQ-064350-01-0002; 4 sets of ON-TARGET+ mouse Olfr110 siRNAs; #1: CCUGUAAUUUAUACGC-UAA; #2: CGUUAAGGUACUCAUUUAU; #3: CUGAAUGAAUUGCAGUAUU; #4: GAUUGAU-CUCAGUGCUGUA, Dharmacon) or 100 nM non-targeting siRNA (UGGUUUACAUGUCGACUAA, Thermo Fisher Scientific) were used for incubation for 24 hours. The efficiency of siRNA delivery was confirmed using a siGLO Red oligonucleotide duplex (#D-001630-02-05, Thermo Fisher Scientific). Afterward, an siRNA #3 rescue vector for Olfr110, which had several silent homozygous mutations (5'-CUCAACGAGCUGCAAUACC-3') was generated using the site-directed mutagenesis as described above, and then transfected for 24 hours for Olfr110 knockdown. In a rescue vector experiment, the rescue vector used Lipofectamine LTX (#15338100; Thermo Fisher Scientific) according to the manufacturer's protocol, and was transfected into cells transfected with non-targeting or siRNA #3 for 24 hours.

After the knockdown and rescue experiment, slides were incubated with secondary antibodies in PBST. The secondary antibodies are as follows: Cy3-conjugated donkey anti-rabbit; 1:1,000; #711-165-152; Jackson ImmunoResearch, Alexa488-conjugated donkey anti-mouse; 1:1,000; #715-545-150; Jackson ImmunoResearch, Alexa488-conjugated donkey anti-goat (1:1,000; #705-545-147; Jackson ImmunoResearch). Subsequently, the stained slides were treated with a Vectashield fluorescent material containing DAPI (#H-1200; Vector Laboratories). Images obtained as the results of the experiments were 20× magnified images obtained using a confocal laser scanning microscope, LSM 700 (Zeiss).

24. Methods for Ex Vivo Knockdown and Rescue Experiments

After 9-week-old male CX3CR1$^{GFP/+}$ mice were anesthetized with ketamine, a small hole (~1 mm in diameter) was drilled in the skull to perform stereotaxic injection for accessing the brain (bregma −0.11 mm, 1 mm left spot from longitudinal fissure). According to the manufacturer's protocol, 0.5 μl of siRNA (665 ng) and 0.5 μl of an siGLO Red oligonucleotide duplex (133 ng, #D-001630-02-05, Thermo Fisher Scientific) were injected into the cerebral cortex in the presence of a Mock vector (for knockdown) or a rescue vector (for recovery) using Lipofectamine RNAiMAX. The injection was performed using a Hamilton syringe at a rate of 0.5 μl/min. At 48 hours after injection, ex vivo imaging analysis was performed by the method described above (Takayama et al., 2016) with slight modifications. The delivery of a siRNA construct was able to be confirmed by red fluorescence of the siGLO RED oligonucleotide duplex. In addition, the efficiency of transfection at the injection site was able to be confirmed by qRT-PCR.

25. mRNA-Sequencing and Data Analysis

After a vehicle (control), Sup (MOI 100) or 2-PF (100 μM) treatment for 2 hours, total RNA was isolated from 2×10$^6$ cells of primary microglia using a RNeasy miniKit (Qiagen, 74104), and analyzed using a Qubit RNA HS assay kit (Thermo Fisher Scientific, Q32852) according to the manufacturer's standard protocol for quantification. The RNA integrity number (RIN) of each sample was measured using the Agilent Technologies 2100 BioAnalyzer, and the RINs of all samples were 8.5 or more, which is suitable for mRNA sequencing. Full-length cDNA was generated using a SMARTer-Seq v4 Ultra Low input RNA Kit (Clontech, 634888) according to the manufacturer's recommended protocol. The first strand synthesis of cDNA was initiated from 10 ng total RNA by adding 1 μl of 3' SMART CDS primer II A for 3 minutes at 72° C. The second strand was synthesized by adding SMARTer-seq v4 oligo and SMART-Scribe reverse transcriptase, and the reaction product was incubated at 42° C. for 90 minutes and inactivated at 70° C. for 10 minutes. The double-stranded cDNA was amplified 8 cycles by PCR, and purified using Agencourt AMPure beads (Beckman, A63881). An mRNA-seq library was generated using a Nextera XT DNA library preparation kit (Illumina, FC-131-1024) according to the manufacturer's protocol. cDNA was subjected to tagmentation (fragmentation and tagging with a sequencing adaptor) and amplified by PCR using Index Primers of a Nextera XT DNA Index Kit (Illumina, FC-131-1001). After PCR, the DNA library was purified using AMPure beads and quality was assessed by an Agilent 2100 Bioanalyzer. A DNA library of each sample was quantified using a KAPA library quantification kit (KAPA Biosystems, KK4854) and then pooled. All libraries were sequenced using an Illumina Hiseq2500 instrument to generate dual-indexed 100-bp paired reads, thereby obtaining an average of 58 million reads for each sample. The quality of raw sequences was confirmed using FastQC (Babraham Bioinformatics), and trimmed adaptor sequences using cutadapt software. The remaining reads were aligned to the mouse reference genome (GRCm38) using TopHat (Trapnell et al., 2009) with default options. Afterward, the aligned reads were assembled into annotated genes, and fragments per kilobase per million mapped reads FPKM were calculated using Cufflinks (Trapnell et al., 2010).

26. Selection of Differentially Expressed Genes

On average, 58 million pieces of data were collected from each sample, and 89.9% of the data aligned to the mouse reference genome. Genes with FPKM>1 in at least one sample have been shown to be expressed as previously described (Graveley et al., 2011). After collecting FPKM values of each sample, quantile normalization was applied to the FPKM values converted into log$_2$ (Bolstad et al., 2003).

To identify DEGs, these normalized values were compared using an integrated statistical test reported previously (Lee et al., 2010). The comparison is for comparing Sup-treated samples with Control (Sup), and comparing 2-PF-treated samples and Control (2-PF). First, a T-value was obtained by performing a Student's t-test on each gene, and random sampling experiments were performed 1,000 times, and the T-values obtained thereby were subjected to Gaussian kernel density estimation. An empirical null distribution for the T-values was created. In addition, the corrected P value of the observed T-value of each gene was calculated using the empirical distribution by a two-tailed test. DEGs were identified as genes with a corrected P value of less than 0.05 and an absolute log$_2$-median-ratio>cutoff (log 2-fold change=0.41 and 0.54 for Sup vs. control and 2-pF vs. control).

The cutoff was determined as an average of the $5^{th}$ and $95^{th}$ percentile values in the distribution of log$_2$-fold changes obtained from the random sampling experiments described above. Enrichment analysis of a Gene Ontology Biological Process (GOBP) was performed using the DAVID software (Huang da et al., 2009). As a result, the enriched GOBP was P<0.05 calculated from DAVID, and a count was ≥3.

27. cAMP ELISA

Primary microglia were seeded in 48-well plates (2×10$^5$ cells/well) and treated with 30 μM forskolin (#F3917, Sigma Aldrich) or 2-PF (10, 100, 500 μM) for 30 minutes. To confirm the effect of an inhibitor, 1 mM of S Q22536 (#17318-31-9; Calbiochem) was pretreated first for 30 minutes. The cells were lysed in 0.1 M of HCl with 1% Triton X 100 for 10 minutes, the lysate was centrifuged at 600×g for 2 minutes. The resulting supernatant was directly used for cAMP analysis with a cAMP ELISA kit (Enzo Life Science) according to the manufacturer's protocol. An optical density at 405 nm was measured using a VersaMax microplate reader (Molecular Devices).

28. Calcium Imaging

Twenty-four hours after newly isolated microglia were mounted on poly-D-lysine-coated 18-mm aperture microscope cover glasses (#0111580; Marienfeld), the microglia were incubated in a superfusion chamber for 30 minutes. The chamber contained 4 μM of Fura-2/AM (Ca$^{2+}$-sensitive fluorescent dye; #F1221; Thermo Fisher Scientific) in Ringer's solution (115 mM NaCl, 2.5 mM KCl, 1 mM CaCl$_2$, 1.5 mM MgCl$_2$, 4.5 mM HEPES, pH 7.4) filtered through a filter with a 0.22-μm pore. After calcium staining culture, the chamber was placed under an inverted microscope and washed with Ringer's solution for 20 minutes prior to 3-PF treatment. Here, a flow rate of the solution is 12 ml/min. Subsequently, primary microglia were treated with 300 μM ATP (#A2383; Sigma Aldrich) for 5 seconds. After washing for 5 minutes, the primary microglia were treated with a 100 μM 2-PF solution for 5 seconds. This step was accomplished with two different concentrations (300 and 1000 μM) of 2-PF solution. Finally, the microglia were treated with a 300 μM ATP solution for 5 seconds. An emitted fluorescent material was photographed every 2 seconds using a CCD camera. Pseudo-color images were converted using fractional fluorescence changes ($\Delta F/F$, $\Delta[Ca^{2+}]i$). In addition, these images show changes in intracellular calcium ions. The color intensity of the photographed images was set to a maximum of 1.5±0.1 AU (arbitrary linear units) and a minimum of 0.4±0.1 AU. The representative calcium ion peak was selected after analysis of 160 cells.

29. Chemicals and Inhibitors

Chemicals used in this experiment were purchased from Sigma-Aldrich. All purchased compounds are as follows: Acetic acid (#695092), acetone (#W332607), 2 aminoacetophenone (#W390607), dimethyl sulfide (#471577), ethanol (#E7023), hexanal (#115606), hydrogen sulfide (#742546), indole (#W259306), isopentanol (#320021), 2-pentylfuran (#W331708), trimethylamine (#W324108), furan (#185922), 2-methylfuran (#M46846), 2,3-dimethylfuran (#428469), 2-ethylfuran (#W367303), 2-propylfuran (#P1488; Tokyo Chemical Industry, TCI), 2-butylfuran (#CDS001204), 2-t-butylfuran (#386278), 2-hexylfuran (#H26698; Alfa Aesar), and 2-heptylfuran (#A10604; Alfa Aesar) were diluted in DMS (#D2650; Sigma Aldrich). ATP (#A2383; Sigma Aldrich) was diluted in DMSO. Inhibitors for adenylyl cyclase, PKA, ERK, G, and PLC pathways, which are diluted in DMSO, inhibitors with following concentrations: pd98059 50 μM (#PHZ1164; Thermo Fisher Scientific), 300 SQ22536 (#568500; Calbiochem), 5 μM U73122 (#662035; Calbiochem), 10 μM H-89 (#tlrl-h89; InvivoGen), and 10 μM Gallein(#371709; Calbiochem. Each inhibitor was pretreated 1 hour before the experiment.

30. Statistical Analysis Method

In this experiment, all data is expressed as means±SEM. Statistical significance was determined by an unpaired Student's t-test for comparing repeated measurements and respective control values using the GraphPad Prism 5 Software package (GraphPad Software Inc.).

Example 1. Confirmation of Microglial Activation of Metabolites by *S. Pneumoniae*

Disease behavior is known as one of the symptoms caused by excessive secretion of cytokines (Dantzer et al., 2008). In this experiment, a *S. pneumoniae* culture was intraperitoneally injected into a mouse, and then the mobility of the mouse was examined to determine the induction of and response to disease behavior. Among the responses shown in the mouse, a change in intake, a change in body weight, or a change in temperature corresponds to an immediate response. The inventors focused on a change in mouse mobility (Dantzer et al., 2008). After intraperitoneal injection, a significant change (P<0.01) in mouse mobility was confirmed, and such a change was also significantly dependent on an injection amount (FIG. 1). Conversely, it was observed that mice into which a control was intraperitoneally injected did not show any symptom. The symptom and disease behavior are caused by excessive cytokine secretion of the immune system (Konsman et al., 2002), and to confirm whether cytokines are actually secreted in mice, cytokine mRNA levels in the cerebral cortex were measured and compared. Here, as an analysis method, quantitative real-time polymerase chain reaction (qPT-PCR) was used. It was confirmed that, in the experimental group, compared to the control, the intraperitoneal injection can significantly increase the secretion of both inflammatory and non-inflammatory cytokines in the cerebral cortex (P<1.0×10$^{-3}$) (FIG. 2). After infection, microglia and astrocytes are known to secrete both pro- and anti-cytokines (Norden et al., 2016). When the microglia and the astrocytes were intraperitoneally injected, the inventors investigated whether cytokine secretion was preferentially increased. As a result, a significant increase in the mRNA secretion of five cytokines was confirmed in microglia (P<1.0×10$^{-3}$). The five cytokines are Tnf, I16, I11b, I110 and I113, all of which increased by microglia injection, but not by astrocyte injection (FIG. 3). In addition, it was also confirmed that the increases in Tnf, I16 and I11b are dose-dependent (FIG. 4).

In addition, it is known that, microglial activation brings a morphological change from the existing divided form to an amoeba form, and also increases both the number and the length of each cell (Kreutzberg, 1996). To confirm the morphological changes, using microglia-specific tagged GFP, GFP intensity in CX3CR1$^{GFP/+}$ mice was compared with that of the control. As a result, it was confirmed that the GFP intensity is significantly higher (P<1.0×10$^{-3}$) in the group into which microglia were intraperitoneally injected, compared to the control. This means that microglial activation is caused by 2-PF injection, and the number and length microglia are increased (FIG. 5). Moreover, according to the passage of time, it was confirmed that microglia are activated, and their morphologies are changed. This is a change from a divided form to an amoeba form. In addition, compared to the control, it was seen that the GFP intensity of microglia in the Sup-injected experimental group is significantly higher (P<1.0×10$^{-3}$). Therefore, it is concluded that microglial activation occurs after 2-PF injection, and a morphological change also occurs (FIGS. 6 to 8).

Consequently, it was confirmed that small molecules derived from *S. pneumoniae* increase cytokine secretion and also increase phagocytosis (FIGS. 9 and 10), and induce microglial activation causing the morphological change in microglia.

Example 2. Confirmation of Interaction Between 2-PF and Microglial Olfr110

The inventors hypothesized that metabolites released from *S. pneumoniae* can bind to OR and induce microglial activation. First, to determine an OR candidate, mRNA sequencing was performed on primary microglia. It was confirmed that, among 13 ORs (Olfr111, Olfr110, Olfr482, Olfr99, Olfr132, Olfr115, Olfr77, Olfr543, Olfr461, Olfr455, Olfr1420, Olfr1417 and Olfr57) found as described above, Olfr111 and Olfr110 are expressed at the highest levels (FIG. 11). Seven ORs (Olfr110, Olfr111, Olfr99, Olfr1029, Olfr433, Olfr222, and Olfr920) expressed in microglia were also found using a gene phenotype database (GSE52564; (Zhang et al., 2014). The seven ORs include Olfr111 and Olfr110, which are specifically expressed in microglia, compared to other cells. By integrating these processes, a total of 17 candidate receptors were yielded.

Many receptors recognizing pathogen-associated patterns are also induced by pathogen infection for effective immune responses (Womle et al., 2006). Therefore, it was first investigated by qRT-PCR to see whether 17 OR candidates were induced from the primary microglia after Sup treatment. As a result, it was confirmed that the Sup treatment increase Olfr111 and Olfr110 to the highest level, followed by Olfr920, Olfr1417 and Olfr99 (FIG. 12). Afterward, it was investigated whether these five OR candidates react with volatile molecules in Sup.

Through the mRNA-sequencing analysis on microglia, 11 volatile metabolites (Olfr111, Olfr110, Olfr482, Olfr99, Olfr132, Olfr115, Olfr77, Olfr543, Olfr461, Olfr455, Olfr1420, Olfr1417 and Olfr57) derived from *S. pneumoniae* were selected. After it was confirmed that the OR candidates were immediately infected by the 11 metabolites and then activated, reactivity was confirmed using a luciferase assay (Zhuang and Matsunami, 2008) with Hana3A cells. Among the 11 metabolites, which shows the highest reactivity with 2-PF was investigated. The other three receptors show higher reactivity with ethanol, but also react with MOCK, considered to be a non-specific reaction. Therefore, such results mean that Olfr111 and Olfr110 can serve as selective ligands for 2-PF (FIG. 13).

To further evaluate 2-PF-OR, the receptors were analyzed at a molecular level. More specifically, reactivity was compared by a luciferase assay, after 2-PF was treated with Olfr111 and Olfr110. These analogues included five furans, such as 2-PF, 2-butylfuran, 2-t-butylfuran, 2-hexylfuran, and 2-propylfuran. All of the five furans showed reactivity to Olfr111 and Olfr110 (FIGS. 14 to 16). Particularly, among these, 2-PF showed the highest reactivity, and particularly showed the highest reactivity with Olfr110 (data not shown). The key residues of Olfr110 binding to 2-PF were investigated by homology modeling of Olfr110 and docking analysis between Olfr110 and 2-PF. The docking analysis predicting amino acids of Olfr110 is important for hydrophobic interactions between 2-PF and F102 and F104 in transmembrane domain 3, and Y252 and Y259 in transmembrane domain 6 (FIG. 17). Among these, it can be seen that F104 and Y252 are particularly important for odorant recognition by MOR256-3. Analysis was performed using one of the four residues (F102, F104, Y252 and Y259) predicted by a luciferase assay, or a method of inducing multiple site-directed mutagenesis. As a result, in the case of an F104W mutation, luciferase activity was completely lost, indicating that F104 plays the most important role in the interaction between 2-PF and Olfr110 (FIG. 18). After 2-PF treatment, a chemotaxis assay showed that Olfr111- or Olfr110-treated cells are increased in mobility in a concentration-dependent manner. This data shows that the interaction between 2-PF and Olfr110 can change cellular functions, for example, increase cell migration (FIG. 19)

Example 3. Confirmation of Microglial Activation by 2-PF 3.1. Confirmation of Microglial Activation by 2-PF Next, it was investigated whether 2-PF is present in Sup using liquid-chromatography-tandem mass spectrometry (LC-MS/MS). After data on 2-PF was obtained using liquid-chromatography-tandem mass spectrometry (LC-MS/MS), a 2-PF ion precursor was identified using a mass-to-charge ratio (m/z=153.091). As a result, precursor ions were confirmed in Sup, but not in a control (FIG. 20). The same MS spectrum was also observed in both synthetic 2-PF and Sup (FIG. 21). As a result of comparing the intensity of 2-PF precursor ions between treatment with F102 and treatment with F104, it was confirmed that the F104 treatment increases the intensity (56.0-fold) more than that of the F102 treatment (FIG. 22). This result shows that 2-PF is specifically present in Sup. In addition, to examine whether 2-PF induces microglial activation in Sup, 2-PF is treated at 100, 300 and 500 μM, and microglia were primarily treated. As a result, chemotaxis (FIG. 23), ROS secretion (FIG. 24) and phagocytosis (FIG. 25) are significantly increased in a concentration-dependent manner (P<1.0×10$^{-3}$).

Next, an experiment for metabolites induced by 2-PF in a mouse brain was conducted. It was found that Olfr110 is expressed in microglia, and confirmed by western blotting using antibodies that Olfr110 is specifically expressed in microglia, but not in olfactory tissue or astrocytes (FIG. 26).

Immunostaining was used to confirm strong expression in Olfr110, but not in GFAP-positive astrocytes or NeuN-positive neurons in the cerebral cortex, and GFP (+) microglia of CX3CR1$^{GFP/+}$ mice (FIG. 28). In various cerebral regions such as the cerebral cortex, hippocampus, hypothalamus, and substantia nigra, specific Olfr110 expression was observed in Iba-1-positive microglia (data not shown). It was shown that Sup treatment induces mRNA expression of Olfr110 (FIG. 21), and increases a protein level of Olfr110 (FIG. 29, top image). Interestingly, 2-PF significantly increases an Olfr110 level ($P<1.0\times10^{-3}$) (FIG. 29, bottom image). As a pathological behavior induced by 2-PF injection, a concentration-dependent decrease in mouse mobility was shown (FIG. 30). The 2-PF injection also significantly increased an expression level of inflammatory cytokines ($P<0.05$; Tnf, Il6, Il1b, and Il10) (FIG. 31). The intensity of GFP expression in 2-PF treated CX3CR1$^{GFP/+}$ mice was also highly increased (FIG. 32). These results mean that 2-PF-induced morphological changes in microglia can lead to microglial activation. In addition, it was investigated whether 2-PF can change ex vivo phagocytosis of microglia after 2-PF culture in brain slices of CX3CR1$^{GFP/+}$ mice. Through time-lapse confocal microscopy imaging, it was seen that the capacity of microglia, a protrusion degree, and the activity of phagocytosis are increased (FIG. 33), and it was seen that, as macrophages are significantly increased ($P<1.0\times10^{-3}$), phagocytosis is also increased (FIG. 22). Taken together, this data suggests that 2-PF activates microglia in the brain.

3.2. Experiment for Increasing Disease Behavior

It is known that an increase in disease behavior by microglial activation is due to an increase in secreted cytokines. To confirm the increase in disease behavior with the increase in cytokines, this experiment was conducted. The evaluation of disease behavior was accomplished after IP injection of Sup or 2-PF into the mice.

After IP injection, a mouse was placed in a space with four open sides (40×40×40 cm, white field, black wall), and the location of the mouse was recorded with a camera for 30 minutes, and then a moving distance thereof was calculated. Afterward, the data was plotted in a pseudo-color heat map using EthoVision XT (Noldus, Netherlands).

3.3. Experiment for Increasing Ex Vivo Phagocytosis

In this experiment, to examine the phagocytotic action of microglia, the brain of a 9-week-old male CX3CR1$^{GFP/+}$ mouse was sliced to a thickness of 150 µm using a vibratome (Leica VT1200), and stored in a ice-cooled artificial cerebrospinal fluid (aCSF: 120 mM NaCl, 25 mM NaHCO$_3$, 1.25 mM NaH$_2$PO$_4$, 5 mM KCl, 1 mM CaCl$_2$, 1 mM MgSO$_4$, 305 mOsm glucose, pH7.4). Afterwards, the sliced brain was incubated to remove cell debris. Oxygen-treated aCSF was pretreated in a perfusion chamber at 37° C. for 2 hours. Subsequently, before incubation, the sliced brain was incubated with 500 µl of aCSF containing $9.10\times10^7$ microspheres (360/407 mm; #17458; Polysciences), and covered with a customized nylon grid. Time lapse videos were recorded every minute for 92 minutes using a confocal microscope. The number of phagocytosing microglia was counted from the images.

Example 4. Whether or not Olfr110 Controls Microglial Activation by 2-PF

The inventors tested whether 2-PF-induced microglial activation is mediated by Olfr110. In this experiment, specific siRNA for Olfr110 and a specific mutant vector rescue structure of Olfr110 restoring siRNA were designed. #3 of four siRNA candidates was able to effectively decrease mRNA and protein levels of Olfr110 in Hama3A cells. After transfection, reductions in mRNA and protein in primary microglia were confirmed, and the rescue vector restored the reductions in mRNA and protein induced by siRNA. It was confirmed that, using siRNA and a rescue vector, the effect of Olfr110 on 2-PF-induced microglial activation was able to be confirmed. First, Olfr110 knockdown reduced an increase in mRNA levels of inflammatory cytokines of primary macroglia induced by 2-PF, and conversely, the rescue vector restored the knockdown effect. In addition, a similar effect was observed at an mRNA level as well as a protein level. Increased ROS induced by 2-PF was reduced by siRNA, and restored by the rescue vector. However, an ROS increase mediated by a P2Y receptor was not affected by the presence of the rescue vector. After Olfr110 knockdown and rescue effects, similar 2-PF-induced effects on phagocytosis and chemotaxis were observed.

Next, the inventors investigated whether the Olfr110 knockdown and rescue effects occur in mouse brains. More specifically, combinations of non-targeting siRNA+Mock+siGLO (Ctrl), Olfr110 siRNA+Mock+siGLO (siOlfr110), and Olfr110 siRNA+rescue vector+siGLO (Rescue) were introduced to the cerebral cortex of CX3CR1$^{GFP/+}$ mice by stereotactic injection (Takayama et al., 2016). After injection, in mouse brain slices, transfected microglia (yellow) and non-transfected microglia (green), and transfected non-microglia (red) were compared and observed (FIG. 39). After microdissection of a fluorescent region of the sliced brain fragment, an expression level of Olfr110 was measured using qRT-PCR. As a result, it was observed that, after siOlfr110 injection, a significant decrease in corresponding OR was found ($P<1.0\times10^{-3}$), and there was no change in a negative control Olfr920. The inventors observed that similar knockdown and rescue effects were also observed in the cerebral cortex of a CX3CR1$^{GFP/+}$ mouse. Taken together, Olfr110 can control 2-PF-induced microglial activation (cytokine secretion, ROS secretion, cytotoxicity and phagocytosis) in vitro and ex vivo.

Example 5. Control of Olfr110-Dependent Microglial Activation Induced by 2-PF by $G_{\alpha s}$-s-cAMP-PKAERK and $G_{\beta\gamma}$-PLC-Ca$^{2+}$ Pathways To understand the molecular aspect of Olfr110-mediated microglial activation, mRNA-sequence analysis of primary microglia treated with Sup or 2-PF was performed in this experiment. 1124 and 1438 differentially expressed genes (DEGs) were identified using mRNA-sequencing data (FIG. 42). It was confirmed that a significant part ($P<0.01$) of these DEGs (22.5 and 17.6% of 1124 and 1438 DEGs) includes 253 genes, and in this experiment, it was confirmed that the 253 genes are shared between two experimental groups. Among these 253 shared DEGs, 135 and 78 genes were consistently up-regulated or down-regulated in 2-PF-treated microglia, but the other 40 genes were not (FIG. 43). Next, overlapping genes which overlap upwards and downwards were investigated using gene ontology biological processes (GOBPs). The up-regulated genes are associated with microglial activity. Specific details on activation are as follows (FIG. 44): cytokine secretion (cytokine generation and secretion), chemotaxis (blood cell migration and chemotaxis), ROS generation (cellular responses to ROS and ROS metabolic process) and phagocytosis. This data means that both Sup and 2-PF-treated experimental groups up-regulate genes involved in microglial activation, but the down-regulated genes regulate transcription (data not shown). As a result, it was confirmed that 2-PF binding to Olfr110 is involved in microglial activation, thereby activating a signaling pathway inducing upregulation. To understand such a signaling system, it was necessary to reconstruct a network model describing interactions associated with cytokine production, chemotaxis, ROS generation and phagocytosis (data not shown). The newly established model revealed that cAMP, MAPK, PI3K, PLC, and Ca$^{2+}$ signaling pathways up-regulate genes involved in microglial activation, which is consistent with previous results (Verderio and Matteoli, 2001).

Next, the effects of 2-PF were examined using the established network model. For the cAMP signaling pathway, a cAMP concentration in primary microglia was measured after 2-PF treatment. As a result, cAMP treated by an adenylyl cyclase inhibitor showed that microglial activation was increased by 2-PF treatment in a concentration dependent manner (FIG. 45). Olfr110 siRNA was able to decrease cAMP production induced by 2-PF, and when the rescue vector was injected, the opposite effect was able to be obtained (FIG. 46). For a calcium signaling pathway, calcium imaging was performed after 2-PF treatment. As a result, it was confirmed that intracellular calcium ion levels increased according to an injection amount (FIG. 47). For MAPK and PI3K signaling pathways, the phosphorylation levels of ERK, p38, JNK, and Akt were measured, and it was confirmed that the phosphorylation levels after treatment increased from 2 minutes and stopped increasing at 20 minutes. Next, the relative contribution to microglial activation was investigated using the inhibitors for signaling pathways. After pretreatment with adenylyl cyclase (SQ22536), PKA (H-89), ERK (pd98059), or PLC inhibitor (U73122), 2-PF protein was treated, and Tnf and 116 cytokine levels were measured. As a result, it was confirmed that the cytokine levels showed a great decrease by SQ22536 or H-89, and a relatively less decrease by pd98059 or U73122 (FIG. 49). Particularly, U73122 completely inhibited ROS generation ($P<1.0\times10^{-3}$) (FIG. 50). It was confirmed that ROS generation can be similarly inhibited by gallein, which is an inhibitor of $G_{\alpha s}$-cAMP-PKAERK and $G_{\beta\gamma}$-PLC-$Ca^{2+}$ pathways (Bonacci et al., 2006; Ukhanov et al., 2011). All inhibitors considerably decreased phagocytosis ($P<0.05$), and almost completely decreased chemotaxis ($P<1.0\times10^{-3}$). CREB and ERK phosphorylation was greatly decreased by SQ22536 and pd98059 (FIG. 53). This study shows that the $G_{\alpha s}$-cAMP-PKA-ERK pathway regulates cytokine production, cytotoxicity, and phagocytosis, whereas the $G_{\beta\gamma}$-PLC-$Ca^{2+}$ pathway regulates ROS generation.

Example 6. Selection of Competitive Inhibitors Against 2-PF

There was a previous report that OR is structurally associated with an activator and an inhibitor. Based on this, the inventors selected 2-ethylfuran (2-EF) reducing 2-PF activity by simultaneous treatment with 2-PF and derivatives which do not bind to either Olfr110 or Olfr1111 (2-methylfuran, 2,3-dimethylfuran, 2-ethylfuran, 2-hexylfuran, or 2-heptylfuran). After Olfr110 was transfected into Hana3A cells and 2-PF was fixed at 300 μM, 2-EF was treated at different concentrations from 1 μM to 10 mM, together with 2-PF, to measure competitive activity, confirming that as the 2-EF level increases, 2-PF activity decreases ($K_d$=120 μM). Consequently, ROS induced by 2-PF, which is an Olfr110 agonist, is decreased by 2-EF, which is its competitive inhibitor (antagonist) (FIG. 54). To confirm the microglial activity of 2-EF selected as a competitive inhibitor, 2-EF was pretreated at concentrations of 0, 100, 300, and 500 μM in primary microglia, and 100 MOI of Sup was treated, followed by measurement of an amount of ROS generation. As a result, it was observed that the amount of ROS generated by treatment of 100 MOI Sup is diminished as the 2-EF level increases (FIG. 55, left). Subsequently, Sup was treated with MOI 5 and simultaneously treated with 500 μM 2-PF, and 2-EF was simultaneously treated at 0, 100, 300, or 500 μM. As a result, ROS was generated by MOI 5, and ROS generation was further increased by 500 μM of 2-PF (FIG. 55, right). However, it was confirmed that the higher the concentration of 2-EF added, the lower the concentration of the generated ROS. This means that ROS was inhibited by 2EF, which is an economic inhibitor.

According to an OR of microglia and its use according to an aspect, microglia can be detected by measuring an activity or expression level of an OR, that is, Olfr110 or Olfr111 protein, and using this, a ligand of the OR for microglia cannot only be selected, but also used in treatment of a neuroinflammatory disease or meningitis with an inhibitor or activator against the interaction between the OR and 2-PF.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

According to the present invention, microglia may be detected by measuring a protein activity level or protein expression level of Olfr110 or Olfr111, OR ligands of microglia may be selected using them, and inhibitors or activators of the interaction between the OR and 2-PF can be used in treatment of a neuroinflammatory disease or meningitis. Therefore, the present invention can be applied to conduct related studies by detecting macroglia and selecting ligands thereof in a basic research field and clinically, and the inhibitors or activators may further be effectively used in the field of development of therapeutic agents for a neuroinflammatory disease or meningitis.

The invention claimed is:

1. A method of preventing or treating a neuroinflammatory disease or meningitis, comprising:
administering a pharmaceutical composition comprising an inhibitor against the interaction between 2-pentyl-furan and an odorant receptor, which is odorant receptor 110 (Olfr110) or odorant receptor 111 (Olfr111), as an active ingredient, to a subject in need thereof.

2. The composition of claim 1, wherein the meningitis is bacterial meningitis.

3. The method of claim 1, wherein the interaction inhibitor comprises an antisense nucleotide, a short hairpin RNA, or small interfering RNA, which complementarity binds to mRNA of the Olfr110 or Olfr111.

4. The method of claim 1, wherein the interaction inhibitor comprises a peptide, peptide mimetic, a substrate analog, aptamer or antibody, which complementarity binds to a protein of the Olfr110 or Olfr111.

5. The method of claim 1, wherein the inhibitor against the interaction between the 2-pentylfaran and the Olfr110 or Olfr111 comprises one or more selected from the group consisting of 2-methylftiran, 2,3-dimethylfuran, 2-ethylfuran, 2-propylfuran, 2-butylfuran, 2-t-butylfuran, 2-hexylfuran, 2-heptylfuran and a derivative thereof which inhibits the interaction between 2-pentylfuran and the Olfr110 or Olfr111.

* * * * *